(12) United States Patent
Thaler et al.

(10) Patent No.: US 10,501,437 B2
(45) Date of Patent: Dec. 10, 2019

(54) CRYSTALLINE FORMS OF N-[2-(3-HYDROXY-3-METHYLBUTYL)-6-(2-HYDROXYPROPAN-2-YL)-2H-INDAZOL-5-YL]-6-(TRIFLUOROMETHYL)PYRIDINE-2-CARBOXAMIDE

(71) Applicant: Bayer Pharma Aktiengesellschaft, Berlin (DE)

(72) Inventors: Tobias Thaler, Köln (DE); Johannes Platzek, Berlin (DE); Nicolas Guimond, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 16/097,506

(22) PCT Filed: Apr. 25, 2017

(86) PCT No.: PCT/EP2017/059764
§ 371 (c)(1),
(2) Date: Oct. 29, 2018

(87) PCT Pub. No.: WO2017/186700
PCT Pub. Date: Nov. 2, 2017

(65) Prior Publication Data
US 2019/0152944 A1    May 23, 2019

(30) Foreign Application Priority Data

Apr. 29, 2016 (EP) ..................................... 16167649
Apr. 29, 2016 (EP) ..................................... 16167650

(51) Int. Cl.
*C07D 401/12* (2006.01)
*A61K 9/20* (2006.01)

(52) U.S. Cl.
CPC .......... *C07D 401/12* (2013.01); *A61K 9/2095* (2013.01); *C07B 2200/13* (2013.01)

(58) Field of Classification Search
CPC ......................... C07D 401/12; A61K 31/4439
USPC ........................................ 546/275.7; 514/338
See application file for complete search history.

(56) References Cited

U.S. PATENT DOCUMENTS

| | | | |
|---|---|---|---|
| 8,293,923 | B2 | 10/2012 | Guckian et al. |
| 9,951,086 | B2 | 4/2018 | Bothe |
| 10,308,634 | B2 | 6/2019 | Bothe |
| 2005/0054627 | A1 | 3/2005 | Carter et al. |
| 2013/0274241 | A1 | 10/2013 | Jorand-Lebrun et al. |
| 2017/0349570 | A1* | 12/2017 | Bothe .................. C07D 401/12 |
| 2018/0201609 | A1 | 7/2018 | Gummadi |
| 2018/0289685 | A1 | 10/2018 | Bothe |
| 2019/0071432 | A1 | 3/2019 | Bothe |
| 2019/0106407 | A1 | 4/2019 | Thaler |
| 2019/0112270 | A1 | 4/2019 | Thaler |
| 2019/0125736 | A1 | 5/2019 | Rausch |
| 2019/0144420 | A1 | 5/2019 | Thaler |

FOREIGN PATENT DOCUMENTS

| | | |
|---|---|---|
| EP | 2045253 | 4/2009 |
| WO | WO-2007091107 | 8/2007 |
| WO | WO-2011043479 | 4/2011 |
| WO | WO-2011153588 | 12/2011 |
| WO | WO-2013106254 | 7/2013 |
| WO | WO-2015091426 | 6/2015 |
| WO | WO-2015104662 | 7/2015 |
| WO | WO-2016083433 | 6/2016 |
| WO | WO2016174183 A1 | 11/2016 |
| WO | WO2017148902 A1 | 9/2017 |
| WO | WO2017186689 A1 | 11/2017 |
| WO | WO2017186693 A1 | 11/2017 |
| WO | WO2017186703 A1 | 11/2017 |
| WO | WO2017207386 A1 | 12/2017 |
| WO | WO2017207481 A1 | 12/2017 |

OTHER PUBLICATIONS

Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Abbate, A. et al. (2010). "Interleukin-1 Blockade with Anakinra to Prevent Adverse Cardiac Remodeling After Acute Myocardial Infarction (Virginia Commonwealth University Anakinra Remodeling Trial [VCU-ART] Pilot Study)," *Am J Cardiol* 105: 1371-1377.
Abbate, A. et al. (2013). "Effects of Interleukin-1 Blockade With Anakinra on Adverse Cardiac Remodeling and Heart Failure After Acute Myocardial Infarction [from the Virginia Commonwealth University—Anakinra Remodeling Trial (2) (VCU-ART2) Pilot Study]," *The American Journal of Cardiology* 111: 1394-1400.
Akash, M.S.H. et al. (2012). "Interleukin-1 Receptor Antagonist: A New Therapy for Type 2 Diabetes Mellitus," *Journal of Pharmaceutical Sciences* 101(5): 1647-1658.
Akcay, A. et al. (2011). "IL-33 Exacerbates Acute Kidney Injury," *J Am Soc Nephrol* 22: 2057-2067.
Akoum, A. et al. (2007). "Imbalance in the expression of the activating type I and the inhibitory type II interleukin 1 receptors in endometriosis," *Human Reproduction* 22(5): 1464-1473.
Allhorn, S. et al. (2008). "TLR3 and TLR4 expression in healthy and diseased human endometrium," *Reproductive Biology and Endocrinology* 6(40): 1-11.

(Continued)

*Primary Examiner* — Deepak R Rao
(74) *Attorney, Agent, or Firm* — Morrison & Foerster LLP

(57) ABSTRACT

The present invention relates to crystalline forms of N-[2-(3-Hydroxy-3-methylbutyl)-6-(2-hydroxypropan-2-yl)-2H-indazol-5-yl]-6-(trifluoromethyl)pyridine-2-carboxamide, to processes for their preparation, to pharmaceutical compositions comprising them and to their use in the control of disorders.

12 Claims, 7 Drawing Sheets

(56) References Cited

OTHER PUBLICATIONS

Ashimori, A. et al. (1990). "Novel 1,4-Dihydropyridine Calcium Antagonists. I. Synthesis and Hypotensive Activity of 4-(Substituted Pyridyl)-1, 4-dihydropyridine Derivatives," *Chem. Pharm. Bull.* 38(9): 2446-2458.

Baddam, S.R. et al. (2013). "Regioselective methylation of indazoles using methyl 2,2,2-trichloromethylacetimidate," *Tetrahedron Letters* 54: 1661-1663.

Bauer, E.M. et al. (2012). "High Mobility Group Box 1 Contributes to the Pathogenesis of Experimental Pulmonary Hypertension via Activation of Toll-like Receptor 4," *Molecular Medicine* 18: 1509-1518.

Béraud, D. et al. (2012). "Misfolded α-synuclein and toll-like receptors: therapeutic targets for Parkinson's disease," *Parkinsonism and Related Disorders* 18S1: S17-S20.

Bethanamudi, P. et al. (2012). "Synthesis of Novel $N^1$ and $N^2$ Indazole Derivatives," *E-Journal of Chemistry* 9(4): 1676-1682.

Bijani, F.M. et al. (2012). "Toll-like Receptor Signaling Pathways in Cardiovascular Diseases: Challenges and Opportunities," *International Reviews of Immunology* 31: 379-395.

Bomfim, G.F. et al. (2012). "Toll like receptor 4 contributes to blood pressure regulation and vascular contraction in spontaneously hypertensive rat," *Clin Sci (Lond)* 122(11): 535-543.

Brough, D. et al. (2011). "Regulation of interleukin-1 in acute brain injury," *Trends in Pharmacological Sciences* 32(10): 617-622.

Bunting, M.M. et al. (2013). "Interleukin-33 Drives Activation of Alveolar Macrophages and Airway Inflammation in a Mouse Model of Acute Exacerbation of Chronic Asthma," *BioMed Research International* 10 pages.

Byers, D.E. et al. (2013). "Long-term IL-33-producing epithelial progenitor cells in chronic obstructive lung disease," *The Journal of Clinical Investigation* 123(9): 3967-3982.

Cameron, B. et al. (2012). "Loss of Interleukin Receptor Associated Kinase 4 Signaling Suppresses Amyloid Pathology and Alters Microglial Phenotype in a Mouse Model of Alzheimer's Disease," *J. Neurosci* 32(43): 15112-15123.

Cario, E. (2010). "Toll-like Receptors in Inflammatory Bowel Diseases: A Decade Later," *Inflamm Bowel Dis* 16(9): 1583-1597.

Carty, M. et al. (2011). "Evaluating the role of Toll-like receptors in diseases of the central nervous system," *Biochemical Pharmacology* 81: 825-837.

Cevikbas, F. et al. (2012). "IL-33: A Novel Danger Signal System in Atopic Dermatitis," *Journal of Investigative Dermatology* 132: 1326-1329.

Chakrabarty, M. et al. (2008). "An expedient, regioselective synthesis of novel 2-alkylamino- and 2-alkylthiothiazolo[5,4-e]- and -[4,5-g]indazoles and their anticancer potential," *Tetrahedron* 64: 6711-6723.

Chang, J.H. et al. (2012). "Recent advances in Toll-like receptors and anterior uveitis," *Clinical and Experimental Ophthalmology* 40: 821-828.

Chen, D-Y. et al. (2013). "Involvement of TLR7 MyD88-dependent signaling pathway in the pathogenesis of adult-onset Still's disease," *Arthritis Research & Therapy* 15: 1-12.

Cheung, M. et al. (2003). "Efficient and Regioselective Synthesis of 2-Alkyl-2H-indazoles," *J. Org. Chem.* 68: 4093-4095.

Chirkova, Z.V. et al. (2012). "Synthesis of Substituted Indazole-5,6-dicarbonitriles," *Russian Journal of Organic Chemistry* 48(12): 1557-1560.

Choi, J-W. et al. (2013). "MYD88 expression and L265P mutation in diffuse large B-cell lymphoma," *Human Pathology* 44: 1375-1381.

Chopra, P. et al. (2013). "Treatment of Complex Regional Pain Syndrome (CRPS) Using Low Dose Naltrexone (LDN)," *J Neuroimmune Pharmacol* 8: 470-476.

Christensen, S.R. et al. (2006). "Toll-like Receptor 7 and TLR9 Dictate Autoantibody Specificity and Have Opposing Inflammatory and Regulatory Roles in a Murine Model of Lupus," *Immunity* 25: 417-428.

Christia, P. et al. (2013). "Targeting inflammatory pathways in myocardial infarction," *Eur. J. Clin Invest.* 43(9): 986-995.

Cottet, F. et al. (2003). "Recommendable Routes to Trifluoromethyl-Substituted Pyridine- and Quinolinecarboxylic Acids," *Eur. J. Org. Chem.* 1559-1568.

Couillin, I. et al. (2009). "IL-1R1/MyD88 Signaling In Critical for Elastase-Induced Lung Inflammation and Emphysema," *J Immunol* 183: 8195-8202.

Dasu, M.R. et al. (2012). "Toll-like receptors and diabetes: a therapeutic perspective," *Clinical Science* 122: 203-214.

Datta, S. et al. (2004). "Toll IL-1 Receptors Differ in Their Ability to Promote the Stabilization of Adenosine and Uridine-Rich Elements Containing mRNA," *J Immunol* 173: 2755-2761.

David, B.T. et al. (2013). "A toll-like receptor 9 antagonist reduces pain hypersensitivity and the inflammatory response in spinal cord injury," *Neurobiology of Disease* 54: 194-205.

Davidson, D.J. et al. (2006). "IRAK-4 Mutation (Q293X): Rapid Detection and Characterization of Defective Post-Transcriptional TLR/IL-1R Responses in Human Myeloid and Non-Myeloid Cells," *J. Immunol* 177:8202-8211.

Del Rey, A. et al. (2012). "Chronic neuropathic pain-like behavior and brain-borne IL-1β," *Ann. N. Y. Acad. Sci.* 1262: 101-107.

Denes, A. et al. (2013). "Central and haematopoietic interleukin-1 both contribute to ischaemic brain injury in mice," *Disease Models & Mechanisms* 6: 1043-1048.

Dinarello, C.A. (2009). "Immunological and Inflammatory Functions of the Interleukin-1 Family," *Annu. Rev. Immunol.* 27:519-550.

Dinarello, C.A. (2011). "A clinical perspective of IL-1β, as the gatekeeper of inflammation," *Eur. J. Immunol.* 41: 1203-1217.

Dispenza, M.C. et al. (2012). "Systemic isotretinoin therapy normalizes exaggerated TLF-2-mediated innate immune responses in acne patients," *J. Invest Dermatol.* 132(9): 2198-2205.

Dubaniewicz, A. (2013). "Microbial and human heat shock proteins as 'danger signals' in sarcoidosis," *Human Immunology* 74: 1550-1558.

European Pharmacopoeia 8.0 (2014). "2.9.31. Particle size analysis by laser light diffraction," 333-336.

Falck-Hansen, M. et al. (2013). "Toll-Like Receptors in Atherosclerosis," *Int. J. Mol. Sci.* 14: 14008-14023.

Fang, Y. et al. (2011). "Toll-like receptor and its roles in myocardial ischemic/reperfusion injury," *Med Sci Monit* 17(4): RA100-109.

Flannery, S. et al. (2010). "The interleukin-1 receptor-associated kinases: Critical regulators of innate immune signalling," *Biochemical Pharmacology* 80:1981-1991.

Foster, A.M. et al. (2014). "IL-36 promotes myeloid cell infiltration, activation and inflammatory activity in skin," *J Immunol.* 192(12): 6053-6061.

Freeman, C.M. et al. (2013). "Lung CD8+ T cells in COPD have increased expression of bacterial TLRs," *Respiratory Research* 14(13): 1-13.

Fresno, M. et al. (2011). "Toll-like receptors, inflammation, metabolism and obesity," *Archives of Physiology and Biochemistry* 117(3): 151-164.

Gambuzza, M. et al. (2011). "Targeting Toll-like receptors: Emerging therapeutics from multiple sclerosis management," *Journal of Neuroimmunology* 239: 1-12.

Gavara, L. et al. (2011). "Regioselective synthesis of novel substituted indazole-5,6-diamine derivatives," *Tetrahedron* 67: 1633-1639.

Gilliet, M. et al. (2004). "Psoriasis Triggered by Toll-like Receptor 7 Agonist Imiquimod in the Presence of Dermal Plasmacytoid Dendritic Cell Precursors," *Arch Dermatol* 140: 1490-1495.

Goh, F.G. et al. (2012). "Intrinsic danger: activation of Toll-like receptors in rheumatoid arthritis," *Rheumatology* 51: 7-23.

Gresnigt, M.S. et al. (2013). "Biology of IL-36 cytokines and their role in disease," *Seminars in Immunology* 25: 458-465.

Guerrero, A.T.G. et al. (2012). "Toll-like receptor 2/MyD88 signaling mediates zymosan-induced joint hypernociception in mice: Participation of TNF-α, IL-1β and CXCL1/KC," *European Journal of Pharmacology* 674: 51-57.

(56) References Cited

OTHER PUBLICATIONS

Gül, A. et al. (2012). "Interleukin-1β-regulating antibody XOMA 052 (gevokizumab) in the treatment of acute exacerbations of resistant uveitis of Behçet's disease: an open-label pilot study," *Ann Rheum Dis* 71:563-566.
Guo, H. et al. (2012). "Toll-like receptor 2 siRNA suppresses corneal inflammation and attenuates *Aspergillus fumigatus* keratitis in rats," *Immunology and Cell Biology* 90: 352-357.
Haenuki, Y. et al. (2012). "A critical role of IL-33 in experimental allergic rhinitis," *J Allergy Clin Immunol* 130(1): 184-194.
Han, P. et al. (2013). "Interleukin-33 Mediates Formalin-Induced Inflammatory Pain in Mice," *Neuroscience* 241: 59-66.
Han, Y. et al. (2013). "Associations of pri-miR-34b/c and pre-miR-196a2 Polymorphisms and Their Multiplicative Interactions with Hepatitis B Virus Mutations with Hepatocellular Carcinoma Risk," *PLOS One* 8(3): 1-9.
Hao, L-Y. et al. (2013). "Inflammasomes in inflammatory bowel disease pathogenesis," *Current Opinion* 29(4): 363-369.
Haydar, S.N. et al. (2010). "5-Cyclic Amine-3-arylsulfonylindazoles as Novel 5-$HT_6$ Receptor Antagonists," *J. Med. Chem.* 53: 2521-2527.
Heimesaat, M.M. et al. (2007). "Shift Towards Pro-inflammatory Intestinal Bacteria Aggravates Acute Murine Colitis via Toll-like Receptors 2 and 4," *PLoS One* 7: 1-7.
Henderson, C. et al. (2010). "Monogenic IL-1 Mediated Autoinflammatory and Immunodeficiency Syndromes: Finding the Right Balance in Response to Danger Signals," *Clin Immunol.* 135(2): 210-222.
Hilberath, J.N. et al. (2017). "Resolution of Toll-like receptor 4-mediated acute lung injury is linked to eicosanoids and suppressor of cytokine signaling 3," *The FASEB Journal* 25(6): 1827-1835.
Holtmann, H. et al. (2001). "The MAPK Kinase Kinase TAK1 Plays a Central Role in Coupling the Interleukin-1 Receptor to Both Transcriptional and RNA-targeted Mechanisms of Gene Regulation," *The Journal of Biological Chemistry* 276(5): 3508-3516.
Hunt, K.W. et al. (2009). "Selective Synthesis of 1-Functionalized-alkyl-1H-indazoles§," *Organic Letters* 11(21): 5054-5057.
Hynes Jr., J. et al. (2014). "Advanced in the Discovery of Small-Molecule IRAK4 Inhibitors," *Annual Reports in Medicinal Chemistry* 49: 117-133.
Imaoka, H. et al. (2008). "Interleukin-18 production and pulmonary function in COPD," *Eur Respir J.* 31: 287-297.
Jaffari, G.A. et al. (1973). "Methylation of Indazoles and Related Reactions," *Journal of the Chemical Society* 1: 2371-2374.
Jain, S.K. et al. (2012). "KF/alumina catalyzed regioselective benzylation and benzoylation using solvent-free grind-stone chemistry," *RSC Adv.* 2: 8929-8933.
Janeway, C.A. et al. (2002). "Innate Immune Recognition," *Annu. Rev. Immunol.* 20:197-216.
Jeyaseelan, S. et al. (2005). "Distinct Roles of Pattern Recognition Receptors CD14 and Toll-Like Receptor 4 in Acute Lung Injury," *Infection and Immunity* 73(3): 1754-1763.
Kaarniranta, K. et al. (2009). "Age-related macular degeneration: activation of innate immunity system via pattern recognition receptors," *J Mol Med* 87: 117-123.
Kang, M-J. et al. (2007). "IL-18 is Inducted and IL-18 Receptor α Plays a Critical Role in the Pathogenesis of Cigarette Smoke-Induced Pulmonary Emphysema and Inflammation," *J Immunol* 178: 1948-1959.
Kawayama, T. et al. (2012). "Interleukin-18 in Pulmonary Inflammatory Diseases," *Journal of Interferon & Cytokine Research* 32(10): 443-451.
Kezic, J. et al. (2011). "Endotoxin-induced uveitis is primarily dependent on radiation-resistant cells and on MyD88 but not TRIF," *Journal of Leukocyte Biology* 90(2): 305-311.
Kfoury, A. et al. (2013). "MyD88 in DNA Repair and Cancer Cell Resistance to Genotoxic Drugs," *JNCI* 105(13): 937-946.
Khan, K. N. et al. (2013). "Toll-like receptor system and endometriosis," *J. Obstet. Gynaecol. Res.* 39(8): 1281-1292.

Kim, S. et al. (2005). "Control of the Particle Properties of a Drug Substance by Crystallization Engineering and the Effect on Drug Product Formulation," *Organic Process research & Development* 9: 894-901.
Kim, T.W. et al. (2007). "A critical role for IRAK4 kinase activity in Toll-like receptor-mediated innate immunity," *JEM* 204(5):1025-1036.
Kim, D. et al. (2009). "Toll-Like Receptors in Peripheral Nerve Injury and Neuropathic Pain," *Current Topics in Microbiology and Immunology* 336: 169-186.
Kim, T.W. et al. (2011). "The critical role of IRAK4-mediated NFkB activation in modified LDL-induced atherosclerosis," *J Immunol* 186(5): 2871-2880.
Kitazawa, M. et al. (2011). "Blocking IL-1 Signaling Rescues Cognition, Attenuates Tau Pathology, and Restores Neuronal β-Catenin Pathway Function in an Alzheimer's Disease Model," *The Journal of Immunology* 187: 6539-6549.
Kobori, A. et al. (2010). "Interleukin-33 expression is specifically enhanced in inflamed mucosa of ulcerative colitis," *J. Gastroenterol* 45: 999-1007.
Kollewe, C. et al. (2004). "Sequential Autophosphorylation Steps in the Interleukin-1 Receptor-associated Kinase-1 Regulate its Availability as an Adapter in Interleukin-1 Signaling," *The Journal of Biological Chemistry* 279(7): 5227-5236.
Kovach, M.A. et al. (2011). "Toll like receptors in diseases of the lung," *International Immunopharmacology* 11: 1399-1406.
Kreisel, D. et al. (2013). "Innate immunity and organ transplantation: focus on lung transplantation," *Transpl Int.* 26(1): 2-10.
Ku, C. et al. (2007). "Selective predisposition to bacterial infections in IRAK-4-deficient children: IRAK-4-dependent TLRs are otherwise redundant in protective immunity," *JEM* 204(10):2407-2422.
Kwok, Y.H. et al. (2012). "Increased Responsiveness of Peripheral Blood Mononuclear Cells to In Vitro TLF 2, 4 and 7 Ligand Stimulation in Chronic Pain Patients," *PLOS One* 7(8): 1-8.
Kym, P.R. et al. (2006). "Screening for Cardiovascular Safety: A Structure-Activity Approach for Guiding Lead Selection of Melanin Concentrating Hormone Receptor 1 Antagonists," *J. Med. Chem.* 49: 2339-2352.
Lawson, C. et al. (2008). Abnormal interleukin 1 receptor types I and II gene expression in eutopic and ectopic endometrial tissues of women with endometriosis, *Journal of Reproductive Immunology* 77: 75-84.
Lee, H.S. et al. (2012). "Expression of Toll-like Receptor 4 Contributes to Corneal Inflammation in Experimental Dry Eye Disease," *Invest Ophthalmol Vis Sci.* 53(9): 5632-5640.
Leventhal, J.S. et al. (2012). "Toll-like receptors in transplantation: sensing and reacting to injury," *Kidney International* 81: 826-832.
Li, D. et al. (2014). "IL-33 promotes ST2-dependent lung fibrosis by the induction of alternatively activated macrophages and innate lymphoid cells in mice," *J. Allergy Clin Immunol* 134(6): 1422-1432.e11.
Li, J. et al. (2013). "Toll-like receptors as therapeutic targets for autoimmune connective tissue diseases," *Pharmacology & Therapeutics* 138: 441-451.
Liang, B. et al. (2013). "Myeloid Differentiation Factor 88 Promotes Growth and Metastasis of Human Hepatocellular Carcinoma," *Clinical Cancer Research* 19(11): 2905-2916.
Lim, J-E. et al. (2011). "MyD88 Deficiency Ameliorates β-Amyloidosis in an Animal Model of Alzheimer's Disease," *The American Journal of Pathology* 179(3): 1095-1103.
Lin, M-H. et al. (2015). "Regioselective synthesis of 2H-indazoles through Ga/Al-and Al-mediated direct alkylation reaction of indazoles," *Org. Biomol. Chem.* 13: 11376-11381.
Liu, T. et al. (2013). "New insights into the mechanisms of itch: are pain and itch controlled by distinct mechanisms?" *Pflugers Arch.* 465(12): 1-24.
Liu, X-J. et al. (2014). "Nociceptive neurons regulate innate and adaptive immunity and neuropathic pain through MyD88 adapter," *Cell Research* 24: 1374-1377.
Liu-Bryan, R. et al. (2005). "Innate Immunity Conferred by Toll-like Receptors 2 and 4 and Myeloid Differentiation Factor 88 Expression Is Pivotal to Monosodium Urate Monohydrate Crystal-Inducted Inflammation," *Arthritis & Rheumatism* 52(9): 2936-2946.

(56) References Cited

OTHER PUBLICATIONS

Lloyd, C.M. et al. (2010). "IL-33 family members and asthma—bridging innate and adaptive immune responses," *Curr Opin Immunol* 22(6): 800-806.

Luo, G. et al. (2006). "Regioselective Protection at N-2 and Derivatization at C-3 of Indazoles," *J. Org. Chem.* 71: 5392-5395.

Maekawa, Y. et al. (2009). "Survival and Cardiac Remodeling After Myocardial Infarction Are Critically Dependent on the Host Innate Immune Interleukin-1 Receptor-Associated Kinase-4 Signaling: A Regulator of Bone Marrow-Derived Dendritic Cells," *Circulation* 120: 1401-1414.

Margaritopoulous, G.A. et al. (2010). "Investigation of Toll-like receptors in the pathogenesis of fibrotic and granulomatous disorders: a bronchoalveolar lavage study," *Fibrogenesis & Tissue Repair* 3(20): 1-9.

Marminon, C. et al. (2007). "Synthesis of N-benzylated indole-, indazole- and benzotriazole-4,7-diones," *Tetrahedron* 63: 735-739.

Martínez-González, I. et al. (2013). "Human Mesenchymal Stem Cells Overexpressing the IL-33 Antagonist Soluble IL-1 Receptor-Like-1 Attenuate Endotoxin-Induced Acute Lung Injury," *Am J Respir Cell Mol Biol* 49(4): 552-562.

McGettrick, A.F. et al. (2007). "Toll-like receptors: key activators of leucocytes and regulator of haematopoiesis," *British Journal of Haematology* 139: 185-193.

Miller, L.S. (2008). "Toll-like receptors in skin," *Adv Dermatol.* 24: 71-87.

Minkis, K. et al. (2012). "Interleukin 1 Receptor Antagonist Deficiency Presenting as Infantile Pustulosis Mimicking Infantile Pustular Psoriasis," *Arch Dermatol.* 148(6): 747-752.

Motshwene, P.G. et al. (2009). "An Oligomeric Signaling Platform Formed by the Toll-like Receptor Signal Transducers MyD88 and IRAK-4," *The Journal of Biological Chemistry* 284(37):25404-25411.

Nadigel, J. et al. (2011). "Cigarette smoke increases TLR4 and TLR9 expression and induces cytokine production from $CD8^+$ T cells in chronic obstructive pulmonary disease," *Respiratory Research* 12(149): 1-13.

Nakanishi, W. et al. (2013). "IL-33, but Not IL-25, Is Crucial for the Development of House Dust Mite Antigen-Induced Allergic Rhinitis," *PLoS One* 8(10): 1-8.

Narayanan, S. et al. (2008). "Interleukin-1 Receptor-1-deficient Mice Show Attenuated Production of Ocular Surface Inflammatory Cytokines in Experimental Dry Eye," *Cornea* 27(7): 811-817.

Ngo, V.N. et al. (2011). "Oncogenically active MYD88 mutations in human lymphoma," *Nature* 470: 115-121.

Nguyen, T.M. et al. (2014). "Anti-Markovnikov Hydroamination of Alkenes Catalyzed by a Two-Component Organic Photoredox System: Direct Access to Phenethylamine Derivatives," *Angew Chem Int Ed Engl.* 53(24): 6198-6201.

Nickerson, K.M. et al. (2010). "TLR9 Regulates TLR7- and MyD88-Dependent Autoantibody Production and Disease in a Murine Model of Lupus," *J Immunol* 184: 1840-1848.

Nicotra, L. et al. (2012). "Toll-Like Receptors in Chronic Pain," *Exp Neurol.* 234(2): 316-329.

Niebuhr, M. et al. (2008). "Dysregulation of toll-like receptor-2 (TLR-2)-induced effects in monocytes from patients with atopic dermatitis: impact of the TLR-2 R753Q polymorphism," *Allergy* 63: 728-734.

Niedermann, K. et al. (2011). "A Ritter-Type Reaction: Direct Electrophilic Trifluoromethylation at Nitrogen Atoms Using Hypervalent Iodine Reagents," *Angew. Chem. Int. Ed.* 50: 1059-1063.

Noelker, C. et al. (2013). "Toll like receptor 4 mediates cell death in a mouse MPTP model of Parkinson disease," *Scientific Reports* 3(1393): 1-5.

Nordström, D. et al. (2012). "Beneficial Effect of Interleukin 1 Inhibition with Anakinra in Adult-onset Still's Disease. An Open, Randomized, Multicenter Study," *The Journal of Rheumatology* 39(10): 2008-2011.

Oyama, J. et al. (Feb. 17, 2004). "Reduced Myocardial Ischemia—Reperfusion Injury in Toll-Like Receptor 4-Deficient Mice," *Circulation* 109: 784-789.

Palit, S. et al. (2015). "Synthesis of Novel Indazole-Derived Ionic Liquids," *Synthesis* 47: 3371-3384.

Pauwels, N.S. et al. (2011). "Role of IL-1 $\alpha$ and the NIrp3/caspase-1/IL-1$\beta$ axis in cigarette smoke-induced pulmonary inflammation and COPD," *Eur Respir J* 38: 1019-1028.

Pettersson, T. et al. (2012). "Setting up TRAPS," *Annals of Medicine* 44: 109-118.

Puente, X.S. et al. (2011). "Whole-genome sequencing identifies recurrent mutations in chronic lymphocytic leukaemia," *Nature* 475: 101-105.

Qi, Y. et al. (2014). "Retinal Ischemia/Reperfusion Injury is Mediated by Toll-like Receptor 4 Activation of NLRP3 Inflammasomes," *IOVS* 55(9): 5466-5475.

Qiu, C. et al. (2012). "Anti-interleukin-33 inhibits cigarette smoke-induced lung inflammation in mice," *Immunology* 138: 76-82.

Rakoff-Nahoum, S. et al. (2006). "Role of Toll-like Receptors in Spontaneous Commensal-Dependent Colitis," *Immunity* 25: 319-329.

Ramirez Cruz, N.E.R. et al. (2004). "Toll-like receptors: dysregulation in vivo in patients with acute respiratory distress syndrome," *Revista Alergia Mexico* 51(6): 210-217.

Ramirez, S.R. et al. (2012). "Toll-like Receptors and Diabetes Complications: Recent Advances," *Current Diabetes Reviews* 8: 480-488.

Reddy, M.T. et al. (2014). "Synthesis and molecular docking studies of new substituted indazole derivatives for anti-breast cancer activity," *Der Pharma Chemica* 6(6): 411-417.

Redfern, R.L. et al. (2010). "Toll-like receptors in ocular surface disease," *Experimental Eye Research* 90: 679-687.

Rekhter, M. et al. (2008). "Genetic ablation of IRAK4 kinase activity inhibits vascular lesion formation," *Biochemical and Biophysical Research Communications* 367: 642-648.

Roger, T. et al. (2009). "Protection from lethal Gram-negative bacterial sepsis by targeting Toll-like receptor 4," *PNAS* 106(7): 2348-2352.

Ruperto, N. et al. (2012). "Two Randomized Trials of Canakinumab in Systemic Juvenile Idiopathic Arthritis," *The New England Journal of Medicine* 367(25): 2396-2406.

Salerno, L. et al. (2012). "Novel inhibitors of nitric oxide synthase with antioxidant properties," *European Journal of Medicinal Chemistry* 49: 118-126.

Saluja, R. et al. (2015). "The role of the IL-33/IL-1RL1 axis in mast cell and basophil activation in allergic disorders," *Molecular Immunology* 63: 80-85.

Santulli, P. et al. (2013). "Profibrotic interleukin-33 is correlated with uterine leiomyoma tumour burden," *Human Reproduction* 28(8): 2126-2133.

Scanzello, C.R. et al. (2008). "Innate immune system activation in osteoarthritis: is osteoarthritis a chronic wound?" *Current Opinion in Rheumatology* 20: 565-572.

Sedimbi, S.K. et al. (2013). "IL-18 in inflammatory and autoimmune disease," *Cell. Mol. Life Sci.* 70: 4795-4802.

Seki, H. et al. (2010). "Effect of Toll-like receptor 4 inhibitor on LPS-induced lung injury," *Inflamm. Res.* 59: 837-845.

Selway, J.L. et al. (2013). "Toll-like receptor 2 activation and comedogenesis: implications for the pathogenesis of acne," *BMC Dermatology* 13(10): 1-7.

Seneviratne, A.N. et al. (2012). "Toll-like receptors and macrophage activation in atherosclerosis," *Clinica Chimica Acta* 413: 3-14.

Shi, Y. et al. (2010). "Monosodium urate crystals in inflammation and immunity," *Immunological Reviews* 233: 203-217.

Shumeiko, A.E. et al. (2006). "Regioselectivity in Azoles Alkylation. Benzylation of Indazole under Conditions of the Phase-transfer Catalysis," *Russian Journal of Organic Chemistry* 42(2): 294-295.

Sikora, J. et al. (2012). "Imbalance in Cytokines from Interleukin-1 Family—Role in Pathogenesis of Endometriosis," *American Journal of Reproductive Immunology* 68: 138-145.

Slade, D.J. et al. (2009). "Indazoles: Regioselective Protection and Subsequent Amine Coupling Reactions," *J. Org. Chem.* 74: 6331-6334.

(56) References Cited

OTHER PUBLICATIONS

Souers, A.J. et al. (2005). "Identification of 2-(4-Benzyloxyphenyl)-N-[1-(20pyrrolidin-1-yl-ethyl)-1H-indazol-6-yl]acetamide, an Orally Efficacious Melanin-Concentrating Hormone Receptor 1 Antagonist for the Treatment of Obesity," *J. Med. Chem.* 48: 1318-1321.

Srivastava, R. et al. (2012). "Augmentation of Therapeutic Responses in Melanoma by Inhibition of IRAK-1,-4," *Cancer Research* 72(23): 6209-6216.

Staschke, K.A. et al. (2009). "IRAK4 kinase Activity is Required for Th17 Differentiation and Th17-mediated Disease," *J Immunol* 183(1): 568-577.

Stokes, J.A. (2013). "Toll-like receptor signaling adapter proteins govern spread of neuropathic pain and recovery following nerve injury in male mice," *Journal of Neuroinflammation* 10(148): 1-14.

Sun, Y. et al. (2009). "Inhibition of Corneal Inflammation by the TLR4 Antagonist Eritoran Tetrasodium (E5564)," *Invest Ophthalmol Vis Sci.* 50(3): 1247-1254.

Sun, Y. et al. (2014). "The Role of Interleukin-1 Receptor-Associated Kinases in Vogt-Koyanagi-Herada Disease," *PLOS ONE* 9(4): 1-8.

Suzuki, N. et al. (2002). "Severe impairment of interleukin-1 and Toll-like receptor signaling in mice lacking IRAK-4," *Nature* 416:750-754.

Talabot-Ayer, D. et al. (2014). "Immune-mediated experimental arthritis in IL-33 deficient mice," *Cytokine* 69: 68-74.

Terhorst, D. et al. (2010). "The Role of Toll-Like Receptors in Host Defenses and Their Relevance to Dermatologic Disease," *Am J. Clin Dermatol* 11(1): 1-10.

Thompson, J.A. et al. (2013). "Potential role of Toll-like receptors in programming of vascular dysfunction," *Clinical Science* 125: 19-25.

Tian, Q. et al. (2013). "A Practical Synthesis of a PI3K Inhibitor under Noncryogenic Conditions via Functionalization of Lithium Triarylmagnesiate Intermediate," *Organic Process Research & Development* 17: 97-107.

Timmers, L. et al. (2008). "Toll-Like Receptor 4 Mediates Maladaptive Left Ventricular Remodeling and Impairs Cardiac Function After Myocardial Infarction," *Circulation Research* 102: 257-264.

Treon, S.P. et al. (2012). "MYD88 L265P Somatic Mutation in Waldenström's Macroglobulinemia," *The New England Journal of Medicine* 367(9): 826-833.

Tsypin, V.G. et al. (2002). "Adamantylation of Indazole and Its C-Nitro Derivatives," *Russian Journal of Organic Chemistry* 38(1): 90-94.

Valaperti, A. et al. (2013). "Innate Immune Interleukin-1 Receptor-Associated Kinase 4 Exacerbates Viral Myocarditis by Reducing $CCR5^+CD11b^+$Monocyte Migration and Impairing Interferon Production," *Circulation* 128: 1542-1554.

Viguier, M. et al. (2010). "Successful Treatment of Generalized Pustular Psoriasis With the Interleukin-1-Receptor Antagonist Anakinra: Lack of Correlation with *IL1RN* Mutations," *Annals of Internal Medicine* 153: 66-67.

Vijmasi, T. et al. (2013). "Topical administration of interleukin-1 receptor antagonist as a therapy for aqueous-deficient dry eye in autoimmune disease," *Molecular Vision* 19: 1957-1965.

Volin, M.V. et al. (2011). "Interleukin-18: A Mediator of Inflammation and Angiogenesis in Rheumatoid Arthritis," *Journal of Interferon & Cytokine Research* 31(10): 745-781.

Walsh, D. et al. (2013). "Pattern recognition receptors—Molecular orchestrators of inflammation in inflammatory bowel disease," *Cytokine & Growth Factor Reviews* 24: 91-104.

Wan, Y.Y. et al. (2006). "The kinase TAK1 integrates antigen and cytokine receptor signaling for T cell development, survival and function," *Nature Immunology* 7(8): 851-858.

Wang, C. et al. (2001). "TAK1 is a ubiquitin-dependent kinase of MMK and IKK," *Nature* 412: 346-351.

Wang, Y-C. et al. (2013). "Toll-Like Receptor 4 Antagonist Attenuates Intracerebral Hemorrhage-Induced Brain Injury," *Stroke* 44: 2545-2552.

Wolf, G. et al. (2008). "Interleukin-1 signaling in required for induction and maintenance of postoperative incisional pain: Genetic and pharmacological studies in mice," *Brain, Behavior, and Immunity* 22: 1072-1077.

Wollina, U. et al. (2013). "Acne inversa (*Hidradenitis suppurativa*): A review with a focus on pathogenesis and treatment," *Indian Dermatology Online Journal* 4(1): 1-11.

Xiang, M. et al. (2010). "Association of Toll-Like Receptor Signaling and Reactive Oxygen Species: A Potential Therapeutic Target for Posttrauma Acute Lung Injury," *Mediators of Inflammation* 8 pages.

Yamada, A. et al. (2017). "Targeting IL-1 in Sjögren's syndrome," *Expert Opin. Ther. Targets* 17(4): 393-401.

Yang, J. et al. (2016). "Highly Efficient Synthesis of $N^1$-Substituted 1H-Indazoles by DBU-Catalyzed Aza-Michael Reaction of Indazole with Enones," *Synthesis* 48: 1139-1146.

Yap, D. Y. H. et al. (2013). "The role of cytokines in the pathogenesis on systemic lupus erythematosus—from bench to bedside," *Nephrology* 18: 243-255.

Yin, H. et al. (2012). "Adenovirus-mediated delivery of soluble ST2 attenuates ovalbumin-induced allergic asthma in mice," *Clinical & Experimental Immunology*170: 1-9.

Zambrano-Zaragoza, J.F. et al. (2014). "Th17 Cells in Autoimmune and Infectious Diseases," *International Journal of Inflammation* 1-12.

Zhao, J. et al. (2013). "Spinal Interleukin-33 and its Receptor ST2 Contribute to Bone Cancer-Induced Pain in Mice," *Neuroscience* 253: 172-182.

Zhu, F-G. et al. (2013). "A novel antagonist of Toll-like receptors 7, 8 and 9 suppresses lupus disease-associated parameters in NZBW/F1 mice," *Autoimmunity* 45(7): 419-428.

Moco, S. et al. (2007). "Metabolomics technologies and metabolite identification," Trends in Analytical Chemistry, 26(9): 855-866.

Schlosser, M. et al. (2003). "The Direct Metaliation and Subsequent Functionalization of Trifluoromethyl-Substituted Pyridines and Quinolines," Eur. J. Org. Chem., 1569-1575.

Seganish (2016). "Inhibitors of interleukin-1 receptor-associated kinase 4 (IRAK4): a patent review (2012-2015)," Expert Opinion on Therapeutic Patents, 26(8): 917-932.

U.S. Appl. No. 15/570,212, filed Oct. 27, 2017, for Bothe et al. (Also published as US20180289685, cited herewith) (U.S. Patent Application is not submitted herewith pursuant to the waiver of 37 C.F.R. § 1.98(a)(2)(iii) issued by the Office on Sep. 21, 2004.).

U.S. Appl. No. 16/081,209, filed Aug. 30, 2018, for Bothe et al. (Also published as US20190071432, cited herewith) (U.S. Patent Application is not submitted herewith pursuant to the waiver of 37 C.F.R. § 1.98 (a)(2)(iii) issued by the Office on Sep. 21, 2004.).

U.S. Appl. No. 16/097,065, filed Oct. 26, 2018, for Thaler et al. (Also published as US20190106407, cited herewith) (U.S. Patent Application is not submitted herewith pursuant to the waiver of 37 C.F.R. § 1.98 (a)(2)(iii) issued by the Office on Sep. 21, 2004.).

U.S. Appl. No. 16/097,067, filed Oct. 26, 2018, for Thaler et al. (Also published as US20190112270, cited herewith) (U.S. Patent Application is not submitted herewith pursuant to the waiver of 37 C.F.R. § 1.98 (a)(2)(iii) issued by the Office on Sep. 21, 2004.).

U.S. Appl. No. 16/097,463, filed Oct. 29, 2018, for Thaler et al. (Also published as US20190144420, cited herewith) (U.S. Patent Application is not submitted herewith pursuant to the waiver of 37 C.F.R. § 1.98 (a)(2)(iii) issued by the Office on Sep. 21, 2004.).

U.S. Appl. No. 16/306,235, filing date unknown, inventor not yet available. (U.S. Patent Application is not submitted herewith purusant to the waiver of 37 C.F.R. § 1.98(a)(2)(iii) issued by the Office on Sep. 21, 2004.).

U.S. Appl. No. 16/306,506, filed May 24, 2017, for Rausch et al. (Also published as US20190125736, cited herewith) (U.S. Patent Application is not submitted herewith pursuant to the waiver of 37 C.F.R. § 1.98 (a)(2)(iii) issued by the Office on Sep. 21, 2004).

U.S. Appl. No. 16/377,025, filed Apr. 5, 2019, for Bothe et al. (U.S. Patent Application is not submitted herewith pursuant to the waiver of 37 C.F.R. § 1.98(a)(2)(iii) issued by the Office on Sep. 21, 2004.).

(56) References Cited

OTHER PUBLICATIONS

U.S. Appl. No. 16/428,669, filed May 31, 2019, for Bothe et al. (U.S. Patent Application is not submitted herewith pursuant to the waiver of 37 C.F.R. § 1.98(a)(2)(iii) issued by the Office on Sep. 21, 2004.).

\* cited by examiner

DSC- and TGA-Thermogram of anhydrate of compound (I)

Microscopic images of crystalline particles of (I) obtained via recrystallization analogous to the recrystallization protocol described in example #5 variant #1 compared to crystalline particles of (I) obtained analogous to the recrystallization described in example #5, variant #3

| Crystals obtained via "linear addition of water, analogously to example #5 variant #1 | Crystals obtained via addition of water according to a "cubic dosing curve", analogously to example #5 variant #3 |
|---|---|
|  |  |
|  |  |

Pictures were recorded using a Zeiss Axioscope 2 microscope equipped with a Zeiss AxioCam ICc 5.

*FIG. 7*

CRYSTALLINE FORMS OF N-[2-(3-HYDROXY-3-METHYLBUTYL)-6-(2-HYDROXYPROPAN-2-YL)-2H-INDAZOL-5-YL]-6-(TRIFLUOROMETHYL)PYRIDINE-2-CARBOXAMIDE

CROSS REFERENCE TO RELATED APPLICATIONS

This application is a national stage application under 35 U.S.C. § 371 of International Application No. PCT/EP2017/059764, filed internationally on Apr. 25, 2017, which claims the benefit of European Application Nos. 16167649.9, filed Apr. 29, 2016, and 16167650.7, filed Apr. 29, 2016.

The present invention relates to crystalline forms of N-[2-(3-Hydroxy-3-methylbutyl)-6-(2-hydroxypropan-2-yl)-2H-indazol-5-yl]-6-(trifluoromethyl)pyridine-2-carboxamide, processes for its preparation, pharmaceutical compositions comprising it, intermediate compounds, and to their use in the control of disorders.

N-[2-(3-Hydroxy-3-methylbutyl)-6-(2-hydroxypropan-2-yl)-2H-indazol-5-yl]-6-(trifluoromethyl)-pyridine-2-carboxamide corresponds to the compound of formula (I):

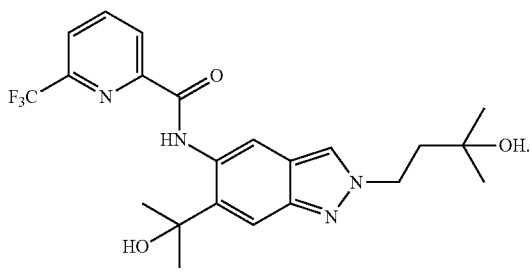

(I)

The compound of formula (I) in a hydrate form inhibits interleukin-1 receptor-associated kinase 4 (IRAK4).

BACKGROUND

Human IRAK4 (interleukin-1 receptor-associated kinase 4) plays a key role in the activation of the immune system. Therefore, this kinase is an important therapeutic target molecule for the development of inflammation-inhibiting substances. IRAK4 is expressed by a multitude of cells and mediates the signal transduction of Toll-like receptors (TLR), except TLR3, and receptors of the interleukin (IL)-1β family consisting of the IL-1R (receptor), IL-18R, IL-33R and IL-36R (Janeway and Medzhitov, Annu. Rev. Immunol., 2002; Dinarello, Annu. Rev. Immunol., 2009; Flannery and Bowie, Biochemical Pharmacology, 2010).

Neither IRAK4 knockout mice nor human cells from patients lacking IRAK4 react to stimulation by TLRs (except TLR3) and the IL-1β family (Suzuki, Suzuki, et al., Nature, 2002; Davidson, Currie, et al., The Journal of Immunology, 2006; Ku, von Bernuth, et al., JEM, 2007; Kim, Staschke, et al., JEM, 2007).

The binding of the TLR ligands or the ligands of the IL-1β family to the respective receptor leads to recruitment and binding of MyD88 [Myeloid differentiation primary response gene (88)] to the receptor. As a result, MyD88 interacts with IRAK4, resulting in the formation of an active complex which interacts with and activates the kinases IRAK1 or IRAK2 (Kollewe, Mackensen, et al., Journal of Biological Chemistry, 2004; Precious et al., J. Biol. Chem., 2009). As a result of this, the NF (nuclear factor)-kB signalling pathway and the MAPK (mitogen-activated protein kinase) signal pathway is activated (Wang, Deng, et al., Nature, 2001). The activation both of the NF-kB signalling pathway and of the MAPK signalling pathway leads to processes associated with different immune processes. For example, there is increased expression of various inflammatory signal molecules and enzymes such as cytokines, chemokines and COX-2 (cyclooxygenase-2), and increased mRNA stability of inflammation-associated genes, for example COX-2, IL-6, IL-8 (Holtmann, Enninga, et al., Journal of Biological Chemistry, 2001; Datta, Novotny, et al., The Journal of Immunology, 2004). Furthermore, these processes may be associated with the proliferation and differentiation of particular cell types, for example monocytes, macrophages, dendritic cells, T cells and B cells (Wan, Chi, et al., Nat Immunol, 2006; McGettrick and J. O'Neill, British Journal of Haematology, 2007).

The central role of IRAK4 in the pathology of various inflammatory disorders had already been shown by direct comparison of wild-type (WT) mice with genetically modified animals having a kinase-inactivated form of IRAK4 (IRAK4 KDKI). IRAK4 KDKI animals have an improved clinical picture in the animal model of multiple sclerosis, atherosclerosis, myocardial infarction and Alzheimer's disease (Rekhter, Staschke, et al., Biochemical and Biophysical Research Communication, 2008; Maekawa, Mizue, et al., Circulation, 2009; Staschke, Dong, et al., The Journal of Immunology, 2009; Kim, Febbraio, et al., The Journal of Immunology, 2011; Cameron, Tse, et al., The Journal of Neuroscience, 2012). Furthermore, it was found that deletion of IRAK4 in the animal model protects against virus-induced myocarditis an improved anti-viral reaction with simultaneously reduced systemic inflammation (Valaperti, Nishii, et al., Circulation, 2013). It has also been shown that the expression of IRAK4 correlates with the degree of Vogt-Koyanagi-Harada syndrome (Sun, Yang, et al., PLoS ONE, 2014).

As well as the essential role of IRAK4 in congenital immunity, there are also hints that IRAK4 influences the differentiation of what are called the Th17 T cells, components of adaptive immunity. In the absence of IRAK4 kinase activity, fewer IL-17-producing T cells (Th17 T cells) are generated compared to WT mice. The inhibition of IRAK4 is therefore suitable for prophylaxis and/or treatment of atherosclerosis, type 1 diabetes, rheumatoid arthritis, spondyloarthritis, lupus erythematosus, psoriasis, vitiligo, chronic inflammatory bowel disease and viral disorders, for example HIV (human immunodeficiency virus), hepatitis virus (Staschke, et al., The Journal of Immunology, 2009; Zambrano-Zaragoza, et al., International Journal of Inflammation, 2014).

Owing to the central role of IRAK4 in the MyD88-mediated signal cascade of TLRs (except TLR3) and the IL-1 receptor family, the inhibition of IRAK4 can be utilized for the prophylaxis and/or treatment of disorders mediated by the receptors mentioned. TLRs and also components of the IL-1 receptor family are involved in the pathogenesis of rheumatoid arthritis, metabolic syndrome, diabetes, osteoarthritis, Sjögren syndrome and sepsis (Scanzello, Plaas, et al. Curr Opin Rheumatol, 2008; Roger, Froidevaux, et al, PNAS, 2009; Gambuzza, Licata, et al., Journal of Neuroimmunology, 2011; Fresno, Archives Of Physiology And Biochemistry, 2011; Volin and Koch, J Interferon Cytokine Res, 2011; Akash, Shen, et al., Journal of Pharmaceutical Sciences, 2012; Goh and Midwood, Rheumatology, 2012; Dasu, Ramirez, et al., Clinical Science, 2012; Ramirez and Dasu, Curr Diabetes Rev, 2012; Li, Wang, et al., Pharmacology & Therapeutics, 2013; Sedimbi, Hagglof, et al., Cell Mol Life Sci, 2013; Talabot-Aye, et al., Cytokine, 2014). Skin diseases such as psoriasis, atopic dermatitis, Kindler's syndrome, allergic contact dermatitis, acne inversa and acne vulgaris are associated with the IRAK4-mediated TLR signalling pathway (Gilliet, Conrad, et al., Archives of Dermatology, 2004; Niebuhr, Langnickel, et al., Allergy, 2008; Miller, Adv Dermatol, 2008; Terhorst, Kalali, et al., Am J Clin Dermatol, 2010; Viguier, Guigue, et al., Annals of Internal Medicine, 2010; Cevikbas, Steinhoff, J Invest Dermatol, 2012; Minkis, Aksentijevich, et al., Archives of Dermatology, 2012; Dispenza, Wolpert, et al., J Invest Dermatol, 2012; Minkis, Aksentijevich, et al., Archives of Dermatology, 2012; Gresnigt and van de Veerdonk, Seminars in Immunology, 2013; Selway, Kurczab, et al., BMC Dermatology, 2013; Sedimbi, Hagglof, et al., Cell Mol Life Sci, 2013; Wollina, Koch, et al. Indian Dermatol Online, 2013; Foster, Baliwag, et al., The Journal of Immunology, 2014).

Pulmonary disorders such as pulmonary fibrosis, obstructive pulmonary disease (COPD), acute respiratory distress syndrome (ARDS), acute lung injury (ALI), interstitial lung disease (ILD), sarcoidosis and pulmonary hypertension also show an association with various TLR-mediated signalling pathways. The pathogenesis of the pulmonary disorders may be either infectiously mediated or non-infectiously mediated processes (Ramirez Cruz, Maldonado Bernal, et al., Rev Alerg Mex, 2004; Jeyaseelan, Chu, et al., Infection and Immunity, 2005; Seki, Tasaka, et al., Inflammation Research, 2010; Xiang, Fan, et al., Mediators of Inflammation, 2010; Margaritopoulos, Antoniou, et al., Fibrogenesis & Tissue Repair, 2010; Hilberath, Carlo, et al., The FASEB Journal, 2011; Nadigel, Prefontaine, et al., Respiratory Research, 2011; Kovach and Standiford, International Immunopharmacology, 2011; Bauer, Shapiro, et al., Mol Med, 2012; Deng, Yang, et al., PLoS One, 2013; Freeman, Martinez, et al., Respiratory Research, 2013; Dubaniewicz, A., Human Immunology, 2013). TLRs and also IL-1R family members are also involved in the pathogenesis of other inflammatory disorders such as Behçet's disease, gout, lupus erythematosus, adult-onset Still's disease and chronic inflammatory bowel diseases such as ulcerative colitis and Crohn's disease, and transplant rejection, and so inhibition of IRAK4 here is a suitable therapeutic approach (Liu-Bryan, Scott, et al., Arthritis & Rheumatism, 2005; Christensen, Shupe, et al., Immunity, 2006; Cario, Inflammatory Bowel Diseases, 2010; Nickerson, Christensen, et al., The Journal of Immunology, 2010; Rakoff-Nahoum, Hao, et al., Immunity, 2006; Heimesaat, Fischer, et al., PLoS ONE, 2007; Kobori, Yagi, et al., J Gastroenterol, 2010; Shi, Mucsi, et al., Immunological Reviews, 2010; Leventhal and Schroppel, Kidney Int, 2012; Chen, Lin, et al., Arthritis Res Ther, 2013; Hao, Liu, et al., Curr Opin Gastroenterol, 2013; Kreisel and Goldstein, Transplant International, 2013; Li, Wang, et al., Pharmacology & Therapeutics, 2013; Walsh, Carthy, et al., Cytokine & Growth Factor Reviews, 2013; Zhu, Jiang, et al., Autoimmunity, 2013; Yap and Lai, Nephrology, 2013). Because of the mechanism of action of the compound of formula (I), they are also suitable for prophylactic and/or therapeutic use of the TLR and IL-1R family-mediated disorders endometriosis and atherosclerosis (Akoum, Lawson, et al., Human Reproduction, 2007; Allhorn, Boing, et al., Reproductive Biology and Endocrinology, 2008; Lawson, Bourcier, et al., Journal of Reproductive Immunology, 2008; Seneviratne, Sivagurunathan, et al., Clinica Chimica Acta, 2012; Sikora, Mielczarek-Palacz, et al., American Journal of Reproductive Immunology, 2012; Falck-Hansen, Kassiteridi, et al., International Journal of Molecular Sciences, 2013; Khan, Kitajima, et al., Journal of Obstetrics and Gynaecology Research, 2013; Santulli, Borghese, et al., Human Reproduction, 2013; Sedimbi, Hagglof, et al., Cell Mol Life Sci, 2013).

In addition to the disorders already mentioned, IRAK4-mediated TLR processes have been described in the pathogenesis of eye disorders such as retinal ischaemia, keratitis, allergic conjunctivitis, keratoconjunctivitis sicca, macular degeneration and uveitis (Kaarniranta and Salminen, J Mol Med (Berl), 2009; Sun and Pearlman, Investigative Ophthalmology & Visual Science, 2009; Redfern and McDermott, Experimental Eye Research, 2010; Kezic, Taylor, et al., J Leukoc Biol, 2011; Chang, McCluskey, et al., Clinical & Experimental Ophthalmology, 2012; Guo, Gao, et al., Immunol Cell Biol, 2012; Lee, Hattori, et al., Investigative Ophthalmology & Visual Science, 2012; Qi, Zhao, et al., Investigative Ophthalmology & Visual Science, 2014).

Because of the central role of IRAK4 in TLR-mediated processes, the inhibition of IRAK4 also enables the treatment and/or prevention of cardiovascular and neurological disorders, for example myocardial reperfusion damage, myocardial infarction, hypertension (Oyama, Blais, et al., Circulation, 2004; Timmers, Sluijter, et al., Circulation Research, 2008; Fang and Hu, Med Sci Monit, 2011; Bijani, International Reviews of Immunology, 2012; Bomfim, Dos Santos, et al., Clin Sci (Lond), 2012; Christia and Frangogiannis, European Journal of Clinical Investigation, 2013; Thompson and Webb, Clin Sci (Lond), 2013), and also Alzheimer's disease, stroke, craniocerebral trauma and Parkinson's disease (Brough, Tyrrell, et al., Trends in Pharmacological Sciences, 2011; Carty and Bowie, Biochemical Pharmacology, 2011; Denes, Kitazawa, Cheng, et al., The Journal of Immunology, 2011; Lim, Kou, et al., The American Journal of Pathology, 2011; Béraud and Maguire-Zeiss, Parkinsonism & Related Disorders, 2012; Denes, Wilkinson, et al., Disease Models & Mechanisms, 2013; Noelker, Morel, et al., Sci. Rep., 2013; Wang, Wang, et al., Stroke, 2013).

Because of the involvement of TLR signals and IL-1 receptor family-mediated signals via IRAK4 in the case of pruritus and pain, for example cancer pain, post-operative pain, inflammation-induced and chronic pain, there may be assumed to be a therapeutic effect in the indications mentioned through the inhibition of IRAK4 (Wolf, Livshits, et al., Brain, Behavior, and Immunity, 2008; Kim, Lee, et al., Toll-like Receptors: Roles in Infection and Neuropathology, 2009; del Rey, Apkarian, et al., Annals of the New York Academy of Sciences, 2012; Guerrero, Cunha, et al., European Journal of Pharmacology, 2012; Kwok, Hutchinson, et al., PLoS ONE, 2012; Nicotra, Loram, et al., Experimental Neurology, 2012; Chopra and Cooper, J Neuroimmune Pharmacol, 2013; David, Ratnayake, et al., Neurobiology of Disease, 2013; Han, Zhao, et al., Neuroscience, 2013; Liu and Ji, Pflugers Arch., 2013; Stokes, Cheung, et al., Journal of Neuroinflammation, 2013; Zhao, Zhang, et al., Neuroscience, 2013; Liu, Y. Zhang, et al., Cell Research, 2014).

This also applies to some oncological disorders. Particular lymphomas, for example ABC-DLBCL (activated B-cell diffuse large-cell B-cell lymphoma), mantle cell lymphoma and Waldenström's disease, and also chronic lymphatic leukaemia, melanoma and liver cell carcinoma, are characterized by mutations in MyD88 or changes in MyD88 activity which can be treated by an IRAK4 inhibitor (Ngo, Young, et al., Nature, 2011; Puente, Pinyol, et al., Nature, 2011; Srivastava, Geng, et al., Cancer Research, 2012; Treon, Xu, et al., New England Journal of Medicine, 2012; Choi, Kim, et al., Human Pathology, 2013; (Liang, Chen, et al., Clinical Cancer Research, 2013). In addition, MyD88 plays an important role in ras-dependent tumours, and so IRAK4 inhibitors are also suitable for treatment thereof (Kfoury, A., K. L. Corf, et al., Journal of the National Cancer Institute, 2013).

Inflammatory disorders such as CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome; FMF (familial mediterranean fever), HIDS (hyper-IgD syndrome), TRAPS (tumour necrosis factor receptor 1-associated periodic syndrome), juvenile idiopathic arthritis, adult-onset Still's disease, Adamantiades-Behçet's disease, rheumatoid arthritis, osteoarthritis, keratoconjunctivitis sicca and Sjögren syndrome are treated by blocking the IL-1 signal pathway; therefore here, too, an IRAK4 inhibitor is suitable for treatment of the diseases mentioned (Narayanan, Corrales, et al., Cornea, 2008; Henderson and Goldbach-Mansky, Clinical Immunology, 2010; Dinarello, European Journal of Immunology, 2011; Gul, Tugal-Tutkun, et al., Ann Rheum Dis, 2012; Pettersson, Annals of MedicinePetterson, 2012; Ruperto, Brunner, et al., New England Journal of Medicine, 2012; Nordström, Knight, et al., The Journal of Rheumatology, 2012; Vijmasi, Chen, et al., Mol Vis, 2013; Yamada, Arakaki, et al., Opinion on Therapeutic Targets, 2013). The ligand of IL-33R, IL-33, is involved particularly in the pathogenesis of acute kidney failure, and so the inhibition of IRAK4 for prophylaxis and/or treatment is a suitable therapeutic approach (Akcay, Nguyen, et al., Journal of the American Society of Nephrology, 2011). Components of the IL-1 receptor family are associated with myocardial infarction, different pulmonary disorders such as asthma, COPD, idiopathic interstitial pneumonia, allergic rhinitis, pulmonary fibrosis and acute respiratory distress syndrome (ARDS), and so prophylactic and/or therapeutic action is to be expected in the indications mentioned through the inhibition of IRAK4 (Kang, Homer, et al., The Journal of Immunology, 2007; Imaoka, Hoshino, et al., European Respiratory Journal, 2008; Couillin, Vasseur, et al., The Journal of Immunology, 2009; Abbate, Kontos, et al., The American Journal of Cardiology, 2010; Lloyd, Current Opinion in Immunology, 2010; Pauwels, Bracke, et al., European Respiratory Journal, 2011; Haenuki, Matsushita, et al., Journal of Allergy and Clinical Immunology, 2012; Yin, Li, et al., Clinical & Experimental Immunology, 2012; Abbate, Van Tassell, et al., The American Journal of Cardiology, 2013; Alexander-Brett, et al., The Journal of Clinical Investigation, 2013; Bunting, Shadie, et al., BioMed Research International, 2013; Byers, Alexander-Brett, et al., The Journal of Clinical Investigation, 2013; Kawayama, Okamoto, et al., J Interferon Cytokine Res, 2013; Martinez-González, Roca, et al., American Journal of Respiratory Cell and Molecular Biology, 2013; Nakanishi, Yamaguchi, et al., PLoS ONE, 2013; Qiu, Li, et al., Immunology, 2013; Li, Guabiraba, et al., Journal of Allergy and Clinical Immunology, 2014; Saluja, Ketelaar, et al., Molecular Immunology, 2014).

The prior art discloses a multitude of IRAK4 inhibitors (see, for example, Annual Reports in Medicinal Chemistry (2014), 49, 117-133).

U.S. Pat. No. 8,293,923 and US20130274241 disclose IRAK4 inhibitors having a 3-substituted indazole structure.

WO2013106254 and WO2011153588 disclose 2,3-disubstituted indazole derivatives.

WO2007091107 describes 2-substituted indazole derivatives for the treatment of Duchenne muscular dystrophy. The compounds disclosed do not have 6-hydroxyalkyl substitution.

WO2015/091426 describes indazoles, the alkyl group thereof substituted at position 2 by a carboxamide structure.

WO2015/104662 disclose indazole compound of formula (I),

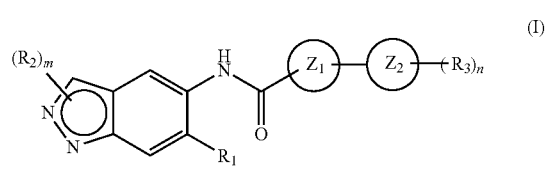

which are therapeutically useful as kinase inhibitor, particularly IRAK4 inhibitors, and pharmaceutically acceptable salts or stereoisomers thereof that are useful in the treatment and prevention of diseases or disorder, in particular their use in diseases or disorder mediated by kinase enzyme, particularly IRAK4 enzyme.

WO2016/083433, published after the priority date of the present application, describes novel substituted indazoles of the following formula

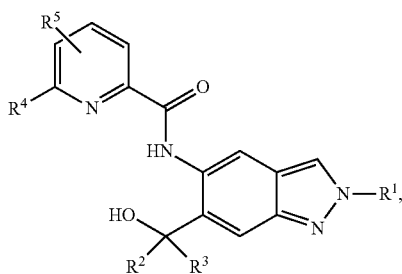

methods for the production thereof, use thereof alone or in combinations to treat and/or prevent diseases, and use thereof to produce drugs for treating and/or preventing diseases, in particular for treating and/or preventing endometriosis and endometriosis-associated pain and other symptoms associated with endometriosis such as dysmenorrhea, dyspareunia, dysuria, and dyschezia, lymphomas, rheumatoid arthritis, spondyloarthritides (in particular psoriatic spondyloarthritis and Bekhterev's disease), lupus erythematosus, multiple sclerosis, macular degeneration, COPD, gout, fatty liver diseases, insulin resistance, tumor diseases, and psoriasis.

Accordingly, a need exists for crystalline forms of the compound of formula (I) with superior physiochemical properties that may be used advantageously in pharmaceutical processing and pharmaceutical compositions.

BRIEF SUMMARY

The novel IRAK4 inhibitor shall be especially suitable for treatment and for prevention of proliferative and inflammatory disorders characterized by an overreacting immune system. Particular mention should be made here of inflammatory skin disorders, cardiovascular disorders, lung disorders, eye disorders, autoimmune disorders, gynaecological disorders, especially endometriosis, and cancer.

A process was to be disclosed that would allow the production of indazole (I) on technical scale with special focus on the following requirements:
Scale-up/scalability of the manufacturing process
High regioselectivity in the N2-alkylation reaction
Process safety
Speed of production
Ready availability of commercial starting materials
Avoidance of chromatographic separation and purification steps
Final processing via crystallization
Final adjustment of the polymorphic modification using class 3 solvents (in accordance with FDA guidelines)

Remarkably, a process could be disclosed that meets all of the requirements mentioned above.

DESCRIPTION OF THE FIGURES

FIG. 7 shows microscopic images of crystalline particles of compound (I) obtained via recrystallization.

DETAILED DESCRIPTION

Figure 1:
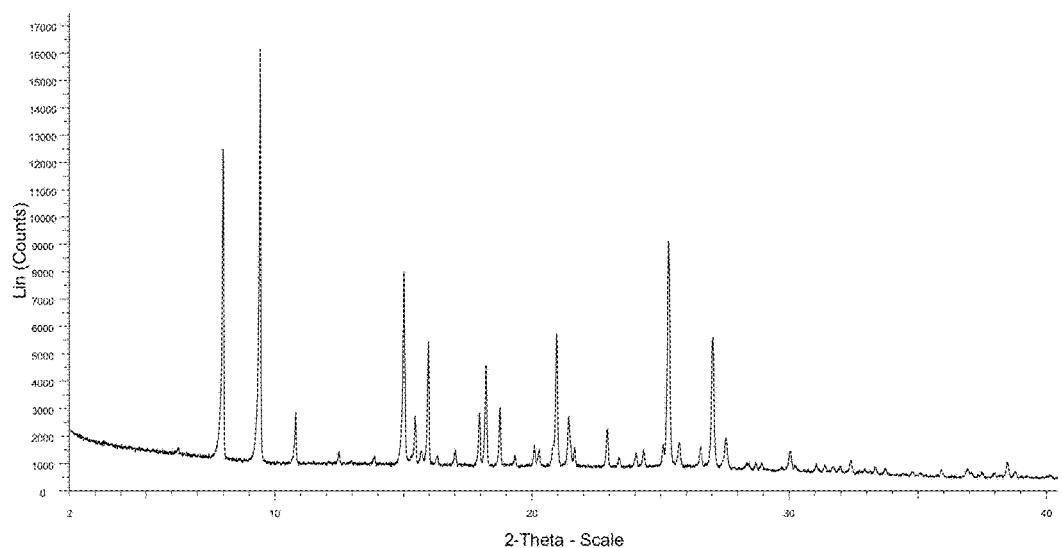
FIG. 1 shows an X-Ray powder diffractogram of the hydrate of compound (I).

Surprisingly the following crystalline forms of the compound of formula (I) have been identified, which are a hydrate, an anhydrate and a formamide solvate. In addition, the amorphous form exists. All together, the polymorphic forms, the pseudo-polymorphic forms and the amorphous form are different solid forms of the compound of formula (I).

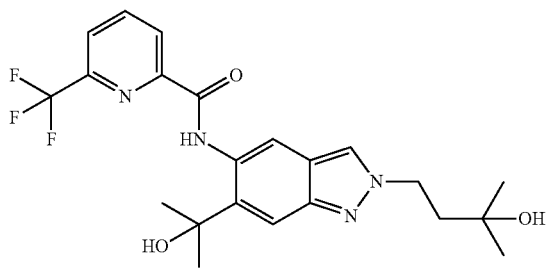

(I)

Surprisingly the hydrate of the compound of formula (I) shows beneficial properties over the other solid forms of the compound of formula (I), which are for example but not limited to stability (e.g. thermodynamic stability, mechanical stability, chemical stability, and/or storage stability), compatibility over other ingredients, purity, hygroscopicity, solubility (thermodynamical and/or kinetical), crystallization properties, habitus, bioavailability, adverse effects, pharmacokinetic behaviour, efficacy, beneficial properties during the chemical synthesis (e.g. regarding work-up or isolation which can be for example improved filterability) and/or beneficial properties during the manufacturing of a pharmaceutical composition.

The hydrate is therefore suitable for use in the pharmaceutical field, in particular suitable for manufacturing pharmaceutical compositions, for example manufacturing of tablets containing the hydrate of the compound of the formula (I).

The compound of the formula (I) in hydrate form can be isolated by evaporation of a solution of the compound of the formula (I) in Pyridin, THF, Picolin, Acetonitril, Methanol, Ethanol, 1-Propanol, Aceton, Ethylacetat, and 2-Picolin.

In addition to the hydrate, an anhydrate and a formamid solvate of the compound of formula I occur during crystallization experiments.

The compound of the formula (I) in anhydrate form can be isolated by evaporation of a solution of the compound of the formula (I) in isobutanol, 1-butanol, tetrahydrofuran/water (95/5% ww).

The compound of the formula (I) in formamid solvate form can be isolated by stirring in formamid.

Embodiments of the present invention are not only each single crystalline form of the compound of the formula (I) which are the hydrate, the anhydrate nd the formamid solvae of the compound of the formula (I) but also mixtures comprising two or three crystalline forms of the aforementioned.

A pharmaceutical composition according to the present invention comprises a crystalline form of the compound of the formula (I) selected from the group consisting of its hydrate, its anhydrate, its formamid solvate, and a mixture thereof and further pharmaceutically acceptable excipients.

A pharmaceutical composition according to the present invention comprises preferably only one of the crystalline forms selected from the group comprising the hydrate, anhydrate and the formamid solvate of the compound of formula (I) mainly and no significant fractions of another form of the compound of the formula (I). More preferably, the pharmaceutical composition contains more than 85 percent by weight, more preferably more than 90 percent by weight, most preferably more than 95 percent by weight, of the hydrate of the compound of formula (I) related to the total amount of all forms of the compound of the formula (I) present in the composition.

Preference is given to a pharmaceutical composition comprising the compound of the formula (I) in the hydrate form mainly and no significant fractions of another solid form of the compound of the formula (I), for example of another polymorphic or pseudopolymorphic form of the compound of the formula (I). The pharmaceutical composition preferably contains more than 85 percent by weight, more preferably more than 90 percent by weight, more preferably more than 95 percent by weight, of the compound of the formula (I) in the hydrate form related to the total amount of all forms of the compound of the formula (I) present in the composition.

Further preference is given to a pharmaceutical composition comprising the compound of the formula (I) in the anhydrate form mainly and no significant fractions of another solid form of the compound of the formula (I), for example of another polymorphic or pseudopolymorphic form of the compound of the formula (I). The pharmaceutical composition preferably contains more than 85 percent by weight, more preferably more than 90 percent by weight, more preferably more than 95 percent by weight, of the compound of the formula (I) in the anhydrate form related to the total amount of all forms of the compound of the formula (I) present in the composition.

Further preference is given to a pharmaceutical composition comprising the compound of the formula (I) in the formamid solvate form mainly and no significant fractions of another solid form of the compound of the formula (I), for example of another polymorphic or pseudopolymorphic form of the compound of the formula (I). The pharmaceutical composition preferably contains more than 85 percent by weight, more preferably more than 90 percent by weight, more preferably more than 95 percent by weight, of the compound of the formula (I) in the formamid solvate form related to the total amount of all forms of the compound of the formula (I) present in the composition.

The different forms of the compound of formula (I) can be distinguished by X-ray powder diffraction, differential scanning calorimetry (DSC), IR-, Raman-, NIR-, FIR- and $^{13}$C-solid-state-NMR-spectroscopy.

The different forms of the compound of formula (I) have been characterized by X-ray powder diffraction, DSC- and TGA-Thermogram:

FIG. 1: X-Ray powder diffractogram of the hydrate of compound (I)

Figure 2:
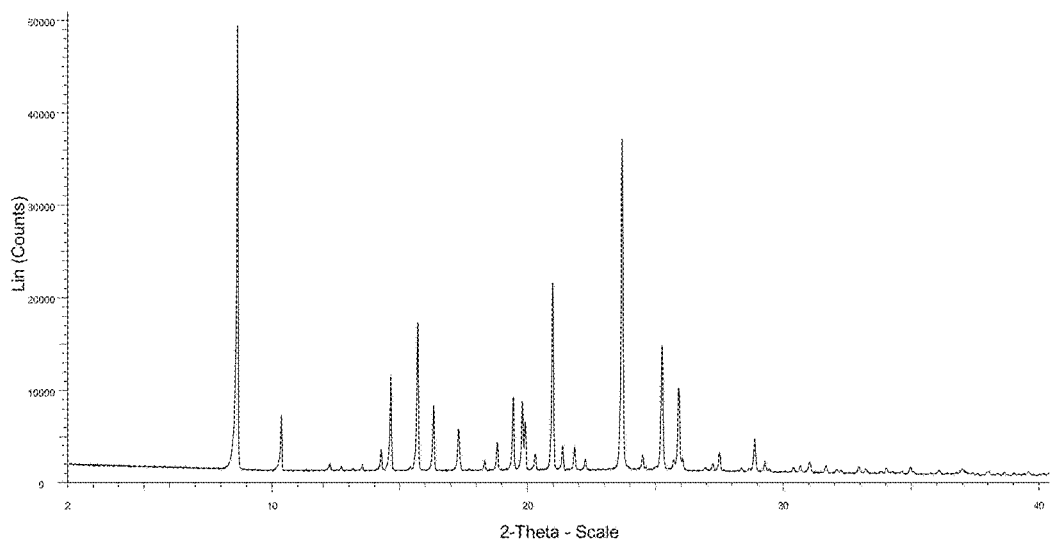
FIG. 2 shows an X-Ray powder diffractogram of the anhydrate of compound (I).

FIG. 2: X-Ray powder diffractogram of the anhydrate of compound (I)

Figure 3:
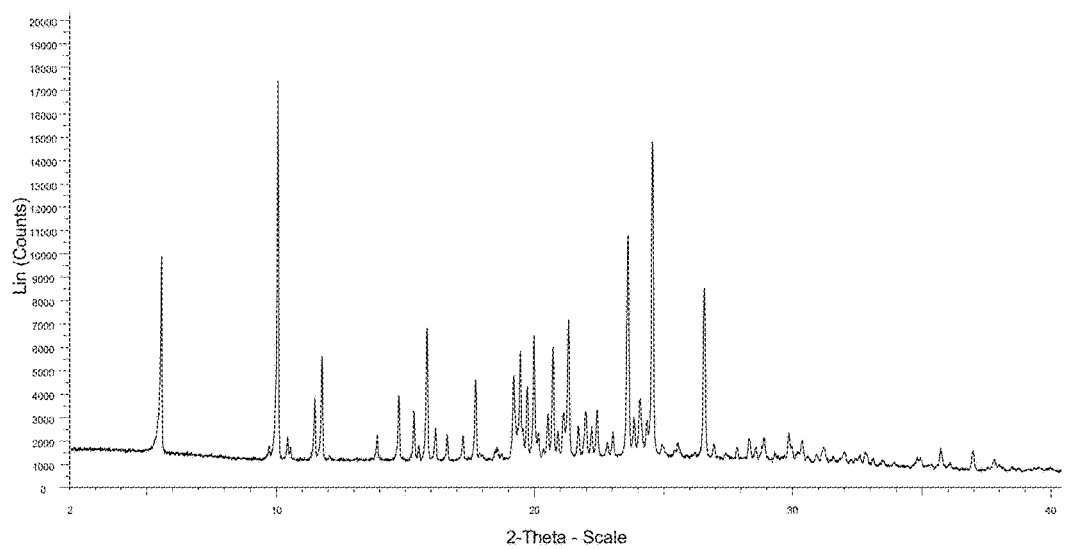
FIG. 3 shows an X-Ray powder diffractogram of the formamide solvate of compound (I).

FIG. 3: X-Ray powder diffractogram of the formamide solvate of compound (I)

Figure 4:
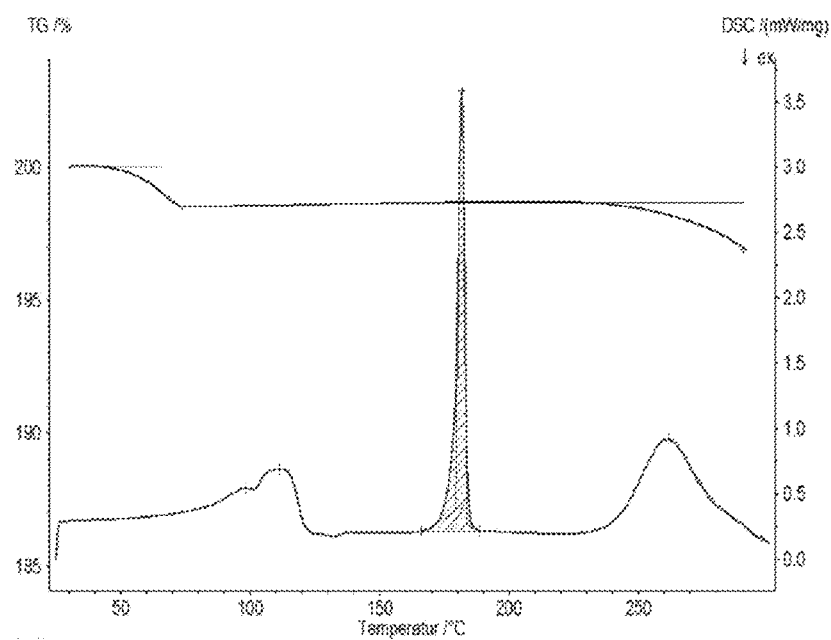
FIG. 4 shows a DSC- and TGA-Thermogram of the hydrate of compound (I).

FIG. 4: DSC- and TGA-Thermogram of the hydrate of compound (I)

Figure 5:
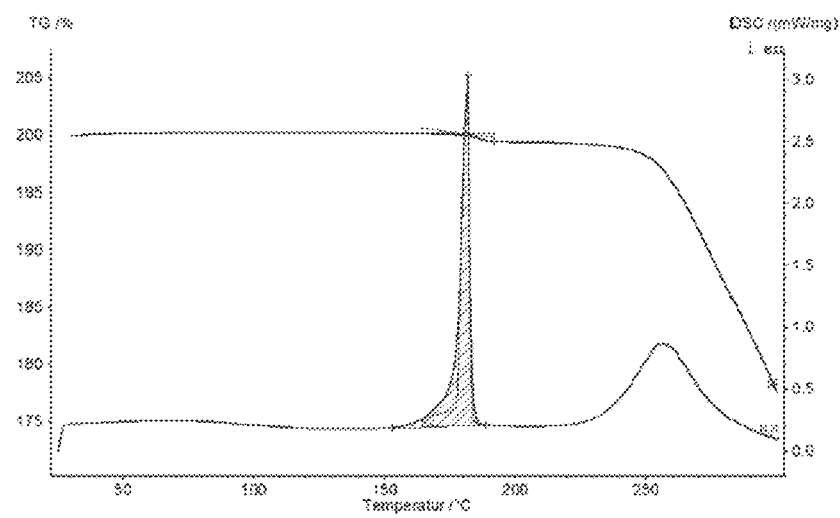
FIG. 5 shows a DSC- and TGA-Thermogram of the anhydrate of compound (I).

FIG. 5: DSC- and TGA-Thermogram of the anhydrate of compound (I)

Figure 6:
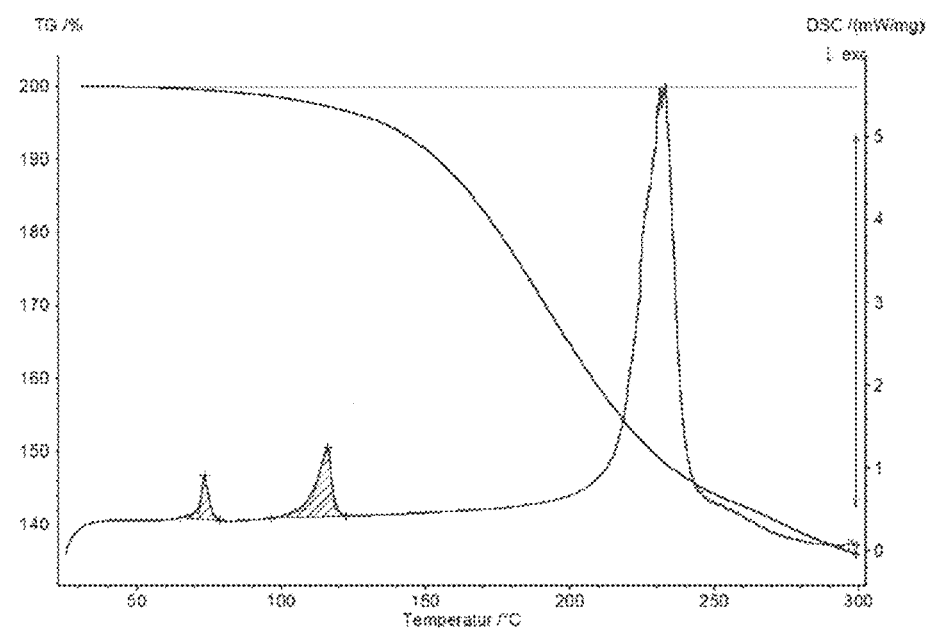
FIG. 6 shows a DSC- and TGA-Thermogram of the formamide solvate.

FIG. 6: DSC- and TGA-Thermogram of the formamide solvate

The hydrate of the compound of formula (I) can be characterized unambiguously by a X-Ray powder diffractogram (at 25° C. and with Cu-K alpha 1 as radiation source) which displays at least the following reflections: 9.4, 10.8, 15.0, preferably at least the following reflections: 9.4, 10.8, 15.0, 16.0, 17.0, more preferably at least the following reflections: 9.4, 10.8, 15.0, 16.0, 17.0, 20.1, 22.9, most preferably at least the following reflections: 9.4, 10.8, 15.0, 16.0, 17.0, 20.1, 22.9, 24.3, 26.6, 29.8, each quoted as 2Theta value ±0.2°. The hydrate of compound of formula (I) can also be characterized unambiguously by the X-Ray powder diffractogram (at 25° C. and with Cu-K alpha 1 as radiation source) as shown in FIG. 1.

The anhydrate of the compound of formula (I) can be characterized unambiguously by a X-Ray powder diffractogram (at 25° C. and with Cu-K alpha 1 as radiation source) which displays at least the following reflections: 8.6, 10.3, 14.6, preferably at least the following reflections: 8.6, 10.3, 14.6, 17.3, 19.8, more preferably at least the following reflections: 8.6, 10.3, 14.6, 17.3, 19.8, 22.2, 23.7, most preferably at least the following reflections: 8.6, 10.3, 14.6, 17.3, 19.8, 22.2, 23.7, 24.5, 25.9, 29.3, each quoted as 2Theta value ±0.2°. The anhydrate of compound of formula (I) can also be characterized unambiguously by the X-Ray powder diffractogram (at 25° C. and with Cu-K alpha 1 as radiation source) as shown in FIG. 2.

The formamid solvate of the compound of formula (I) can be characterized unambiguously by a X-Ray powder diffractogram (at 25° C. and with Cu-K alpha 1 as radiation source) which displays at least the following reflections: 5.5, 10.0, 11.5, preferably at least the following reflections: 5.5, 10.0, 11.5, 11.7, 20.7, 21.3, more preferably at least the following reflections: 5.5, 10.0, 11.5, 11.7, 20.7, 21.3, 23.6, 24.6, most preferably at least the following reflections: 5.5, 10.0, 11.5, 11.7, 20.7, 21.3, 23.6, 24.6, 26.6, each quoted as 2Theta value ±0.2°. The formamid solvate of the compound of formula (I) can also be characterized unambiguously by the X-Ray powder diffractogram (at 25° C. and with Cu-K alpha 1 as radiation source) as shown in FIG. 3.

Process for Preparing:

Preparations of N2-substituted indazoles have been described in the literature, e.g. M.-H. Lin, H.-J. Liu, W.-C. Lin, C.-K. Kuo, T.-H. Chuang, *Org. Biomol. Chem.* 2015, 13, 11376. These procedures, however, have considerable disadvantages rendering them unsuitable for technical scale. It is possible to selectively prepare N2-substituted indazoles via complex sequences of synthetic steps, which involve no direct alkylation step. These sequences, however, are long and tedious and involve considerable losses ultimately resulting in a low total yield. Therefore, synthetic routes which allow a direct preparation of N2-substituted indazoles from 1H-indazole precursors via direct and selective alkylation at N2 are most interesting. At the attempt of directly alkylating the 1H-indazole precursor of the generic formula (II) generally a mixture made up of the N1-(III) and N2-alkylated (Ia) regioisomers is obtained.

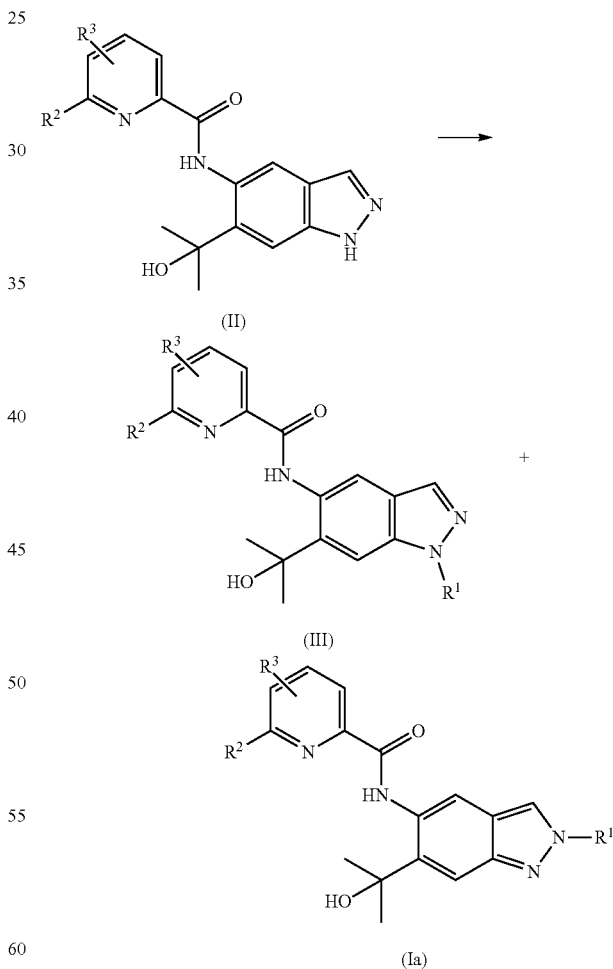

Indazole and its derivatives, a typical class of aromatic N-heterocycles, have sparked significant interest in synthetic and medicinal chemistry due to their diverse biological activities. Furthermore, diverse heterocyclic structures could be accessed from indazole-derived N-heterocyclic carbenes.

Among indazoles, N1/N2-substituted indazoles are widely used as anticancer, anti-inflammatory, anti-HIV, and antimicrobial drugs. Generally, the synthesis of N2-substituted indazoles involves cyclization procedures from miscellaneous starting materials. Unfortunately, general methodologies remain scarce in the literature. Therein, only moderate yields were obtained.

With respect to the current state of technology, several publications are known and will be discussed in the following section. None of the published procedures feature reaction conditions that lead to a direct N2-selective alkylation using a highly functionalized indazole of type (II) along with an alkyl tosylate or halide bearing an alcoholic group of type (IV) as alkylating agent.

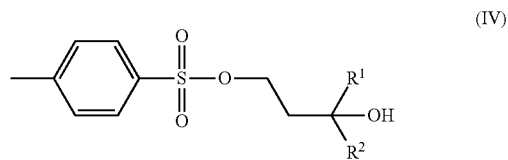
(IV)

The selectivities and/or yields are low. The problem of the prior art procedures consists in the limited functional group tolerance. Thus, only relatively simple alkylating agents bearing no labile and/or reactive functional groups apart from the leaving group are used. These agents are mostly attached to the respective 1H-indazole via nucleophilic substitution of their halides, triflates, tosylates, or mesylates. When more functionalized moieties are used, yield and selectivity decrease dramatically. In the following section, the reasons are presented why these prior art procedures are not applicable to the challenge at hand:

1. WO 2011/043479: The reactions are carried out in THF at reflux. This does not work for the case at hand (alkylating agents of type (IV)). The preparation of the corresponding triflate from e.g. the alcohol is not possible, as its decomposition occurs instantly. In addition, only a simple substrate with no functionality in the side-chain was used.

2. S. R. Baddam, N. U. Kumar, A. P. Reddy, R. Bandichhor, *Tetrahedron Lett.* 2013, 54, 1661: Only simple indazoles without functional groups were used in the reaction. Only methyl trichloroacetimidate was used as alkylating agent. Attempts to transfer acid-catalyzed conditions to selective alkylation using a functionalized alcoholic alkylating agent as depicted by (IV) at position 2 of an indazole core structure failed. This procedure cannot easily be scaled up.

3. Q. Tian, Z. Cheng, H. H. Yajima, S. J. Savage, K. L. Green, T. Humphries, M. E. Reynolds, S. Babu, F. Gosselin, D. Askin, *Org. Process Res. Dev.* 2013, 17, 97: The preparation of a THP-ether with preference for N2 of the indazole is presented. This reaction proceeds via a different mechanism and does not represent a general method, since the THP-ether product cannot be easily converted further. Furthermore, selective methods for protection of indazoles using p-methoxybenzyl derivatives under acidic conditions are presented. Attempts to transfer these conditions to selective alkylation using a functionalized alcoholic alkylating agent as depicted by (IV) at position 2 of an indazole core structure failed.

4. D. J. Slade, N. F. Pelz, W. Bodnar, J. W. Lampe, P. S. Watson, *J. Org. Chem.* 2009, 74, 6331: THP-ether and PMB-protection using acidic conditions (PPTS: pyridinium para-toluenesulfonate); attempts to transfer these conditions to selective alkylation using a functionalized alcoholic alkylating agent as depicted by (IV) at position 2 of an indazole core structure failed.

5. M. Cheung, A. Boloor, J. A. Stafford, *J. Org. Chem.* 2003, 68, 4093: Highly reactive and highly carcinogenic Meerwein-salts were used as alkylating agents. This method only comprises simple non-functionalized ethyl and methyl Meerwein salts. The reaction proceeds in polar ethyl acetate at ambient temperature. These conditions cannot be transferred to selective alkylation using a functionalized alcoholic alkylating agent as depicted by (IV) at position 2 of an indazole core structure.

Scheme 1: N-alkylation of 1H-indazoles

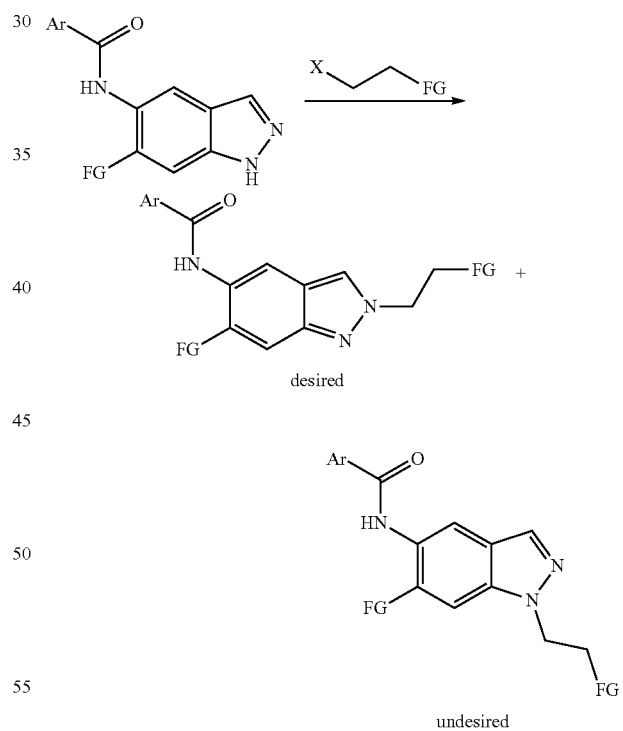

Scheme 2: N-alkylation methods of indazoles known from prior art

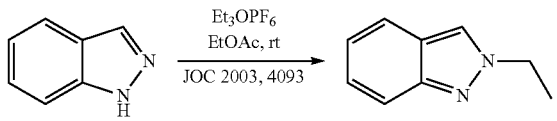

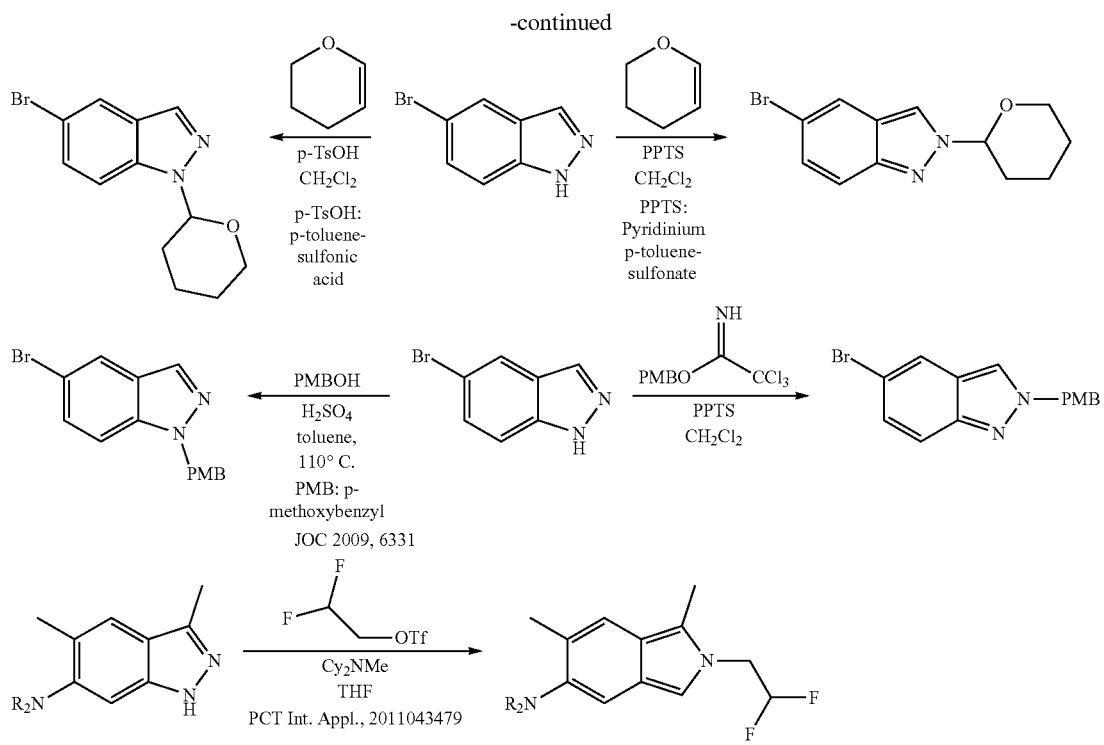

6. M.-H. Lin, H.-J. Liu, W.-C. Lin, C.-K. Kuo, T.-H. Chuang, *Org. Biomol. Chem.* 2015, 13, 11376: The procedure is N2-selective, however, it cannot be scaled up with Ga and Al metal used in stoichiometric amounts. Under the described reaction conditions Broensted acids are formed which react with the corresponding metals to give hydrogen gas. Only relatively simple substrates are used as alkylating agents. When more functionalized substrates were used, a significant decrease in yield was observed. Attempts to transfer these conditions to selective alkylation using a functionalized alcoholic alkylating agent as depicted by (IV) at position 2 of an indazole core structure failed.

7. G. Luo, L. Chen, G. Dubowchick, *J. Org. Chem.* 2006, 71, 5392: 2-(Trimethylsilyl)ethoxymethyl chloride (SEM-Cl) in THF was used for substitution on N2 of indazoles. Attempts to transfer these conditions to selective alkylation using a functionalized alcoholic alkylating agent as depicted by (IV) at position 2 of an indazole core structure failed. The corresponding products described in this publication are ethers and are not related to our target molecule. The use of highly carcinogenic 2-(trimethylsilyl)ethoxymethyl chloride (SEM-Cl) as well as benzyloxymethyl chloride (BOM-Cl) does not represent a scalable option for obtaining the target compound.

8. A. E. Shumeiko, A. A. Afon'kin, N. G. Pazumova, M. L. Kostrikin, *Russ. J. Org. Chem.* 2006, 42, 294: Only very simple substrates were used in this method. No significant selectivity is reported. A slight preference for N1-alkylation at the indazole was observed.

9. G. A. Jaffari, A. J. Nunn, *J. Chem. Soc. Perkin* 1 1973, 2371: Very simple substrates and only methylation agents were used. A more complex substrate as e.g. a combination of formaldehyde with protonated methanol resulted in only N1-substituted product (ether).

10. V. G. Tsypin et al., *Russ. J. Org. Chem.* 2002, 38, 90: The reaction proceeds in sulfuric acid and chloroform. These conditions cannot be transferred to 2-substituted indazoles. Only conversions of simple indazoles with adamanthyl alcohol as sole alkylating agent are described.

11. S. K. Jains et al. *RSC Advances* 2012, 2, 8929: This publication contains an example of N-benzylation of indazoles with low selectivity towards N1-substitution. This KF-/alumina-catalyzed method cannot be applied to 2-substituted indazoles. Attempts to transfer these conditions to selective alkylation using a functionalized alcoholic alkylating agent as depicted by (IV) at position 2 of an indazole core structure failed.

12. L. Gavara et al. *Tetrahedron* 2011, 67, 1633: Only relatively simple substrates were used. The described acidic THP-ether formation and benzylation in refluxing THF are not applicable to our substrate. Attempts to transfer these conditions to selective alkylation using a functionalized alcoholic alkylating agent as depicted by (IV) at position 2 of an indazole core structure failed.

13. M. Chakrabarty et al. *Tetrahedron* 2008, 64, 6711: N2-alkylation was observed but N1-alkylated product was obtained preferentially. The described conditions of using aqueous sodium hydroxide and phase transfer catalyst in THF are not suitable to achieve selective alkylation at position 2 of 1H-indazoles. Attempts to transfer these conditions to our system (IV)/(II) failed.

14. M. T. Reddy et al. *Der Pharma Chemica* 2014, 6, 411: The reaction proceeds in the corresponding alkylating agent as solvent. Only the use of highly reactive ethyl bromoacetate as alkylating agent is reported. There are no data on the selectivity. These conditions are not applicable to compounds as 2-indazoles. Attempts to transfer these conditions to selective alkylation using a functionalized alcoholic alkylating agent as depicted by (IV) at position 2 of an indazole core structure failed.

15. S. N. Haydar et al. *J. Med. Chem.* 2010, 53, 2521: Only simple non-functionalized alkyl groups are described (methyl, isopropyl, isobutyl). Cesium carbonate was used as base and the reaction resulted in a mixture of N1- and N2-alkylated products. These conditions are not are not suitable to achieve selective alkylation at position 2 of 1H-indazoles. Attempts to transfer these conditions to selective alkylation using a functionalized alcoholic alkylating agent as depicted by (IV) at position 2 of an indazole core structure failed.

16. Zh. V. Chirkova et al. *Russ. J. Org. Chem.* 2012, 48, 1557: In this method, relatively simple substrates are converted with potassium carbonate as base in DMF. Mixtures of N1- and N2-alkylated products are obtained. The conditions are not suitable to achieve selective alkylation at position 2 of 1H-indazoles. Attempts to transfer these conditions to selective alkylation using a functionalized alcoholic alkylating agent as depicted by (IV) at position 2 of an indazole core structure failed.

17. C. Marminon et al. *Tetrahedron* 2007, 63, 735: The ortho-substituent R in position 7 at the indazole directs the alkylation towards N2 via shielding N1 from electrophilic attacks. The conditions, sodium hydride as base in THF, are not suitable to achieve selective alkylation at position 2 of 1H-indazoles and preferentially result in alkylation at N1 in absence of a substituent in position 7 of the indazole. Attempts to transfer these conditions to selective alkylation using a functionalized alcoholic alkylating agent as depicted by (IV) at position 2 of an indazole core structure failed.

18. D. A. Nicewicz et al. *Angew. Chem. Int. Ed.* 2014, 53, 6198: Only simple substrates were used. This method describes a photochemical reaction that cannot easily be scaled up and is not applicable to a general selective, direct alkylation of 1H-indazoles at position 2. Very specific styrene derivatives are used under radical reaction conditions. Attempts to transfer these conditions to selective alkylation using a functionalized alcoholic alkylating agent as depicted by (IV) at position 2 of an indazole core structure failed.

19. Togni et al. *Angew. Chem. Int. Ed.* 2011, 50, 1059: This publication solely describes a special type of substituent (hypervalent iodine as trifluoromethylation reagent in combination with acetonitrile). This special case is not general and cannot be applied to the synthesis of N2-alkylated indazoles of type (Ia) or (Va).

20. L. Salerno et al. *European J. Med. Chem.* 2012, 49, 118: This publication describes the conversion of indazoles in an α-bromoketone melt. The reaction conditions cannot be transferred to the direct and selective synthesis of N2-alkylated indazoles of type (I). Attempts to transfer these conditions to selective alkylation using a functionalized alcoholic alkylating agent as depicted by (IV) at position 2 of an indazole core structure failed.

21. K. W. Hunt, D. A. Moreno, N. Suiter, C. T. Clark, G. Kim, *Org. Lett.* 2009, 11, 5054: This publication essentially describes an N1-selective alkylation method with addition of different bases. Simple substrates were used. Attempts to transfer these conditions to selective alkylation using a functionalized alcoholic alkylating agent as depicted by (IV) at position 2 of an indazole core structure failed.

22. J. Yang et al. *Synthesis* 2016, 48, 1139: This publication describes an N1-selective base-catalyzed aza-Michael reaction. No substitution at N2 was observed. Attempts to transfer these conditions to selective alkylation using a functionalized alcoholic alkylating agent as depicted by (IV) at position 2 of an indazole core structure failed.

23. P. R. Kym et al. *J. Med. Chem.* 2006, 49, 2339: Essentially N1-alkylations are described. Attempts to transfer these conditions to selective alkylation using a functionalized alcoholic alkylating agent as depicted by (IV) at position 2 of an indazole core structure failed.

24. A. J. Souers et al. *J. Med. Chem.* 2005, 48, 1318: This publication describes the use of potassium carbonate as base. This method proceeds mainly with preference for substitution at N1 and is therefore not suitable to achieve selective alkylation at position 2 of 1H-indazoles. Attempts to transfer these conditions to selective alkylation using a functionalized alcoholic alkylating agent as depicted by (IV) at position 2 of an indazole core structure failed.

25. P. Bethanamudi et al. *E-Journal of Chemistry* 2012, 9, 1676: The use of ionic liquids along with potassium carbonate as base results in mixtures of N1- and N2-alkylated indazoles with low yields. The selectivity shows a tendency towards substitution at N1. The use of ionic liquid cannot be transferred to our system. Attempts to transfer these conditions to selective alkylation using a functionalized alcoholic alkylating agent as depicted by (IV) at position 2 of an indazole core structure failed.

26. S. Palit et al. *Synthesis* 2015, 3371: The reaction described herein is essentially non-selective with a slight preference of substitution at N1 of the indazole. Only simple, non-functionalized alkyl groups were used. Sodium hydride and similarly strong bases were used. Attempts to transfer these conditions to selective alkylation using a functionalized alcoholic alkylating agent as depicted by (IV) at position 2 of an indazole core structure failed.

It was shown that the compound of formula (I) as well as its precursor (V) can be synthesized analogously to methods previously published in the literature via e.g. direct alkylation with 4-bromo-2-methylbutan-2-ol using potassium carbonate as base along with potassium iodide in DMF.

(V)

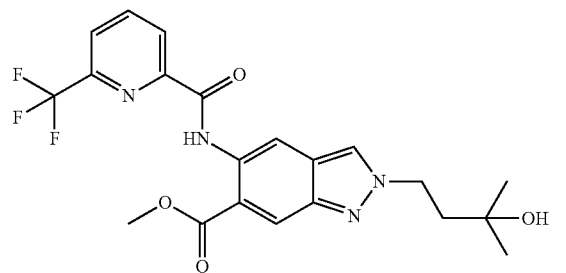

However, a mixture of N1- and N2-alkylated products was obtained with a preference for the N1-regioisomer (N1:N2=ca. 2:1). Desired N2-alkylated indazole (V) could also be obtained in a low yield as described in WO2016/083433, published after the priority date of the present application, as described in the following reaction procedure:

930 mg (2.55 mmol) of methyl 5-({[6-(trifluoromethyl) pyridin-2-yl]carbonyl}amino)-1H-indazole-6-carboxylate (VIIa), 1.06 g of potassium carbonate and 212 mg of potassium iodide were initially charged in 9 ml of DMF and the mixture was stirred for 15 min. Then 0.62 ml of 4-bromo-2-methylbutan-2-ol was added and the mixture was stirred at 60° C. overnight. The mixture was mixed with water and extracted twice with ethyl acetate, and the extract was washed three times with saturated sodium chloride solution, filtered and concentrated. Column chromatography purification on silica gel (hexane/ethyl acetate) gave 424 mg (37%) of the title compound (V). Desired N2-alkylated indazole of formula (I) was obtained in an even lower yield from (IIa), as described in the following reaction procedure:

A mixture of 500 mg (1.37 mmol) of N-[6-(2-hydroxypropan-2-yl)-1H-indazol-5-yl]-6-(trifluoromethyl)pyridine-2-carboxamide (IIa), 569 mg of potassium carbonate and 114 mg of potassium iodide in 5 ml of DMF was stirred at room temperature for 15 min. 344 mg (1.5 equivalents) of 4-bromo-2-methylbutan-2-ol were added and the mixture was heated to 100° C. for 2 h. Another 0.5 equiv. of 4-bromo-2-methylbutan-2-ol was added and the mixture was stirred at room temperature overnight. The mixture was mixed with water and extracted twice with ethyl acetate, and the combined organic phases were washed with saturated sodium chloride solution and filtered through a hydrophobic filter and concentrated. The residue was purified by column chromatography purification on silica gel (hexane/ethyl acetate). This gave 100 mg of a product fraction which was stirred with diethyl ether. The solid was filtered and dried. 60 mg of the title compound (I) were obtained. Total yield: 160 mg (26%).

Consumptive preparative HPLC proved indispensable for an efficient separation of the N1-/N2-regioismers. This new inventive process aims at an increase in the efficiency of the synthesis for scale-up and at a facilitation of the purifications of (I) and (V) via achieving better selectivity in the alkylation reactions in favour of substitution at N2 as well as at establishing a safe process for the production and handling of 3-hydroxy-3-methylbutyl 4-methylbenzenesulfonate (VI), which is prone to decomposition at higher temperatures and under the influence of acid and base. Also, highly flammable solvents, such as diethyl ether, which are not suitable for large scale preparations must be avoided.

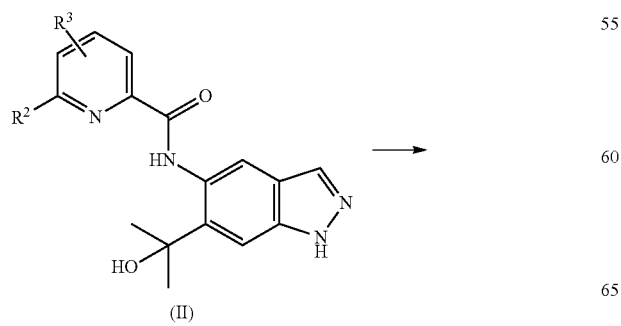

(VI)

The present invention provides a process for preparing compounds of the general formula (Ia) from either direct N2-selective alkylation of compounds of the general formula (II) or via N2-selective alkylation of compounds of the general formula (VII) resulting in intermediates of the general formula (Va) which are converted in a final synthetic step to compounds of the general formula (Ia) via addition of methylmagnesium halide.

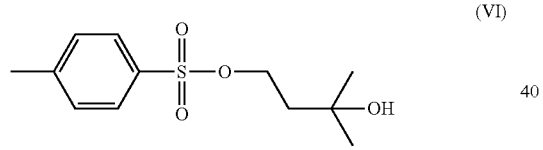

(II)

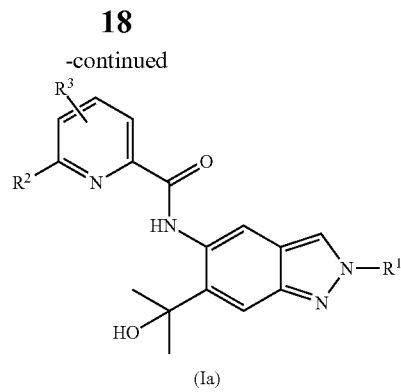

(Ia)

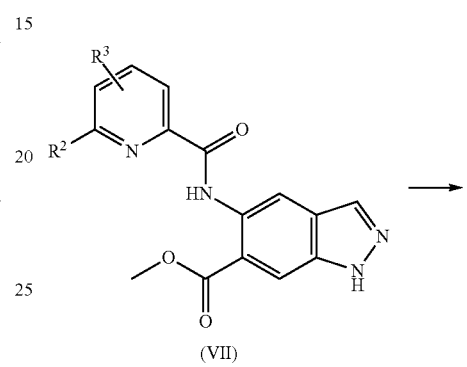

(VII)

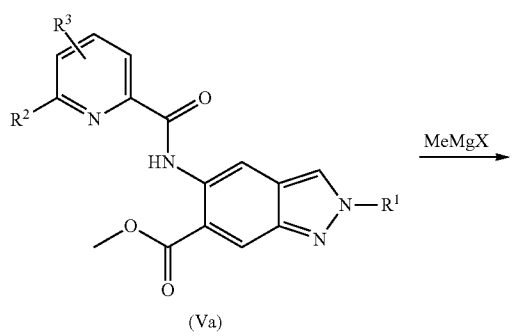

(Va)

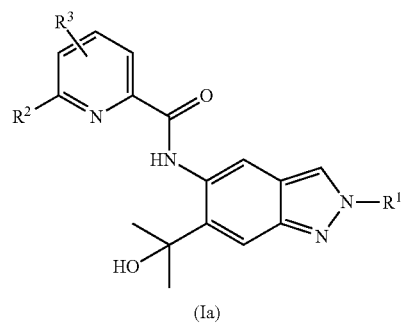

(Ia)

in which $R^1$ is

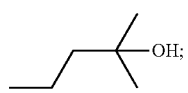

R² is difluoromethyl, trifluoromethyl or methyl; and
R³ is hydrogen, alkyl or fluorine;
X is F, Cl, Br or I
with preferably R²=trifluoromethyl and R³=H and X=Cl:

bearing a reactive functional group are unprecedented and therefore highly inventive. Upon reaction of compounds of the general formula (II) or (VII) with 3-hydroxy-3-methyl-butyl 4-methylbenzenesulfonate (VI) in a hydrocarbon sol-

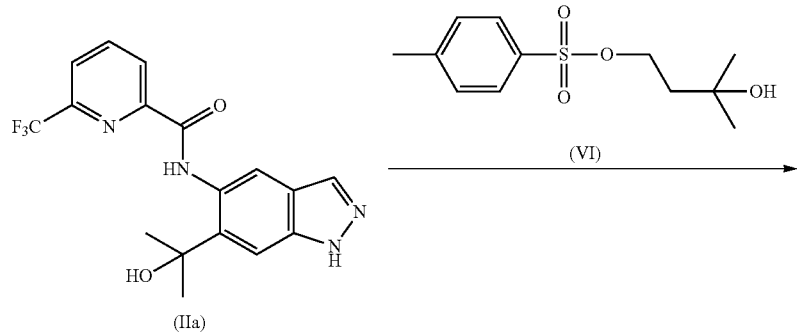

(IIa)

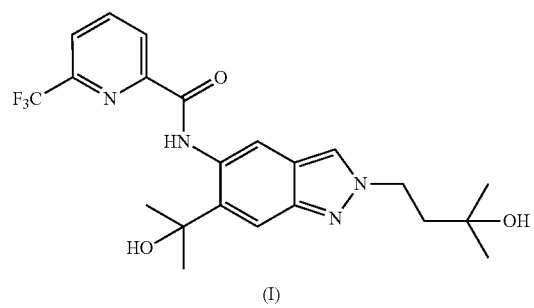

(I)

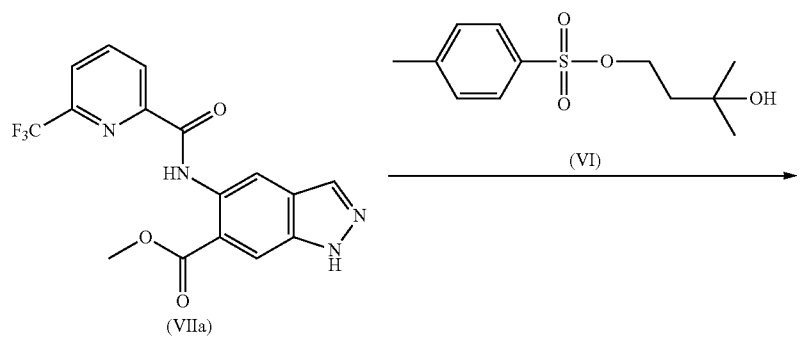

(VIIa)

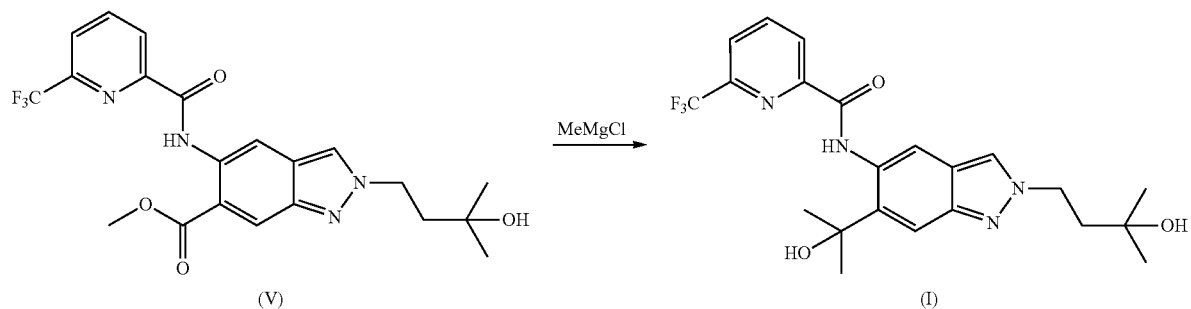

Unexpectedly, we found that the use of 3-hydroxy-3-methylbutyl 4-methylbenzenesulfonate (VI) along with N,N-diisopropylethylamine as base in toluene resulted in highly N2-selective alkylation reactions for indazoles (V) and (IIa). The N2-selectivities in these alkylation reactions of complexly functionalized indazoles with an alkyl tosylate vent, such as toluene, xylene or chlorobenzene, with addition of an organic base, such as N,N-diisopropylethylamine or triethylamine, the desired N2-isomers (I) and (V) are obtained with very high selectivities. Surprisingly, the selectivity in the alkylation reaction of (IIa) with (VI) was even higher than that observed in the alkylation of (VIIa).

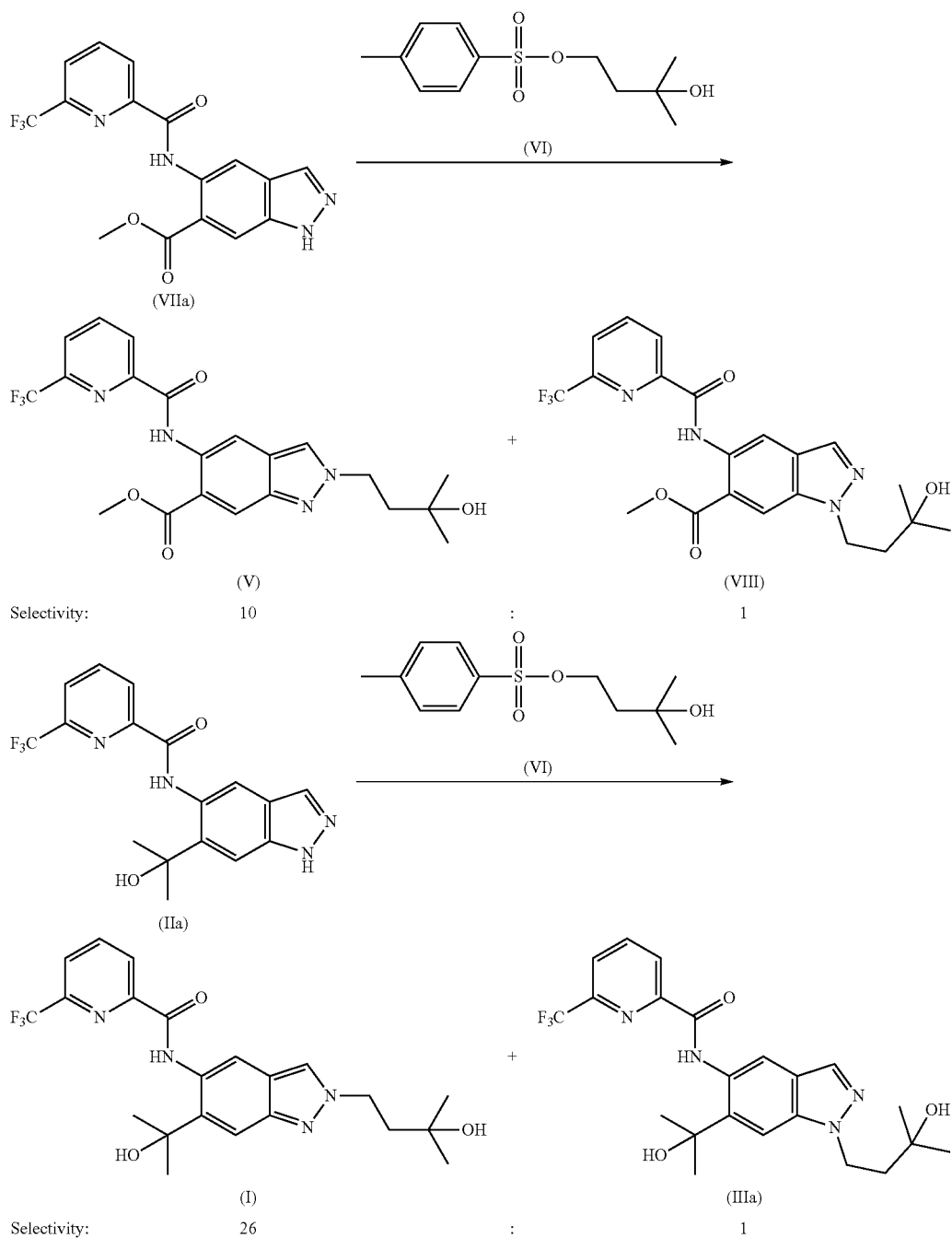

Selectivity: (V) 10 : (VIII) 1

Selectivity: (I) 26 : (IIIa) 1

Remarkably, the conversion of the starting indazole to the desired N2-alkylated product was much higher for (IIa) than (VIIa). Thus, the HPLC ratios of N2-alkylated product to starting indazole at the end of the reaction was only less than 3:1 for (V):(VIIa) and 30:1 for (I):(IIa) (HPLC). Interestingly, we observed that the reaction could be well performed via slow simultaneous addition of an organic base and a solution of an alkylating agent in unpolar hydrocarbon solvent, such as toluene, xylene or chlorobenzene. It proved beneficial to have a (slight) excess of base at each time point during the reaction. Another method works via slow addition of a solution of the alkylating agent in an unpolar solvent, such as toluene, xylene or chlorobenzene, to a mixture of the starting 1H-indazole and an excess of organic base (N,N-dicyclohexylamine or triethylamine, preferably N,N-diisopropylethyl-amine) in the aforementioned solvent (toluene or xylene) at elevated temperature (>100° C.). The reaction of (VIIa) to (V) worked best when 21 equiv. of base (N,N-dicyclohexylamine or triethylamine, preferably N,N-diisopropylethylamine) were used. A mixture of indazole (VIIa) and base in toluene (6.5 volumes) was heated to 100-110° C. In order to ensure a safe process, 5 equiv. of 3-hydroxy-3-methylbutyl 4-methylbenzenesulfonate (VI) are added to the reaction mixture as a solution in 1 volume toluene over a period of 10 h. After complete addition, the reaction is stirred for additional 12-18 hours, (preferably 15 hours) at 100-110° C. Optionally, the stirring time can be 14-24 h (preferably 18 h) at 100-110° C. as well. Preferably, the reaction mixture is stirred for 18 h at 110° C. For the reaction of (VIIa) to (V), the conversion stalls at an average ratio of starting indazole to N2-alkylated product of 2.8:1 (ratio of area % HPLC). Thus, in order to also regain the non-converted starting indazole (VIIa), a column chromatography is best performed for purification of (V). Remarkably, a column chromatography procedure could be found that allowed the efficient purification of (V) to 99.5 area % HPLC and clean isolation of (VIIa) on kg-scale. (V) is obtained with an overall yield comprising the alkylation and ensuing chromatography step in the range of 45-47%. This procedure was performed at kg-scale.

In case of the transformation of (IIa) into (I), we found that a high conversion was achieved when 4.0 equiv. of a 15-35 wt % solution of 3-hydroxy-3-methylbutyl 4-methylbenzenesulfonate (VI) in toluene were dosed over 5-15 h (preferably 10 h) to a suspension of (IIa), 4.8 equiv. of an organic base (preferably N,N-diisopropylethylamine) and toluene at the reflux temperature of toluene (>110° C. internal temperature) under ambient pressure. After complete addition, the reaction is stirred for 15 h to 24 h (preferably 18 h) in order to reduce the amount of remaining (VI) in the mixture.

(V) is converted to the target compound (I) via addition of methyl magnesium halide. The procedure used in the research synthesis of (I) is disclosed in WO2016/083433, published after the priority date of the present application and described here:

705 mg (1.57 mmol) of methyl 2-(3-hydroxy-3-methylbutyl)-5-({[6-(trifluoromethyl)pyridine-2-yl]carbonyl}amino)-2H-indazole-6-carboxylate (V) were initially charged in 10 ml of THF and cooled in an ice-water cooling bath. 2.6 ml (5.0 equiv.) of 3 M methylmagnesium bromide solution in diethyl ether were added and the mixture was left to stir while cooling with an ice bath for 1 h and at room temperature for 4.5 h. Another 1 equiv. of the methylmagnesium bromide solution was added and the mixture was left to stir at room temperature for 20.5 h. Another 1 equiv. again of the methylmagnesium bromide solution was added and the mixture was left to stir at room temperature for 22 h. The reaction mixture was mixed with saturated aqueous ammonium chloride solution, stirred and extracted three times with ethyl acetate. The combined organic phases were washed with sodium chloride solution, filtered through a hydrophobic filter and concentrated. This gave 790 mg of a residue which was purified by means of preparative HPLC. This gave 234 mg of the title compound and 164 mg of a product fraction which was stirred with diethyl ether. After filtration with suction followed by drying, a further 146 mg of the title compound were obtained.

Total yield: 398 mg (56%)

This procedure is not suitable for large scale production due to the following reasons:

The use of diethylether must be avoided due to its low ignition point and its high explosive potential.

The relatively costly methylmagnesium bromide was used instead of the more common methylmagnesium chloride which is easier to procure.

The total time of the reaction is very long (47 hl)

The reaction is accompanied by the formation of many unwanted side-products, so that a preparative HPLC had to be used for purification.

Chromatographic separations should be avoided on technical scale, as they usually require an uneconomical consumption of organic solvents.

No crystallization procedure has been described. According to the usual practice in research laboratories, compound (I) was evaporated to dryness. This operation is not feasible on technical scale.

Surprisingly, we found that compound (V) could be prepared with a significantly higher yield when methylmagnesium chloride in THF was used instead. The reaction proceeds with less side-products which, using the research method as disclosed in WO2016/083433, had to be removed via preparative HPLC. The reaction was found to proceed best with THF as solvent. 6 equiv. methylmagnesium chloride (ca. 3 M in THF) are stirred and kept at −10 to −15° C. Within 1-2 h (preferably 1.75 h) compound (V) is added dropwise to the mixture as a solution in THF. The reaction mixture is stirred for 30 min at the indicated temperature. The cold reaction mixture is subsequently quenched by being dosed into an aqueous solution of citric acid. The resulting mixture is stirred vigorously. Phases are separated. The aqueous phase is extracted with ethyl acetate. The combined organic phases are washed with water. A solvent swap to ethanol is performed. The resulting solution is warmed to 31-32° C. and stirred. The crude product is crystallized by adding water over a period of 1 h. The resulting suspension is then cooled to 20° C. within 1 h and the crude product is isolated via filtration and washed with a mixture of ethanol and water. The crude product is dried. For purification, the product is subjected to further crystallization using a mixture of acetone/toluene 1:9. The crude material is dissolved in this mixture at app. 80° C. The solution is cooled to 55° C. It proved advantageous to add seeding crystals at this temperature. The resulting suspension is further cooled to 20° C. within 2 h, the product is filtered off, washed with a mixture of acetone/toluene 1:9 and toluene and dried.

In order to receive a defined crystalline form, the product is subjected to crystallization with ethanol and water analogously to the procedure described above. Using this procedure, the desired compound (I) is obtained with high purity (>97 area % HPLC; >96% content) and good yields (55-77%). Remarkably, the yields were higher (72 and 77%) when the reaction was run at larger scale (kg).

Notably, we found that the alkylation reaction of (IIa) to (I) gave the best results when only 4.5 to 6 equiv. base (N,N-dicyclohexylamine or triethylamine, preferably N,N-diisopropylethylamine) were used. We also found that a simultaneous and slow addition of a solution of (VI) in toluene (15-40 wt %; preferably 25 wt %) proved beneficial. When the addition is performed simultaneously, a slight excess of base must be present in the reaction mixture for the alkylation to proceed best. It is also possible to slowly add the solution of (VI) in an unpolar hydrocarbon solvent, in particular toluene, to a mixture of (IIa) and organic base in the same unpolar hydrocarbon solvent. For this reaction, a toluene solution of (VI) has been prepared according to an optimized procedure with respect to safety and handling, as (VI) is prone to exothermic decomposition. Thus, (IIa) is suspended in toluene (ca. 6.5 volumes) and heated to 100-≥112° C. (preferably reflux temperature of toluene as internal temperature). After complete addition, the reaction mixture is stirred for 18 h at 100-≥112° C. After complete addition, the reaction was stirred for 15 to 24 hours, preferably 18 h, in order to decrease the amount of the remaining excess of the alkylating agent (VI). The reaction mixture is then cooled to a temperature of 40° C. and concentrated under vacuum.

The reaction mixture is then cooled to 40° C. and concentrated. A phase extraction sequence follows using ethyl acetate, a mixture of acetic acid/water, and water. The organic phase is concentrated and a solvent swap to isopropanol is performed. The desired product (I) is crystallized via slow addition of water. In some cases, it proved useful to seed the mixture with small amounts of crystals in order to obtain a reproducible crystallization. After prolonged stirring of the resulting suspension, the product is isolated via filtration, washed with a mixture of isopropanol and water, and finally water. The product is dried at 50-60° C. under vacuum resulting typically in 60-90% yield. The purity of the crude product typically amounts to 76-89% (area % HPLC; method D) (70 to 90 wt % content) with less than 6% (HPLC) of N1-regioisomer. This work-up, however, proved difficult at large scale (1.2 kg), as the content of the product was lower than that originally obtained at lab scale (down to 61 wt %; 71 area % HPLC; method C; 76 area % HPLC; method D).

The crude product can be purified via repetitive crystallization from a toluene/acetone mixture similar to the crystallization procedure applied after the reaction of (V) to (I). Here, we found it beneficial to add activated charcoal (0.1-0.4 equiv.) in order to achieve optimal results. (I) is thus received with purities of 95 to >99 area % HPLC.

The preparation of cGMP material which will also be used in clinical trials requires additional purification. In addition, since the active pharmaceutical ingredient will be used for tablet production, a procedure is required that reproducibly furnishes the identical crystalline form. Surprisingly, a defined crystal form could be installed via recrystallization with ethanol and water. For cGMP filtration the compound is first dissolved in ethanol passed through a particle filter and subsequently crystallized via addition of water. The pure product is usually obtained in 35-56% with high purity and content.

Since the above-described work-up resulted in content fluctuations when applied at larger scale, we searched for a more efficient work-up and purification.

Surprisingly, we found that n-butyl acetate proved suitable as solvent for an efficient purification via crystallization of crude (I). Therefore, n-butyl acetate was used both as solvent in the extractive work-up and as solvent for crystallization. The crystallization was performed using a warm-cool cycle, which notably gave material that could be easily handled for filtration. "Warm-cool cycle" in the aforementioned sense means, that the crude material was dissolved in n-butyl acetate at app. 93° C., kept at this temperature for 1 h, then cooled to 83° C. within 30 min. The material started to crystallize at this temperature, optionally seeding crystals were added. The resulting suspension was stirred for 10 min and then cooled to 60° C. within 2 h. At this temperature, the suspension was stirred for at least 30 min before it was warmed to 78° C. within 30 min. The mixture was stirred at this temperature for at least 30 min, before it was cooled to 22° C. within 6 h. The resulting suspension could be easily filtrated. The described warm-cool cycle proved essential for obtaining easily filterable material. Using this procedure, compound (I) was received with high purity (>97 area %) and yields >50%. This procedure was successfully carried out at 1 kg and 18 kg scale.

For achieving cGMP (current Good Manufacturing Practice) quality by reducing the amount of potentially genotoxic (VI) in the final product (I) to an acceptable level (<20 ppm) and for obtaining a defined crystalline form, (I) was dissolved in ethanol at 55° C. and the solution was subjected to clarification filtration. The solution was then heated to 65° C. and water was added within a time regimen, which is in analogy to that described by the mathematical equation of a cubic dosing curve*(amount water added vs. addition time):

$$m(t) = (m_{total}) \times \left(\frac{t}{t_B}\right)^3 + m_{start},$$

whereby
m(t)=amount H$_2$O vs. addition time [kg]
m$_{total}$=total amount of H$_2$O added via cubic addition [kg]
m$_{start}$=amount of water present before start of cubic addition [kg]
t=time [h]
t$_B$=total addition time [h].
* Principle of cubic dosing curve is described by S. Kim et al. in *Org. Process Res. Dev.* 2005, 9, 894.

The addition of water to a solution of compound (I) in ethanol at 65° C. within the above-described time regimen ("cubic dosing curve") results in product particles which are characterized by significantly larger crystal sizes (see FIG. 7) and a defined particle size distribution compared to product particles obtained after water addition at the same temperature (65° C.), but within a time regimen described by the equation of a linear function (y=a×z+b), i.e. "linear water addition".

After complete addition of the total amount of water and additional stirring at 65° C., the suspension was cooled to 20° C. The precipitate was filtered off and washed with a mixture of water and ethanol and dried. The resulting crystalline particles have a defined shape and the desired properties required for formulation of a pharmaceutical composition, such as a tablet (see Experimental Section: XRPD Reflexes) with high purity (>97 area %) and high yield (>90%).

The novel crystallization procedure provides benefit with regard to filtration and operative handling of the crystalline material obtained according to the above-described protocol ("cubic dosing curve"). Thus, crystals obtained via the "cubic dosing curve" crystallization procedure showed superior filtration properties, such as a lower amount of residual moisture (w$_f$=28% weight) after filtration, a lower resistance of the filtration cake ($\alpha$=2.1*10$^{12}$ m$^{-2}$) and a considerably higher volume flow rate (v$_F$=12,484 l/m$^2$ h) than crystals obtained via the "linear water addition" crystallization procedure (w$_f$=37% weight; $\alpha$=8.6*10$^{12}$ m$^{-2}$; v$_F$=3,306 l/m$^2$ h). The $\alpha$- and v$_F$-values were determined in a normalized filtration experiment analogous to the VDI 2762 Part 2 guideline dated December 2010. The residual moisture was determined in a drying oven (Heraeus vacutherm, 30 mbar, 50° C., overnight) and with a Halogen Moisture Anaylzer HG53 (Mettler Toledo) at 120° C.

Additionally, the obtained crystals can be defined by a specific particle size distribution of x90:7.7-9.7 μm; x50: 2.7-3.2 μm; x10:0.9-1.0 μm.

In contrast, crystals obtained with the "linear water addition" are defined by a particle size distribution of x90:7.7-9.7 μm; x50:2.7-3.2 μm; x10: 0.9-1.0 μm.

The most commonly used metrics when describing particle size distributions are x-values (x10, x50 & x90) which are the intercepts for 10%, 50% and 90% of the cumulative mass.x-Values can be thought of as the diameter of the sphere which divides the samples mass into a specified percentage when the particles are arranged on an ascending mass basis. For example, the x10 is the diameter at which 10% of the sample's mass is comprised of particles with a diameter less than this value. The x50 represents the diameter of the particle that 50% of a sample's mass is smaller than and 50% of a sample's mass is larger than.

This procedure is well compatible with technical scales.

Product that is obtained from this crystallization procedure possesses the desired properties required for preparation of a pharmaceutical composition, such as a tablet (see Experimental Section: XRPD Reflexes). The crystalline material obtained via the above described crystallization procedure displays good stability during storage. It can also be easily micronized without losing its crystal properties.

It must be emphasized that the N2-selective alkylation of a complexly functionalized indazole using an alkylating agent bearing reactive functionalities apart from the leaving group is novel, without precedence in the literature and therefore a scientifically highly significant invention for the preparation of such substitution patterns.

In the previous non-selective alkylation reactions, 4-bromo-2-methylbutan-2-ol (CAS No. 35979-69-2) was used as alkylating agent. Larger quantities of this material are difficult to procure so that this compound does not represent a viable option on scale. We therefore decided to switch to the corresponding tosylate (VI) (CAS No. 17689-66-6) which can be prepared from readily available 3-methylbutane-1,3-diol (IX) (CAS No. 2568-33-4) and p-toluenesulfonyl chloride (X) (CAS No. 98-59-9).

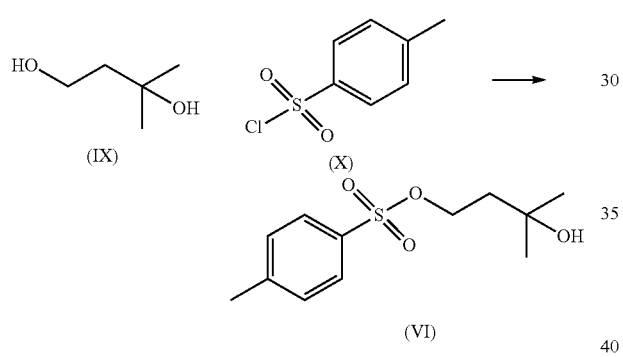

Notably, we found that the reaction can be carried out at a very high concentration of (IX) in dichloromethane (total: 5.8-6 volumes). (IX) is first mixed with triethylamine and 4-dimethylaminopyridinee (CAS No. 1122-58-3) in dichloromethane (2 volumes) at 20-25° C. This reaction mixture is cooled to 0±5° C. A solution of (X) in dichloromethane (2-2.1 volumes) is added over a period of 75-90 min. The reaction is warmed to ambient temperature (20-25° C.) and stirred for 12-18 h (preferably 15 h). The reaction mixture is quenched with water. The pH is adjusted to 1.5-2. Phases are separated. Half-saturated aq. NaCl-solution is added to the organic phase and the pH is adjusted to 7-7.5 using saturated aq. NaHCO$_3$-solution. Phases are separated and the organic phase is concentrated using a rotary evaporator. At technical scale (1.5 kg of starting material (IX)) repeatedly defined amounts of dichloromethane are added to the residue and evaporated in order to remove remaining water. The compound was obtained as a slightly yellow to colorless viscous oil in yields from 90-98% and a purity of typically around 90 area % HPLC.

Remarkably, DSC measurements on (VI) showed that the compound is prone to exothermic decomposition at around 100° C. Acids and additives such as rust were shown to promote this decomposition. Therefore, a more safe and straightforward process for the preparation of (VI) had to be found. Surprisingly, we discovered that (VI) can be directly prepared as a concentrated solution (15-40 wt %) in toluene at low temperature. Thus, (IX) is emulsified in 1.5 volumes toluene. The mixture is cooled to 0° C. and 1.1 equiv. triethylamine is added followed by 0.05 equiv. 4-dimethylaminopyridinee. A highly concentrated solution of (X) in toluene (1.6 volumes) is dropped to the reaction mixture at 0° C. over a period of 2 h. Stirring is continued for 12-18 h (preferably 15 h) at 0° C. The precipitate (triethylammonium chloride) is filtered off and a clear solution of (IV) in toluene is obtained. Remarkably, this solution can directly be used in the N2-selective alkylation reaction without any further work-up or purification. This procedure avoids the exposure of (VI) to heat, acid and large excess of base. Since the toluene solution of (VI) is telescoped and used directly after filtration in the N2-selective alkylation reaction of (IIa) to (I), it proved crucial to for the final purity of (I) to meet the cGMP purity requirements that a slight excess of 3-methylbutane-1,3-diol (IX) towards p-toluenesulfonyl chloride (X) is used in the production of the solution of (VI) and to make sure that only very small amounts of (X) (<0.05 area %, HPLC) are still present in the solution. In order to have the best possible control over the stoichiometries of (IX) vs. (X), it is beneficial to subject the relative hygroscopic compound (IX) in a first step to an azeotropic distillation with toluene in order to remove water.

The preparations of compounds with the general formula (II) are described in WO 2015/091426. This new inventive process focuses on the compound shown by formula (IIa):

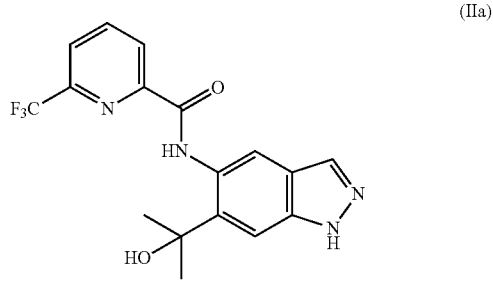

In the published patent application WO 2015/091426, compound (IIa) is described to be prepared via reaction of the methyl ester (VIIa) with a solution of methylmagnesium bromide in diethylether.

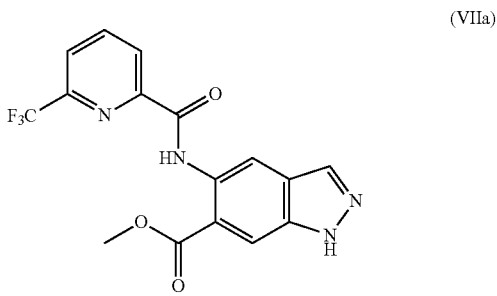 [SMILES: COC(=O)c1cc2[nH]ncc2cc1NC(=O)c1cccc(C(F)(F)F)n1]

After work-up, the crude product is subjected to a column chromatographic purification furnishing compound (IIa) in 45% yield.

This procedure is not suitable for a production of (IIa) on technical scale due to the following drawbacks:

The use of diethylether must be avoided due to its low ignition point and its high explosive potential.

The relatively costly methylmagnesium bromide was used instead of the more common methylmagnesium chloride which is easier to procure.

Chromatographic separations should be avoided on technical scale as they usually require a massive uneconomical consumption of organic solvents.

No crystallization procedure has been described. According to the usual practice in research laboratories, compound (IIa) was evaporated until dryness. This operation is not feasible on technical scale.

Surprisingly, it was found that compound (IIa) could be prepared with a significantly higher yield when methylmagnesium chloride and lithium chloride (2:1) in THF were used instead. The reactions proceeded with less side-products which, using the old method described in WO 2015/091426, had to be removed via tedious column chromatography. The reaction was found to proceed best with THF as solvent. 6-10 equiv. methylmagnesium chloride (ca. 3 M in THF) and 3-5 equiv. lithium chloride are stirred and kept at −10 to 0° C. Within 1-3 h (preferably 2 h) compound (VIIa) is dropped to the mixture as a solution in THF. The reaction mixture is stirred for 5 to 30 min at the indicated temperature and subsequently quenched by being poured into water. The resulting mixture is stirred vigorously. The pH of the mixture is then adjusted to ca. 4.0 via addition of a mineral or organic acid (preferably citric acid) and ethyl acetate is added. Phases were separated and the organic phase was washed several times with brine (aqueous sodium chloride solution). The resulting organic solution was subjected to a solvent swap with toluene via distillation. During this process, compound (IIa) started to crystallize and could be isolated via filtration. The precipitate was dried at elevated temperature (50-60° C.) under vacuum. Typically, yields at this stage were in the range of 80-96% and purities between 95-99 area % HPLC; method A, see experimental).

For the preparation of cGMP material it proved advantageous to finally stir this product in a mixture of isopropanol/water (1:1; 2 to 10 volumes relative to input material). The material is stirred for 1-5 h, preferably 3 h. It is then filtrated and washed twice with small amounts of a 1:1 isopropanol/water mixture. The product is dried at elevated temperature (50-60° C.) under vacuum. Typically, yields >90% and purities >97 area % (HPLC; method A) are achieved.

In the following examples in the experimental section, a variant (see example #2, variant #3) is also described in which, after treatment with activated charcoal, a solvent swap directly to isopropanol is performed. The product is crystallized by addition of water. In this way, the product is directly obtained with very high purity.

The preparation of compound (VIIa) has also been described in the patent application WO 2015/091426. Thereby, 6-(trifluoromethyl)pyridinee-2-carboxylic acid (XI) (CAS No. 21190-87-4) was coupled with aniline (XII) (methyl-5-amino-1H-indazol-6-carboxylate; CAS No. 1000373-79-4) using 1-[bis(dimethylamino)methylene]-1H-1,2,3-triazolo[4,5-b]pyridineium 3-oxid hexafluorophosphate (CAS No. 148893-10-1) as coupling reagent. Amide (VIIa) was obtained with 84% yield.

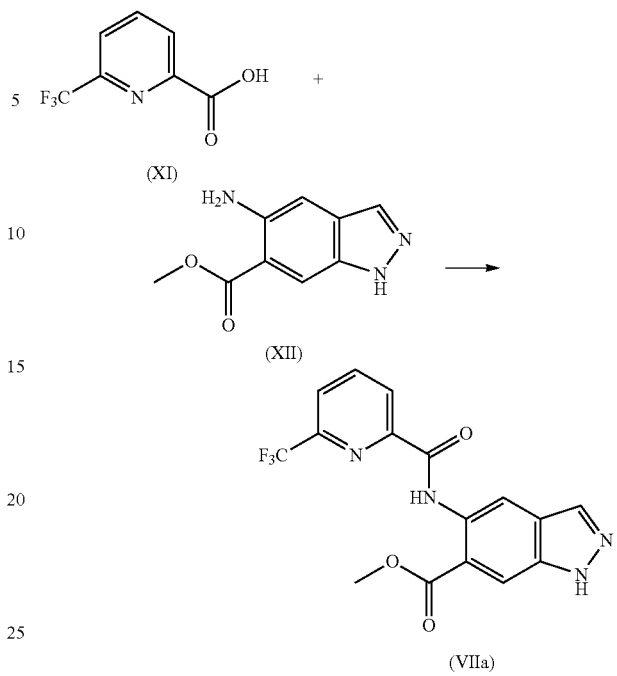

Due to safety reasons, an up-scaling of uronium-based coupling reagents is not possible for the reasons of its explosive potential. Therefore, an alternative coupling method had to be found. The safe and scalable method for the preparation of amide (VIIa) is based on the use of T3P (2,4,6-tripropyl-1,3,5,2,4,6-trioxatriphosphorinane-2,4,6-trioxide; CAS No. 68957-94-8) as coupling reagent. The reaction proceeds smoothly and furnishes amide (VIIa) with high yields. In a one-pot process, carboxylic acid (XI) (best used with a slight shortage of (XI) relative to aniline (XII), ca. 0.90-0.95 equiv.) is placed along with 1.5 equiv. N,N-diisopropylethylamine in 7-16 volumes THF. Subsequently, 2 equiv. T3P (50 wt % solution in ethyl acetate) are slowly added at 0-5° C. over a period of 45 min. The reaction mixture is additionally stirred for 2-4 h (preferably 2 h) at 0-5° C.

The cold mixture was then quenched with (cold) water, its pH adjusted with sodium carbonate aq. solution or alternatively ammonium hydroxide solution to 7.5. The resulting suspension was then (when only 7 volumes of THF were used for the reaction) warmed to ambient temperature and filtered. The product was washed with water and ethanol and dried under vacuum at 45° C. In case of 16 volumes of THF, the THF/ethyl acetate mixture was largely distilled off (200 mbar, 45-50° C. internal temperature). Subsequently, water and ethanol were added and the pH was adjusted to 7.0 by adding sodium carbonate aq. solution. The mixture was stirred 1-5 h, preferably 1-2 h, at 50° C., then cooled to 20-25° C. and stirred for 10-30 min. The product was isolated via filtration and subsequently washed with a mixture of ethanol and water and finally dried under vacuum at 45° C. With this process, typically high yields between 84-96% were obtained. The purity was in all cases >98 area % (HPLC; methods A & B).

In some cases, especially when aniline (XII) of poor optical quality (e.g. dark brown color) was used as starting material, it proved useful to perform a treatment with activated charcoal. This procedure is described in the following section:

Crude amide (VIIa) was dissolved in a mixture of methanol and THF (2:1) and activated charcoal was added. The mixture was heated to 60-65° C. for 1-1.5 h. The activated charcoal was filtered off and the filtrate was concentrated (down to 2 volumes relative to input material). Water was added and the product precipitated, was filtered, washed and dried at 55-60° C. (under vacuum).

Compounds (XI) and (XII) have been reported in the literature and both are commercially available in large quantities.

XI: Cottet, Fabrice; Marull, Marc; Lefebvre, Olivier; Schlosser, Manfred, European Journal of Organic Chemistry, 2003, 8 p. 1559-1568; Carter, Percy H.; Cherney, Robert J.; Batt, Douglas G.; Duncia, John V.; Gardner, Daniel S.; Ko, Soo S.; Srivastava, Anurag S.; Yang, Michael G. Patent: US2005/54627 A1, 2005; Ashimori; Ono; Uchida; Ohtaki; Fukaya; Watanabe; Yokoyama Chemical and Pharmaceutical Bulletin, 1990, vol. 38, 9 p. 2446-2458

XII: Nissan Chemical Industries, Ltd.; CHUGAI SEIYAKU KABUSHIKI KAISHA, EP2045253 A1, 2009.

Evaluation of the Total Processes:

The following schemes depict the total syntheses of pure product (I) from aniline (XII). When calculating with the best yields achieved for each step, a total average yield of approximately 35% is obtained for the route via N2-selective preparation of (V). This also includes the installation of the final crystalline form.

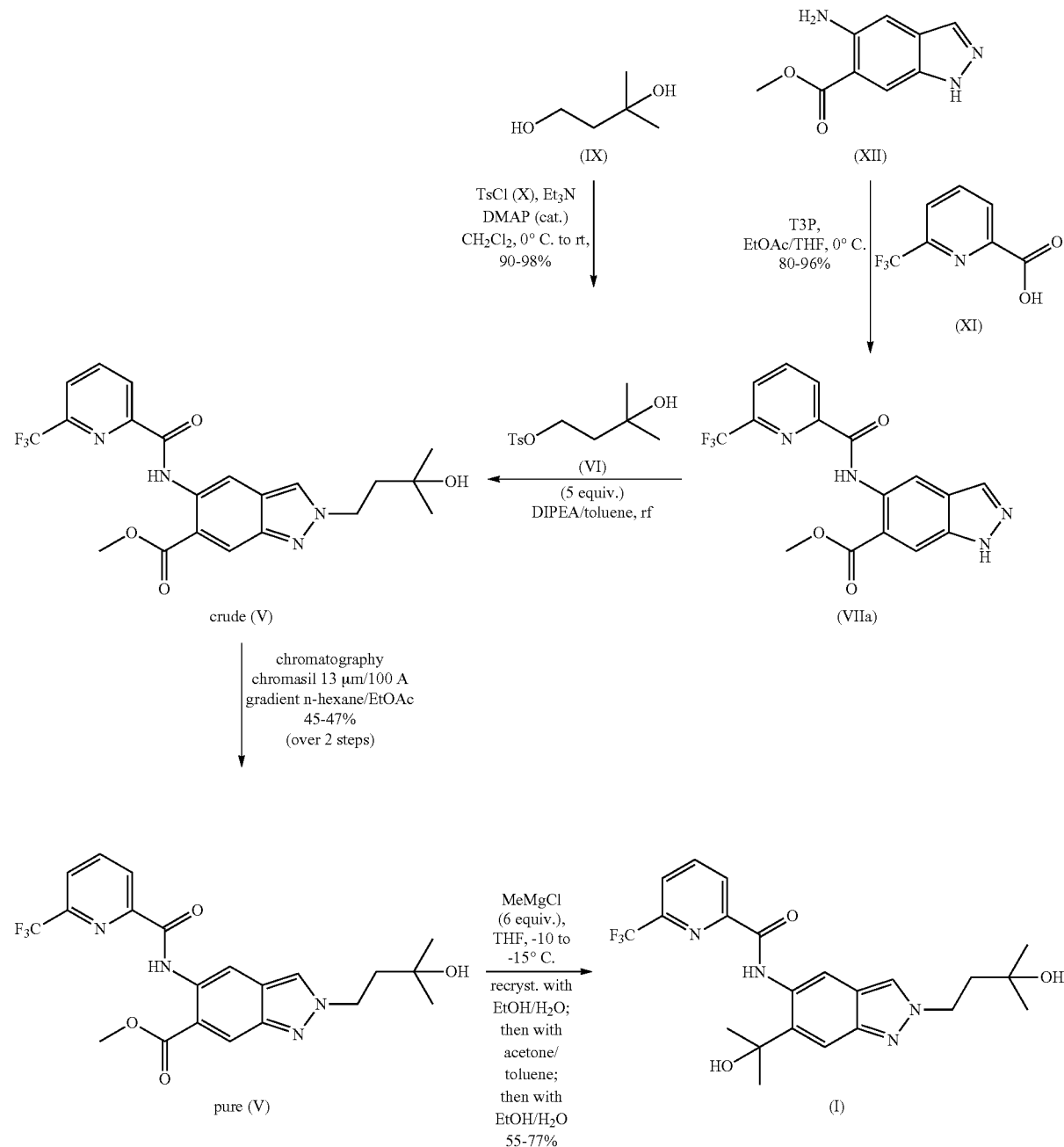

The synthetic route via (IIa) completely avoids column chromatographic purification and furnishes the desired compound (I) with very high purity (>98 area %; method C) and defined crystalline needle form and size (see FIG. 7). The total yield is higher than that obtained after using the synthetic route via (V): total average yield of approximately 42%.

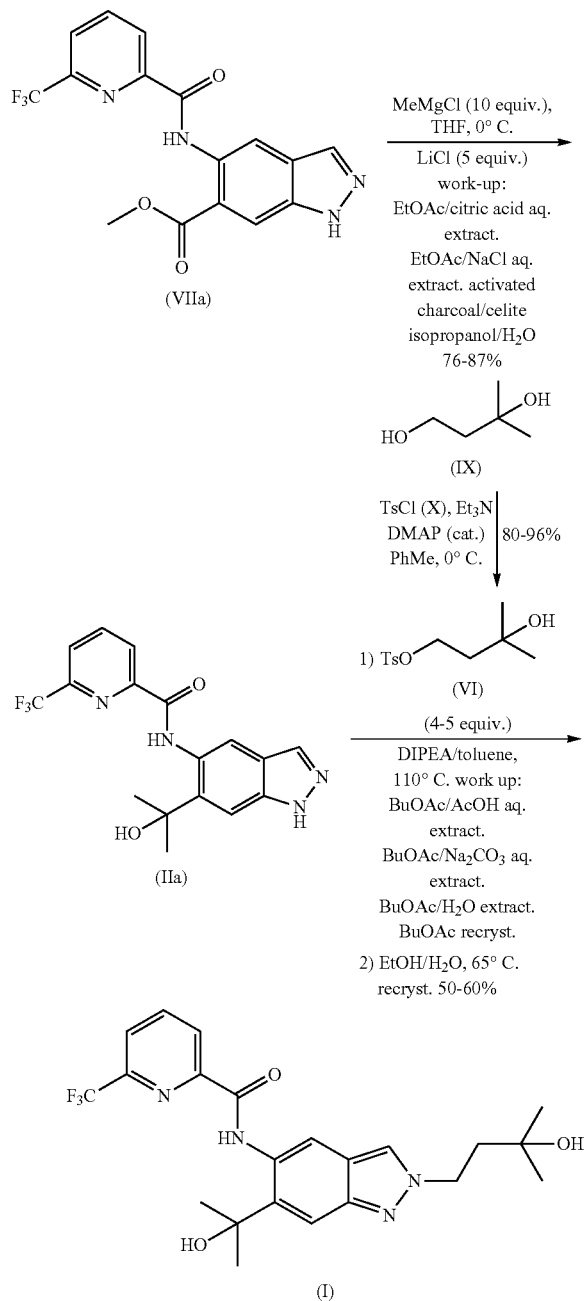

When comparing these total yields with the published prior art data with regard to
1. amide coupling (preparation of VI): 84% yield;
2. Grignard reaction followed by chromatographic purification: Grignard reaction on (VIIa): 45% yield; on (V): 56% yield.
3. alkylation with 4-bromo-2-methylbutan-2-ol analogously to methods known to the skilled person followed by chromatographic purification: alkylation of (VIIa): 37% yield; alkylation of (IIa): 26% yield, the advantages of the new processes become very clear:

With the prior method a total yield of only 9.8-17.4% could be achieved with an installation of the final crystalline needle form not included.

To conclude, the new inventive processes furnish compound (I) with 2.4 (route via (V)) to 4.3 times (route via (IIa)) higher total yields as compared to the prior art. They, moreover, include the directed and reproducible preparation of a defined crystalline needle form and size (see FIG. 7).

Hence, in a first aspect, the present invention relates to a method of preparing a compound of formula (I) via the following steps shown in reaction scheme IA, infra:

Scheme IA.

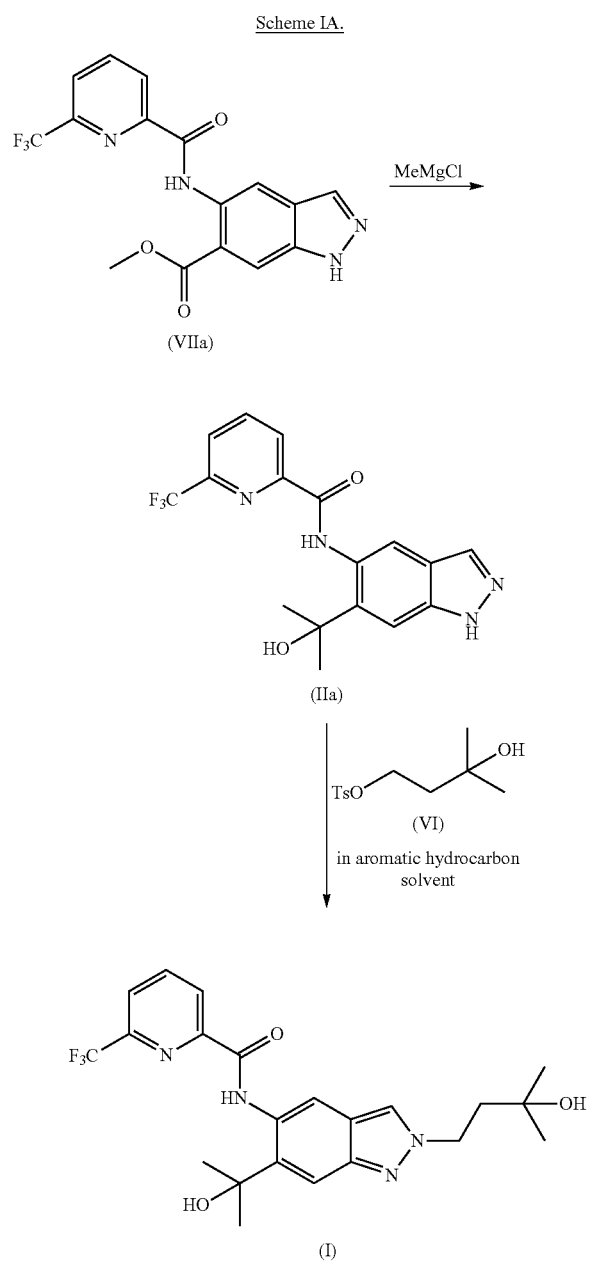

In an embodiment of the first aspect, the present invention relates to a method of preparing a compound of formula (I) via the following steps shown in reaction scheme I, infra:

Scheme I.

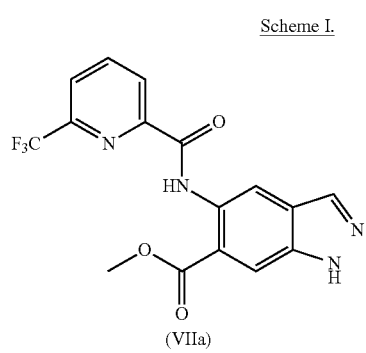

(VIIa)

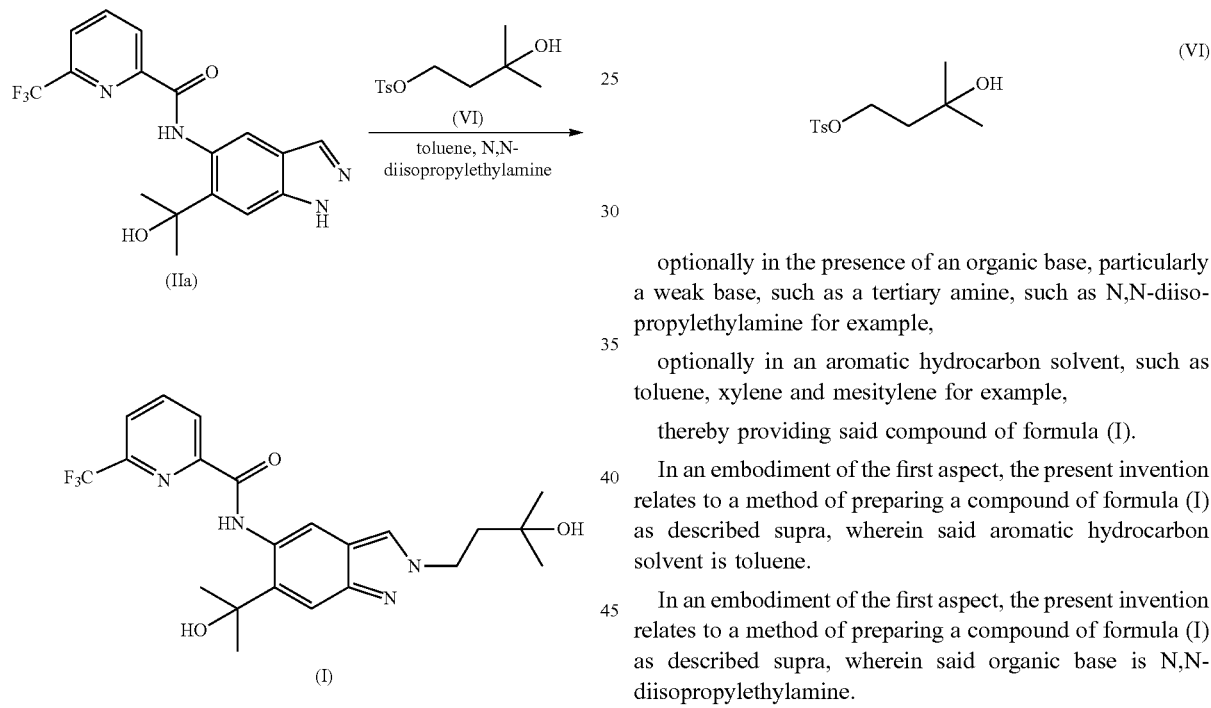

(IIa)

(I)

In an embodiment of the first aspect, the present invention relates to a method of preparing a compound of formula (I):

comprising the following step (A):
wherein a compound of formula (IIa):

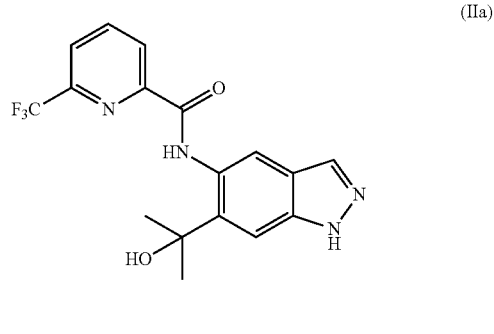 [SMILES: CC(C)(O)c1cc2[nH]ncc2cc1NC(=O)c1cccc(C(F)(F)F)n1]

(IIa)

is allowed to react with a compound of formula (VI):

(VI)

optionally in the presence of an organic base, particularly a weak base, such as a tertiary amine, such as N,N-diisopropylethylamine for example, optionally in an aromatic hydrocarbon solvent, such as toluene, xylene and mesitylene for example, thereby providing said compound of formula (I).

In an embodiment of the first aspect, the present invention relates to a method of preparing a compound of formula (I) as described supra, wherein said aromatic hydrocarbon solvent is toluene.

In an embodiment of the first aspect, the present invention relates to a method of preparing a compound of formula (I) as described supra, wherein said organic base is N,N-diisopropylethylamine.

In an embodiment of the first aspect, the present invention relates to a method of preparing a compound of formula (I) as described supra, wherein said compound of formula (IIa):

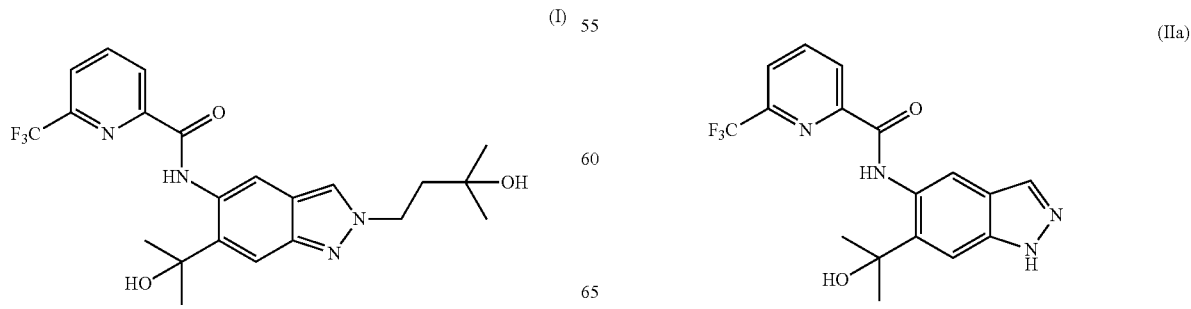

is prepared by the following step (B):
wherein a compound of formula (VIIa):

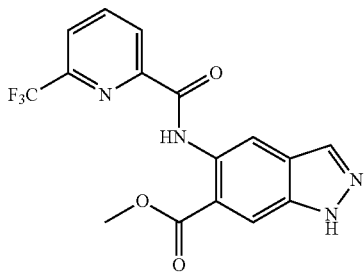

(VIIa)

is allowed to react with a reductive methylating agent, such as a methylmetallic agent, such as a methylmagnesium halide, such as methylmagnesium chloride for example,
optionally in the presence of an alkali metal halide, such as lithium chloride for example,
thereby providing said compound of formula (IIa).

In an embodiment of the first aspect, the present invention relates to a method of preparing a compound of formula (I) as described supra, wherein said compound of formula (VIIa):

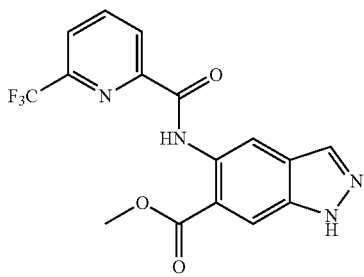

(VIIa)

is prepared by the following step (C):
wherein a compound of formula (XII):

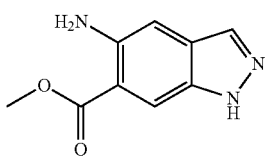

(XII)

is allowed to react with a compound of formula (IX):

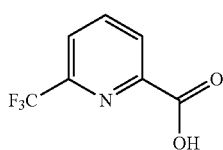

(XI)

optionally in the presence of an organic base, particularly a weak organic base, such as a tertiary amine, such as N,N-diisopropylethylamine for example,
optionally in the presence of a coupling agent, such as 2,4,6-tripropyl-1,3,5,2,4,6-trioxatriphosphinane 2,4,6-trioxide (T3P) for example,
thereby providing said compound of formula (VIIa).

In an embodiment of the first aspect, the present invention relates to a method of preparing a compound of formula (I) as described supra, wherein said compound of formula (I) is purified by crystallization, particularly from a solvent or a mixture of solvents such as a mixture of acetone and toluene, optionally in the presence of activated charcoal,
optionally followed by a further crystallization from a solvent such as ethanol for example.

In an embodiment of the first aspect, the present invention relates to a method of preparing a compound of formula (I) as described supra, wherein said compound of formula (I) is in the form of crystalline needles which correspond to the hydrate (form A) of the compound of formula (I).

In accordance with a second aspect, the present invention relates to a crystalline form, which corresponds to the hydrate (form A) of the compound of formula (I):

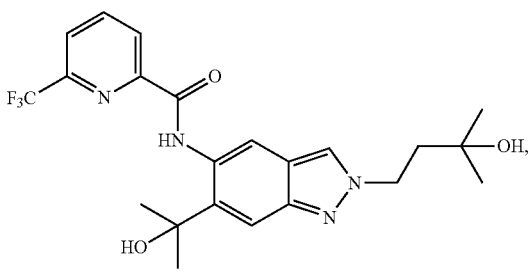

(I)

as prepared by the method as described supra.

In accordance with a second aspect, the present invention relates to a crystalline form, which corresponds to the hydrate (form A) of the compound of formula (I):

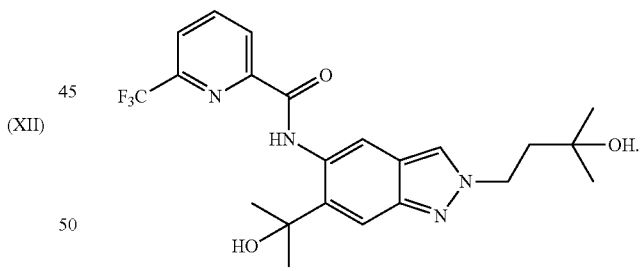

(I)

In accordance with a second aspect, the present invention relates to a crystalline form, which corresponds to the hydrate (form A) as described supra, having an XRPD peak maxima [°2Θ](Copper (Cu)) as follows:

TABLE 1

| XRPD of hydrate, anhydrate and formamide solvate of compound (I) Reflections [Peak maximum °2Theta] | | |
|---|---|---|
| Hydrat | Anhydrat | Formamid-Solvat |
| 6.2 | 8.6 | 5.5 |
| 7.9 | 10.3 | 9.7 |
| 9.4 | 12.2 | 10.0 |

TABLE 1-continued

XRPD of hydrate, anhydrate and formamide solvate of compound (I)
Reflections [Peak maximum °2Theta]

| Hydrat | Anhydrat | Formamid-Solvat |
|---|---|---|
| 10.8 | 12.7 | 10.4 |
| 12.5 | 13.1 | 10.5 |
| 13.0 | 13.5 | 11.5 |
| 13.8 | 14.2 | 11.7 |
| 15.0 | 14.6 | 12.0 |
| 15.3 | 15.4 | 13.9 |
| 15.5 | 15.7 | 14.7 |
| 15.7 | 16.3 | 15.3 |
| 16.0 | 17.3 | 15.5 |
| 16.3 | 18.3 | 15.8 |
| 17.0 | 18.8 | 16.2 |
| 18.0 | 19.4 | 16.6 |
| 18.2 | 19.8 | 17.2 |
| 18.7 | 19.9 | 17.7 |
| 19.3 | 20.3 | 17.9 |
| 20.1 | 21.0 | 18.0 |
| 20.3 | 21.4 | 18.5 |
| 20.8 | 21.8 | 18.5 |
| 21.0 | 22.2 | 18.7 |
| 21.4 | 23.7 | 19.2 |
| 21.7 | 24.5 | 19.3 |
| 22.9 | 25.0 | 19.4 |
| 23.4 | 25.2 | 19.5 |
| 24.0 | 25.7 | 19.7 |
| 24.3 | 25.9 | 20.0 |
| 25.1 | 26.1 | 20.1 |
| 25.3 | 27.0 | 20.3 |
| 25.7 | 27.3 | 20.5 |
| 26.6 | 27.5 | 20.7 |
| 27.1 | 28.4 | 20.9 |
| 27.6 | 28.7 | 21.1 |
| 28.4 | 28.9 | 21.3 |
| 28.4 | 29.3 | 21.7 |
| 28.7 | 29.5 | 22.0 |
| 29.0 | 30.4 | 22.2 |
| 29.8 | 30.7 | 22.4 |
| 30.1 | 31.0 | 22.8 |
| 30.3 | 31.7 | 23.0 |
| 31.1 | 32.1 | 23.6 |
| 31.4 | 32.3 | 23.9 |
| 31.7 | 33.0 | 24.1 |
| 32.0 | 33.2 | 24.4 |
| 32.4 | 33.8 | 24.6 |
| 33.0 | 34.0 | 25.0 |
| 33.2 | 34.3 | 25.4 |
| 33.4 | 34.6 | 25.6 |
| 33.8 | 35.0 | 26.2 |
| 34.5 | 35.1 | 26.6 |
| 34.8 | 35.8 | 27.0 |
| 35.1 | 36.1 | 27.4 |
| 35.9 | 36.4 | 27.9 |
| 37.0 | 36.8 | 28.3 |
| 37.1 | 37.0 | 28.6 |
| 37.5 | 37.2 | 28.9 |
| 37.5 | 37.4 | 29.3 |
| 38.0 | 37.6 | 29.9 |
| 38.3 | 38.0 | 30.0 |
| 38.5 | 38.4 | 30.2 |
| 38.8 | 38.7 | 30.4 |
| 39.1 | 39.1 | 30.6 |
| 39.3 | 39.6 | 30.9 |
|  |  | 31.2 |
|  |  | 31.6 |
|  |  | 32.0 |
|  |  | 32.3 |
|  |  | 32.5 |
|  |  | 32.6 |
|  |  | 32.9 |
|  |  | 33.1 |
|  |  | 33.5 |
|  |  | 33.9 |
|  |  | 34.9 |
|  |  | 35.0 |
|  |  | 35.4 |
|  |  | 35.8 |
|  |  | 36.1 |
|  |  | 37.0 |
|  |  | 37.6 |
|  |  | 37.8 |
|  |  | 38.2 |
|  |  | 38.5 |
|  |  | 38.8 |
|  |  | 39.2 |
|  |  | 39.4 |
|  |  | 39.6 |
|  |  | 39.9 |

In accordance with a fourth aspect, the present invention relates to use of a compound selected from:

(IIa)

and

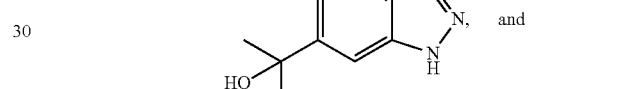

(VIIa)

for preparing a compound of formula (I):

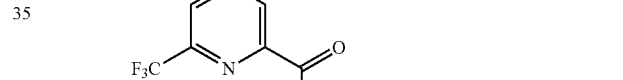

(I)

or a crystalline form, which corresponds to the hydrate (form A) of the compound of formula (I) as described supra, by the method as described supra. In accordance with a fifth aspect, the present invention relates to use of a compound of structure:

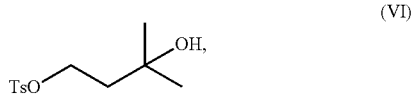 [SMILES: Cc1ccc(S(=O)(=O)OCCC(C)(C)O)cc1]

(VI)

for preparing a compound of formula (I):

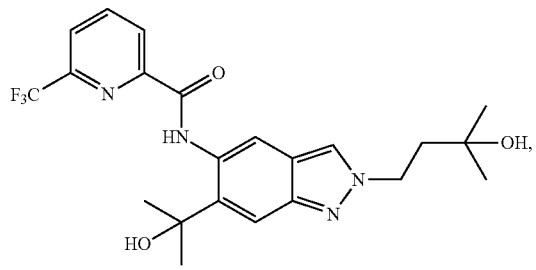

(I)

or crystalline needles, which correspond to the hydrate (form A) of the compound of formula (I) as described supra.

Method for Treatment:

The crystalline forms of the compound of formula (I), preferably the hydrate according to the invention may have useful pharmacological properties and may be employed for the prevention and treatment of disorders in humans and animals. The forms of the compound of formula (I) according to the invention may open up a further treatment alternative and may therefore be an enrichment of pharmacy.

The crystalline forms of the compound of formula (I) according to the invention can be used suitable for treatment and for prevention of proliferative and inflammatory disorders characterized by an overreacting immune system. Particular mention should be made here of the use of the crystalline forms of the compound of formula (I) according to the invention for treatment and for prevention of neoplastic disorders, dermatological disorders, gynaecological disorders, cardiovascular disorders, pulmonary disorders, ophthalmological disorders, neurological disorders, metabolic disorders, hepatic disorders, kidney diseases, inflammatory disorders, autoimmune disorders and pain. In particular, the use of the crystalline forms of the compound of formula (I) according to the invention for treatment and for prevention of lymphoma, macular degeneration, psoriasis, lupus erythematosus, multiple sclerosis, COPD (chronic obstructive pulmonary disease), gout, NASH (non-alcoholic steatohepatitits), hepatic fibrosis, insulin resistance, metabolic syndrome, chronic kidney disease, nephropathy, spondyloarthritis and rheumatoid arthritis, endometriosis and endometriosis-related pain and other endometriosis-associated symptoms such as dysmenorrhoea, dyspareunia, dysuria and dyschezia shall be specifically mentioned here.

The crystalline forms of the compound of formula (I) according to the invention can be used suitable for treatment and for prevention of pain as well, including acute, chronic, inflammatory and neuropathic pain, preferably of hyperalgesia, allodynia, pain from arthritis (such as osteoarthritis, rheumatoid arthritis and spondyloarthritis), premenstrual pain, endometriosis-associated pain, post-operative pain, pain from interstitial cystitis, CRPS (complex regional pain syndrome), trigeminal neuralgia, pain from prostatitis, pain caused by spinal cord injuries, inflammation-induced pain, lower back pain, cancer pain, chemotherapy-associated pain, HIV treatment-induced neuropathy, burn-induced pain and chronic pain.

In some embodiments, the present invention further relates to a method for the treatment and/or prophylaxis of diseases, in particular the aforementioned diseases, using an effective amount of at least one of the forms of the compound of formula (I) according to the invention.

In some embodiments, the present invention further relates to a method for the treatment and/or prophylaxis of proliferative and inflammatory disorders characterized by an overreacting immune system, in particular neoplastic disorders, dermatological disorders, gynaecological disorders, cardiovascular disorders, pulmonary disorders, ophthalmological disorders, neurological disorders, metabolic disorders, hepatic disorders, inflammatory disorders, autoimmune disorders and pain using an effective amount of at least one of the forms of the compound of formula (I) according to the invention.

The forms of the compound of formula (I) according to the invention can be used alone or in combination with other active substances if necessary. The present invention further relates to medicinal products containing at least one of the forms of the compound of formula (I) according to the invention and one or more further active substances, in particular for the treatment and/or prophylaxis of the aforementioned diseases. As suitable, other active substances, the following can be mentioned:

General mention may be made of active ingredients such as antibacterial (e.g. penicillins, vancomycin, ciprofloxacin), antiviral (e.g. aciclovir, oseltamivir) and antimycotic (e.g. naftifin, nystatin) substances and gamma globulins, immunomodulatory and immunosuppressive compounds such as cyclosporin, Methotrexat®, TNF antagonists (e.g. Humira®, Etanercept, Infliximab), IL-1 inhibitors (e.g. Anakinra, Canakinumab, Rilonacept), phosphodiesterase inhibitors (e.g. Apremilast), Jak/STAT inhibitors (e.g. Tofacitinib, Baricitinib, GLPG0634), leflunomid, cyclophosphamide, rituximab, belimumab, tacrolimus, rapamycin, mycophenolate mofetil, interferons, corticosteroids (e.g. prednisone, prednisolone, methylprednisolone, hydrocortisone, betamethasone), cyclophosphamide, azathioprine and sulfasalazine; paracetamol, non-steroidal anti-inflammatory substances (NSAIDS) (aspirin, ibuprofen, naproxen, etodolac, celecoxib, colchicine).

The following should be mentioned for tumour therapy: immunotherapy (e.g. aldesleukin, alemtuzumab, basiliximab, catumaxomab, celmoleukin, denileukin diftitox, eculizumab, edrecolomab, gemtuzumab, ibritumomab tiuxetan, imiquimod, interferon-alpha, interferon beta, interferon-gamma, ipilimumab, lenalidomide, lenograstim, mifamurtide, ofatumumab, oprelvekin, picibanil, plerixafor, polysaccharide-K, sargramostim, sipuleucel-T, tasonermin, teceleukin, tocilizumab), antiproliferative substances, for example but not exclusively amsacrine, arglabin, arsenic trioxide, asparaginase, bleomycin, busulfan, dactinomycin, docetaxel, epirubicin, peplomycin, trastuzumab, rituximab, obinutuzumab, ofatumumab, tositumomab, aromatase inhibitors (e.g. exemestane, fadrozole, formestane, letrozole, anastrozole, vorozole), antioestrogens (e.g. chlormadinone, fulvestrant, mepitiostane, tamoxifen, toremifen), oestrogens (e.g. oestradiol, polyoestradiol phosphate, raloxifen), gestagens (e.g. medroxyprogesterone, megestrol), topoisomerase I inhibitors (e.g. irinotecan, topotecan), topoisomerase II inhibitors (e.g. amrubicin, daunorubicin, elliptiniumacetate, etoposide, idarubicin, mitoxantrone, teniposide), microtubuli-active substances (e.g. cabazitaxel, eribulin, paclitaxel, vinblastine, vincristine, vindesine, vinorelbine), telomerase inhibitors (e.g. imetelstat), alkylating substances and histone deacetylase inhibitors (e.g. bendamustine, carmustine, chlormethine, dacarbazine, estramustine, ifosfamide, lomustine, mitobronitol, mitolactol, nimustine prednimustine, procarbazine, ranimustine, streptozotocin, temozolomide, thiotepa, treosulfan, trofosfamide, vorinostat, romidepsin, panobinostat); substances which affect cell differentation processes, such as abarelix, aminoglutethimide, bexarotene, MMP inhibitors (peptide mimetics, non-peptide mimetics and tetracyclines, for example marimastat, BAY 12-9566, BMS-275291, clodronate, prinomastat, doxycycline), mTOR inhibitors (e.g. sirolimus, everolimus, temsirolimus, zotarolimus), antimetabolites (e.g. clofarabine, doxifluridine, methotrexate, 5-fluorouracil, cladribine, cytarabine, fludarabine, mercaptopurine, methotrexate, pemetrexed, raltitrexed, tegafur, tioguanine), platinum compounds (e.g. carboplatin, cisplatin, cisplatinum, eptaplatin, lobaplatin, miriplatin, nedaplatin, oxaliplatin); antiangiogenic compounds (e.g. bevacizumab), antiandrogenic compounds (e.g. bevacizumab, enzalutamide, flutamide, nilutamide, bicalutamide, cyproterone, cyproterone acetate), proteasome inhibitors (e.g. bortezomib, carfilzomib, oprozomib, ONYX0914), gonadoliberin agonists and antagonists (e.g. abarelix, buserelin, deslorelin, ganirelix, goserelin, histrelin, triptorelin, degarelix, leuprorelin), methionine aminopeptidase inhibitors (e.g. bengamide derivatives, TNP-470, PPI-2458), heparanase inhibitors (e.g. SST0001, PI-88); inhibitors against genetically modified Ras protein (e.g. farnesyl transferase inhibitors such as lonafarnib, tipifarnib), HSP90 inhibitors (e.g. geldamycin derivatives such as 17-allylaminogeldanamycin, 17-demethoxygeldanamycin (17AAG), 17-DMAG, retaspimycin hydrochloride, IPI-493, AUY922, BIIB028, STA-9090, KW-2478), kinesin spindle protein inhibitors (e.g. SB715992, SB743921, pentamidine/chlorpromazine), MEK (mitogen-activated protein kinase kinase) inhibitors (e.g. trametinib, BAY 86-9766 (refametinib), AZD6244), kinase inhibitors (e.g. sorafenib, regorafenib, lapatinib, Sutent®, dasatinib, cetuximab, BMS-908662, GSK2118436, AMG 706, erlotinib, gefitinib, imatinib, nilotinib, pazopanib, roniciclib, sunitinib, vandetanib, vemurafenib), hedgehog signalling inhibitors (e.g. cyclopamine, vismodegib), BTK (Bruton's tyrosine kinase) inhibitor (e.g. ibrutinib), JAK/pan-JAK (janus kinase) inhibitor (e.g. SB-1578, baricitinib, tofacitinib, pacritinib, momelotinib, ruxolitinib, VX-509, AZD-1480, TG-101348), PI3K inhibitor (e.g. BAY 1082439, BAY 80-6946 (copanlisib), ATU-027, SF-1126, DS-7423, GSK-2126458, buparlisib, PF-4691502, BYL-719, XL-147, XL-765, idelalisib), SYK (spleen tyrosine kinase) inhibitors (e.g. fostamatinib, Excellair, PRT-062607), p53 gene therapy, bisphosphonates (e.g. etidronate, clodronate, tiludronate, pamidronate, alendronic acid, ibandronate, risedronate, zoledronate). For combination, the following active ingredients should also be mentioned by way of example but not exclusively: rituximab, cyclophosphamide, doxorubicin, doxorubicin in combination with oestrone, vincristine, chlorambucil, fludarabin, dexamethasone, cladribin, prednisone, 131l-chTNT, abiraterone, aclarubicin, alitretinoin, bisantrene, calcium folinate, calcium levofolinate, capecitabin, carmofur, clodronic acid, romiplostim, crisantaspase, darbepoetin alfa, decitabine, denosumab, dibrospidium chloride, eltrombopag, endostatin, epitiostanol, epoetin alfa, filgrastim, fotemustin, gallium nitrate, gemcitabine, glutoxim, histamine dihydrochloride, hydroxycarbamide, improsulfan, ixabepilone, lanreotide, lentinan, levamisole, lisuride, lonidamine, masoprocol, methyltestosterone, methoxsalen, methyl aminolevulinate, miltefosine, mitoguazone, mitomycin, mitotane, nelarabine, nimotuzumab, nitracrin, omeprazole, palifermin, panitumumab, pegaspargase, PEG epoetin beta (methoxy-PEG epoetin beta), pegfilgrastim, peg interferon alfa-2b, pentazocine, pentostatin, perfosfamide, pirarubicin, plicamycin, poliglusam, porfimer sodium, pralatrexate, quinagolide, razoxane, sizofirane, sobuzoxan, sodium glycididazole, tamibarotene, the combination of tegafur and gimeracil and oteracil, testosterone, tetrofosmin, thalidomide, thymalfasin, trabectedin, tretinoin, trilostane, tryptophan, ubenimex, vapreotide, yttrium-90 glass microspheres, zinostatin, zinostatin stimalamer.

Also suitable for tumour therapy is a combination of a non-drug therapy such as chemotherapy (e.g. azacitidine, belotecan, enocitabine, melphalan, valrubicin, vinflunin, zorubicin), radiotherapy (e.g. I-125 seeds, palladium-103 seed, radium-223 chloride) or phototherapy (e.g. temoporfin, talaporfin) which is accompanied by a drug treatment with the inventive IRAK4 inhibitors or which, after the non-drug tumour therapy such as chemotherapy, radiotherapy or phototherapy has ended, are supplemented by a drug treatment with the inventive IRAK4 inhibitors.

In addition to those mentioned above, the inventive IRAK4 inhibitors can also be combined with the following active ingredients:

active ingredients for Alzheimer's therapy, for example acetylcholinesterase inhibitors (e.g. donepezil, rivastigmine, galantamine, tacrine), NMDA (N-methyl-D-aspartate) receptor antagonists (e.g. memantine); L-DOPA/carbidopa (L-3,4-dihydroxyphenylalanine), COMT (catechol-O-methyltransferase) inhibitors (e.g. entacapone), dopamine agonists (e.g. ropinirole, pramipexole, bromocriptine), MAO-B (monoaminooxidase-B) inhibitors (e.g. selegiline), anticholinergics (e.g. trihexyphenidyl) and NMDA antagonists (e.g. amantadine) for treatment of Parkinson's; beta-interferon (IFN-beta) (e.g. IFN beta-1b, IFN beta-1a Avonex® and Betaferon®), glatiramer acetate, immunoglobulins, natalizumab, fingolimod and immunosuppressants such as mitoxantrone, azathioprine and cyclophosphamide for treatment of multiple sclerosis; substances for treatment of pulmonary disorders, for example beta-2-sympathomimetics (e.g. salbutamol), anticholinergics (e.g. glycopyrronium), methylxanthines (e.g. theophylline), leukotriene receptor antagonists (e.g. montelukast), PDE-4 (phosphodiesterase type 4) inhibitors (e.g. roflumilast), methotrexate, IgE antibodies, azathioprine and cyclophosphamide, cortisol-containing preparations; substances for treatment of osteoarthritis such as non-steroidal anti-inflammatory substances (NSAIDs). In addition to the two therapies mentioned, methotrexate and biologics for B-cell and T-cell therapy (e.g. rituximab, abatacept) should be mentioned for rheumatoid disorders, for example rheumatoid arthritis, spondyloarthritis and juvenile idiopathic arthritis. Neurotrophic substances such as acetylcholinesterase inhibitors (e.g. donepezil), MAO (monoaminooxidase) inhibitors (e.g. selegiline), interferons and anticonvulsives (e.g. gabapentin); active ingredients for treatment of cardiovascular disorders such as beta-blockers (e.g. metoprolol), ACE inhibitors (e.g. benazepril), angiotensin receptor blockers (e.g. losartan, valsartan), diuretics (e.g. hydrochlorothiazide), calcium channel blockers (e.g. nifedipine), statins (e.g. simvastatin, fluvastatin); anti-diabetic drugs, for example metformin, glinides (e.g. nateglinide), DPP-4 (dipeptidyl peptidase-4) inhibitors (e.g. linagliptin, saxagliptin, sitagliptin, vildagliptin), SGLT2 (sodium/glucose cotransporter 2) inhibitors/gliflozin (e.g. dapagliflozin, empagliflozin), incretin mimetics (hormone glucose-dependent insulinotropic peptide (GIP) and glucagon-like peptid 1 (GLP-1) analogues/agonists) (e.g. exenatide, liraglutide, lixisenatide), α-glucosidase inhibitors (e.g. acarbose, miglitol, voglibiose) and sulphonylureas (e.g. glibenclamide, tolbutamide), insulin sensitizers (e.g. pioglitazone) and insulin therapy (e.g. NPH insulin, insulin lispro), substances for treatment of hypoglycaemia, for treatment of diabetes and metabolic syndrome. Lipid-lowering drugs, for example fibrates (e.g. bezafibrate, etofibrate, fenofibrate, gemfibrozil), nicotinic acid derivatives (e.g. nicotinic acid/laropiprant), ezetimib, statins (e.g. simvastatin, fluvastatin), anion exchangers (e.g. colestyramine, colestipol, colesevelam). Active ingredients such as mesalazine, sulfasalazine, azathioprine, 6-mercaptopurine or methotrexate, probiotic bacteria (Mutaflor, VSL#3®, *Lactobacillus GG, Lactobacillus plantarum, L. acidophilus, L. casei, Bifidobacterium infantis* 35624, *Enterococcus* fecium SF68, *Bifidobacterium longum, Escherichia coli* Nissle 1917), antibiotics, for example ciprofloxacin and metronidazole, anti-diarrhoea drugs, for example loperamide, or laxatives (bisacodyl) for treatment of chronic inflammatory bowel diseases. Immunosuppressants such as glucocorticoids and non-steroidale anti-inflammatory substances (NSAIDs), cortisone, chloroquine, cyclosporine, azathioprine, belimumab, rituximab, cyclophosphamide for treatment of lupus erythematosus. By way of example but not exclusively, calcineurin inhibitors (e.g. tacrolimus and ciclosporin), cell division inhibitors (e.g. azathioprine, mycophenolate mofetil, mycophenolic acid, everolimus or sirolimus), rapamycin, basiliximab, daclizumab, anti-CD3 antibodies, anti-T-lymphocyte globulin/anti-lymphocyte globulin for organ transplants. Vitamin D3 analogues, for example calcipotriol, tacalcitol or calcitriol, salicylic acid, urea, ciclosporine, methotrexate, efalizumab for dermatological disorders.

Pharmaceutical Compositions:

It is possible for the crystalline forms of the compound of formula (I) to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for crystalline forms of the compound of formula (I) to be administered in suitable administration forms.

For oral administration, it is possible to formulate the crystalline forms of the compound of formula (I) to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The crystalline forms of the compound of formula (I) can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)), ointment bases (for example petroleum jelly, paraffins, triglycerides, waxes, wool wax, wool wax alcohols, lanolin, hydrophilic ointment, polyethylene glycols), bases for suppositories (for example polyethylene glycols, cacao butter, hard fat), solvents (for example water, ethanol, isopropanol, glycerol, propylene glycol, medium chain-length triglycerides fatty oils, liquid polyethylene glycols, paraffins), surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®), buffers, acids and bases (for example phosphates, carbonates, citric acid, acetic acid, hydrochloric acid, sodium hydroxide solution, ammonium carbonate, trometamol, triethanolamine), isotonicity agents (for example glucose, sodium chloride), adsorbents (for example highly-disperse silicas), viscosity-increasing agents, gel formers, thickeners and/or binders (for example polyvinylpyrrolidone, methylcellulose, hydroxypropylmethylcellulose, hydroxypropyl-cellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®, cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropyl-methylcellulose phthalate, cellulose acetate, cellulose acetate phthalate, polyacrylates, polymethacrylates such as, for example, Eudragit®)), capsule materials (for example gelatine, hydroxypropylmethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition, which comprise at least one crystalline forms of the compound of formula (I), conventionally together with one or more pharmaceutically suitable excipient(s), and to their use according to the present invention.

Dosage of the Pharmaceutical Compositions of the Present Invention:

Based upon laboratory techniques known to evaluate compounds useful for the treatment of disorders, by pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 5 to 6000 mg per day, preferably 7 to 2000 mg per day. A unit dosage may contain from about 7 to 2000 mg, preferably 25 to 100 mg of active ingredient, and can be administered one or more times per day.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The weight data in the tests and examples which follow are, unless stated otherwise, percentages by weight; parts are parts by weight. Solvent ratios, dilution ratios and concentration data of liquid/liquid solutions are based on each case on the volume.

WORKING EXAMPLES

The following examples illustrate the present invention.
Methods:
DSC thermograms were recorded using Differential Scanning calorimeters (model Netzsch Phoenix DSC 204 F1. The measurements were performed with a heating rate of 10 Kmin$^{-1}$ using non-gastight aluminium pans. Flow gas was nitrogen. There was no sample preparation.

TGA thermograms were recorded using thermobalances (model Pyris 6) from Perkin-Elmer. The measurements were performed with a heating rate of 10 Kmin$^{-1}$ [using open ceramic pans. Flow gas was nitrogen. There was no sample preparation.

X-Ray diffraction patterns were recorded at room temperature using XRD diffractometers D8 Bruker Advance Diffraktometer (radiation Cu K alpha 1, wavelength 1.54056 Å). There was no sample preparation. All X-Ray reflections are quoted as °2Theta values with a resolution of ±0.2°.

Raman spectra are recorded at room temperature using FT-Raman-spectrophotometers model Perkin Elmer Station 400F with laser wavelength of 785 nm. Resolution was 2 cm$^{-1}$. Measurements are performed in a sample holder. There is no sample preparation.

IR-ATR-spectra are recorded at room temperature using a FT-IR-spectrophotometer one with universal diamond ATR device from Perkin-Elmer. Resolution is 4 cm$^{-1}$. There is no sample preparation.

HPLC:
Method A
HPLC Instruments Used:
a) Agilent Technologies 1260 Infinity
b) Agilent 1100 Series
Zorbax SB-AQ, 50*4.6 mm, 1.5 μm
Buffer: Ammonium dihydrogenphosphate pH: 2.4
Acetonitrile
0 min. 5% buffer
8.3 min 80% buffer
11 min. 80% buffer
210 nm/4 nm
1.2 ml/min.
Method B
HPLC Instrument Used: Agilent Technologies 1260 Infinity
A1: Acetonitrile
B1: 2.72 g KH$_2$PO$_4$+2.32 g H3PO4+2 L H$_2$O
Agilent Poroshell 120 EC-C18 3*50 mm 2.7μ
Low Pressure Limit: 0.00 bar
High Pressure Limit: 400.00 bar
Flow: 1.000 mL/min
Maximum Flow Gradient: 1.000 mL/min$^2$
Stop time: 8.00 min
Post time: 5.00 min
Starting conditions: A: 5% B: 95%

| Timetable | | | | |
|---|---|---|---|---|
| Time min | A % | B % | Flow mL/min | Pressure bar |
| 8.00 | 80.0 | 20.0 | 1.000 | 400.00 |

Injection Volume: 5.00 μL
Temperature (Column): 45.00° C.
Signal Wavelength: 210 nm
Method C
HPLC Instrument Used: Agilent Technologies, HPLC 1290 Infinity (with DAD)

| Apparatus | 1. | Ultra-High performance liquid chromatograph thermostatically controlled column oven, UV-detector and data evaluation system |
|---|---|---|
| | 2. | Stainless steel column |
| | | Length: 5 cm |
| | | Internal diameter: 2.1 mm |
| | | Filling: Acquity UPLC C18 BEH, 1.7 μm |
| Reagents | 1. | Acetonitrile, for the HPLC |
| | 2. | Water, analytical grade |
| | 3. | Phosphoric acid 85%, analytical grade |
| Test solution | | Dissolve the sample in acetonitrile in a concentration of 0.25 mg/mL. (e.g. dissolve approx. 25 mg sample, accurately weighed in acetonitrile 100 mL.) |
| Calibration solution | | Dissolve the reference standard* in acetonitrile in a concentration of 0.25 mg/mL. (e.g. dissolve approx. 25 mg reference standard, accurately weighed, in acetonitrile 100 mL.) |
| Control solution | | Prepare a control solution that is identical with the calibration solution. Additionally, the control solution contains small amounts of the organic impurities. |
| Detection sensitivity solution | | Prepare a solution containing the component Solbrol P (CAS-no.: 94-13-3; propyl 4-hydroxybenzoate) (RT approx. 2.75 min) diluted to a concentration of 0.35 μg/mL. |
| HPLC conditions | | The specified conditions are guide values. To achieve optimal separations they should, if necessary, be adapted to the technical possibilities of the chromatograph and the properties of the respective column. |
| Eluent | A. | 0.1% Phosphoric acid 85% in water |
| | B. | Acetonitrile |
| Flow rate | | 1.0 mL/min |
| Temperature of the column oven | | 40° C. |
| Temperature of the sample chamber | | room temperature |
| Detection | | Measuring wavelength: 220 nm |
| | | Bandwidth: 6 nm |
| Injection volume | | 2.0 μL |
| Draw speed | | 200 μL/min |
| Needle wash | | Solvent for flush port: acetonitrile |
| Data rate | | 10 Hz |
| Cell dimension | | 10 mm |
| Equilibration time | | 10 min (at starting conditions) |

*reference standard means the compound, which has to be analyzed, as highly pure compound, i.e. >97 area % HPLC

| Gradient | | |
|---|---|---|
| Time [min] | % A | % B |
| 0 | 95 | 5 |
| 2 | 70 | 30 |
| 6 | 60 | 40 |
| 8 | 20 | 80 |
| 12 | 20 | 80 |

| Runtime of the chromatogram | 12 min |
|---|---|
| Calculation of assay (content) | The assay is calculated using linear regression and taking into account the sample weight and assay and weight of the reference standard, with a validated chromatographic data system (e.g. Empower). |

Method D
HPLC Instrument Used: Agilent Technologies 1260 Infinity
A1: Acetonitrile
B1: 1.36 $KH_2PO_4$ + 1.74 $K_2HPO_4$ + 2 L $H_2O$
Eclipse XDB-C18 3*150 mm 3.5μ
Low Pressure Limit: 0.00 bar
High Pressure Limit: 400.00 bar
Flow: 0.500 mL/min
Stop time: 35.00 min
Post time: 10.00 min
Starting conditions: A: 95% B: 5%

| Timetable | | | | |
|---|---|---|---|---|
| Time min | A % | B % | Flow mL/min | Pressure bar |
| 30.00 | 20.0 | 80.0 | 0.500 | 400.00 |
| 35.00 | 20.0 | 80.0 | 0.500 | 400.00 |

Injection Volume: 3.004
Temperature (Column): 35.00° C.
Signal Wavelength: 220 nm
GC-HS
Residual solvent analysis via headspace gas chromatography (GC-HS)
Agilent 6890 gas chromatograph with split-injection and FID (column: Restek Rxi Sil MS; length: 20 m; internal diameter: 0.18 mm; $d_f$=1 μm). Injector temp 160° C., flow 1.2 ml/min ($H_2$) Split Ratio 18, oven Temp 40° C. (4.5 min)-14° C./min-70° C.-90° C./min-220° C. (1.69 min). Detector: temp 300° C., 400 ml/min (synth air), 40 ml/min ($H_2$), 30 ml/min ($N_2$), rate 20 Hz.

Perkin Elmer Turbomatrix 40 headspace sampler: oven 80° C., needle 150° C., transfer line 160° C., system pressure 140 kPa, equilibration time 32 min, pressurization 4.0 min, injection time 0.04 min (Sampler) 0.05 min (GC).

Sample concentration: 20 mg substance in 2 ml DMF

Particle Size Analysis

The particle size analysis is done according to European Pharmacopeia 2.9.31

The equipment was developed and manufactured by Sympatec GmbH.

The components are as follows:
- RODOS dry dispersing system with turntable and spinning brush
- HELOS laser optical bench system with detector and data acquisition units
- HELOS software for system control, data transformation and report generation N-[2-(3-hydroxy-3-methylbutyl)-6-(2-hydroxypropan-2-yl)-2H-indazol-5-yl]-6-(trifluoromethyl)-pyridine-2-carboxamide (I) in its crystalline form A is applied on the turntable. The particles are brushed into a stream of pressurized air and dispersed. When passing the laser beam the aerosol generates a diffraction pattern, which is detected and analyzed according to the Fraunhofer model (European Pharmacopoeia 8.0, 2.9.31. Particle Size Analysis by Laser Light Diffraction, 01/2010:20931, page 333-336). The results are formatted after user selection for display and printout of tables and graphics. The data are reported in μm and volume percent.

System Settings dispersion medium: dry air air pressure: 4.0 bar focus: 100 mm airflow: 2.6 $m^3/h$ optical density: 3-12% detection time: min. (not less than) 1 s rotation: 18 sample amount: approx. 200 mg

For routine purposes the mean of three measurements is reported.

HPLC Trace Analysis (ppm)

Instrument used: ultra-high performance liquid chromatograph (Agilent 1290) equipped with a thermostatically controlled column oven, mass spectrometer (Agilent 6420 Triple Quad-MS), UV-detector and data evaluation system

| | | | |
|---|---|---|---|
| Column | | Zorbax Eclipse Plus C8 | |
| | | Length: | 50 mm |
| | | Internal diameter: | 2.1 mm |
| | | Particle size: | 1.8 μm |
| | | Temperature: | 40° C. |
| Mobile Phase | Eluent A | 0.1% aq. formic acid (compressibility: $45*10^{-6}$/bar) | |
| | Eluent B | Acetonitrile contains 0.1% formic acid (compressibility: $120*10^{-6}$/bar) | |
| Flow | 0.8 mL/min | | |
| Test solution | Dissolve the sample in methanol in a concentration of 10.0 mg/mL. (e.g. dissolve approx. 20 mg sample, accurately weighed in methanol 2 mL.) | | |
| Calibration solutions | Dissolve a characterized standard of (VI) in methanol in concentrations of 0.2, 0.3, 0.4, 0.5, 0.6 and 0.75 μg/mL. | | |
| Temperature of the column oven | 40° C. | | |
| Temperature of the autosampler | 10° C. | | |
| Detection (not used for quantification) | Measuring wavelength: | | 220 nm |
| | Bandwidth: | | 6 nm |
| Injection volume | 1.5 μL | | |
| Data rate | 2.5 Hz | | |
| Detector cell | 10 mm | | |
| Equilibration time | 5 min (at starting conditions) | | |

| Gradient | | |
|---|---|---|
| Time [min] | % A | % B |
| 0.0 | 80 | 20 |
| 7.5 | 60 | 40 |
| 10.0 | 20 | 80 |
| 12.0 | 20 | 80 |

| | |
|---|---|
| Runtime of the chromatogram | 12 min |

| | |
|---|---|
| MSD parameters (used for quantification) | The conditions described here are applicable with Agilent 6420 Triple Quad-MS |
| Ion source | Electrospray ionisation (ESI) |
| Time filtering | Peakwidth 0.07 mm |
| Multiple reaction monitoring used for quantification | Precursor ion 281.1, product ion 194.9 |
| Fragmentor | 85 V |
| Collison energy | 5 V |

| Source parameters | |
|---|---|
| Gas temperature | 350° C. |
| Drying gas | 13 L/min |
| Neb. Press. | 50 psi |
| VCap | 3000 V |

| | |
|---|---|
| Recovery | For determining the recovery (W) a sample is spiked with a calibration solution of (VI) and then subjected to measurement |

Equation for calculating the percentage of recovery $$W = \frac{G_{AP} - G_P}{G_A} \cdot 100\%$$

$W$ = Recovery [%]

$G_{AP}$ = Content of (VI) in spiked sample $G_P$ = Content of (VI) in sample $G_A$ = Spiked amount of (VI)

Calculation of content of (VI) in sample $$(G_P)_i = \frac{(P_P)_i - b}{a} \cdot \frac{W_{P,soll}}{(W_P)_i}$$

$(G_P)_i$ = content of (VI) in $i^{th}$ sample $(P_P)_i$ = peak area of (VI) in $i^{th}$ sample $(W_P)_i$ = weight of $i^{th}$ sample $W_{P,soll}$ = target weight of $i^{th}$ sample $a$ = slope of calibration curve $b$ = axis intercept of calibration curve

WORKING EXAMPLES

The following examples illustrate the present invention.

Example #1

Methyl 5-({[6-(trifluoromethyl)pyridine-2-yl]carbonyl}amino)-1H-indazole-6-carboxylate (VIIa)

Variant #1

30 g methyl 5-amino-1H-indazole-6-carboxylate (XII) along with 28.5 g 6-(trifluoromethyl)pyridin-2-carboxylic acid (XI) were suspended in 235 ml (210 g) THF at 20-25° C. 40 ml (30.4 g) N,N-diisopropylethylamine were added. The mixture, a yellow solution, was then cooled to 0° C. To this mixture, 187 ml (199.7 g) of a 50 wt % solution of propylphosphonic anhydride (T3P) in ethyl acetate were added over 45 min at 0° C. The dropping funnel was rinsed with 17 ml (15 g) THF. After complete addition, the reaction mixture was stirred for 2 h at 0° C. The solution had turned red. The cold reaction mixture was then dropped over 45 min to 1.2 L water kept at 1.5° C. The dropping funnel was rinsed with 17 ml (15 g) THF. The pH of the mixture was determined to be at pH 1.6 (pH 1-2). The pH of the mixture was then adjusted to 7.5 via addition of 45 ml (40 g) of a 28-30 wt % ammonium hydroxide solution at 1.5° C. Stirring was continued for 1 h at 1.5° C. The resulting suspension was then warmed to ambient temperature (20-25° C.) within 1 h and stirring was continued for 15 min. The precipitate was filtered off and washed with 100 ml water and subsequently with 2×76 ml (60 g) ethanol. The product was dried in a drying oven under vacuum (160 mbar) and $N_2$-flux at 45° C. for 22 h.

Yield: 52.8 g (92.4%, purity: 99.3 area % HPLC)

HPLC (Method B): Rt=5.6 min.

MS (ESI pos): m/z=365 (M+H)+ $^1$H NMR (500 MHz, DMSO-d6): δ [ppm]: 3.98 (s, 3H), 8.21 (d, 1H), 8.25 (s, 1H), 8.31 (s, 1H), 8.39 (t, 1H), 8.48 (d, 1H), 9.16 (s, 1H), 12.57 (s, 1H), 13.45 (br s, 1H).

$^1$H NMR (300 MHz, DMSO-d6): δ [ppm]=3.97 (s, 3H), 8.13-8.27 (m, 2H), 8.30 (s, 1H), 8.33-8.45 (m, 1H), 8.45-8.51 (m, 1H), 9.15 (s, 1H), 12.57 (s, 1H), 13.44 (br s, 1H).

This procedure was carried out at a technical scale using 2.5 kg of (XII). Two reactions were performed at this scale. Each reaction was split into 4 batches for work-up and isolation:

TABLE 2

Batches and yields after manufacturing of (VIIa) from (XII)

| Reaction # | Batch # | Yield |
|---|---|---|
| 1 (2.5 kg scale) | 1 | 1.007 kg 84.6% |
| | 2 | 1.111 kg 93.3% |
| | 3 | 1.051 kg 88.2% |
| | 4 | 1.055 kg 88.6% |
| 2 (2.5 kg scale) | 5 | 1.041 kg 87.4% |
| | 6 | 1.123 kg 94.3% |
| | 7 | 1.056 kg 88.7% |
| | 8 | 1.048 kg 88.0% |

Variant #2

2000 g (10,46 mol) methyl 5-amino-1H-indazole-6-carboxylate (XII), 1899 g (9.94 mol) 6-(trifluoromethyl)pyridinee-2-carboxylic acid (XI) and 2028 g (15.69 mol) N,N-diisopropylethylamine were mixed in 14.2 kg THF. At 0-5° C., 13.3 kg of a solution of T3P in ethyl acetate (50 wt %) was added dropwise within 30 min. Stirring was continued for 2 h at the same temperature.

Work-Up:

The reaction mixture was warmed to ambient temperature (20° C.). 3000 g of water were added while the temperature was kept at 20-25° C. Stirring was continued for 10 min. The pH was adjusted to ca. 7.4 (7-8) using 4 N aq. sodium carbonate solution. Stirring was continued for 10 min. If necessary the pH was again adjusted to 7.4 using 4 N aq. sodium carbonate solution.

The solvents (THF/ethyl acetate) were evaporated under reduced pressure (~S 200 mbar, 45-50° C. internal temperature) until the limit of stirring was reached. A mixture of 4.7 kg ethanol and 14.0 kg water was added and the pH was again adjusted to pH 7.4 (7-8) using 4 N aq. sodium carbonate solution.

The mixture was stirred for 1 h at 50° C., subsequently cooled to 20-25° C. Stirring was continued for 10 min at the same temperature. The precipitated crystals were filtered, washed with a mixture of ethanol and water (1.3 kg ethanol with 4 kg water) and dried under vacuum in a drying oven (45° C., $N_2$ flux, at least 12 h).

According to the above described procedure, four batches using 2 kg of starting material (methyl 5-amino-1H-indazole-6-carboxylate) were produced in the technical laboratory:

Yields:
Batch #1: 3476 g (95%)
Batch #2: 3449 g (95%)
Batch #3: 3476 g (95%)
Batch #4: 3494 g (96%)

The purities of all batches were determined to be >98 area % (HPLC).

HPLC (Method A): Rt=6.5 min.

MS (ESI pos): m/z=365 (M+H)$^+$ $^1$H NMR (500 MHz, DMSO-d6): δ [ppm]: 3.98 (s, 3H), 8.21 (d, 1H), 8.25 (s, 1H), 8.31 (s, 1H), 8.39 (t, 1H), 8.48 (d, 1H), 9.16 (s, 1H), 12.57 (s, 1H), 13.45 (br s, 1H).

$^1$H NMR (300 MHz, DMSO-d6): δ [ppm]=3.97 (s, 3H), 8.13-8.27 (m, 2H), 8.30 (s, 1H), 8.33-8.45 (m, 1H), 8.45-8.51 (m, 1H), 9.15 (s, 1H), 12.57 (s, 1H), 13.44 (br s, 1H).

Example #2

N-[6-(2-hydroxypropan-2-yl)-1H-indazol-5-yl]-6-(trifluoromethyl)pyridine-2-carboxamide (IIa)

In the following section, different variants of the reaction procedure and work-up are described. These procedures are oriented at the given conditions in the respective technical plants. The following experiments were performed at the exclusion of water and air using inert gas ($N_2$ or Ar).

Variant #1

50 g (137.26 mmol) of methyl 5-({[6-(trifluoromethyl)pyridin-2-yl]carbonyl}amino)-1H-indazole-6-carboxylate (VIIa) were dissolved in 800 ml THF. Under normal pressure (1 atm) ca. 300 ml THF were distilled off at 70° C. The solution was then cooled to 0-3° C.

The solution was kept at this temperature and added dropwise within 120 min to a cooled mixture of 457.5 ml (1372.55 mmol) methylmagnesium chloride 3 M in THF and 29.1 g lithium chloride (686.27 mmol) at 0-3° C. After the addition was complete, a sample was taken out of the mixture and subjected to HPLC analysis showing that conversion was complete. The mixture was poured carefully over 25 min at 0-3° C. into 500 ml half-sat. aqu. sodium chloride solution (attention: exothermic! During the first 50 ml a strong rise in temperature to 29° C. was observed!). A suspension was received which dissolved when 358 ml 20 wt % aq. citric acid were added (pH dropped from 8.08 to 4.28). Stirring was continued for 10 min at 20-25° C. 500 ml of ethyl acetate were added and stirring was continued for 10 min. The phases were separated. The mulm was added to the organic phase. 5 g of activated charcoal were added to the organic phase. The mixture was heated to 78° C. (internal temperature), stirred for 30 min at that temperature and subsequently cooled to 50° C. (internal temperature). The warm solution was filtered over celite and washed twice with 125 ml ethyl acetate. The mixture was concentrated to ca. 150 ml at ambient pressure (1 atm) and 110° C. 350 ml of toluene were added and 200 ml were distilled off at ambient pressure (1 atm) and 110° C. The product precipitated. At 60° C. internal temperature, 200 ml n-heptane were added over 45 min. The mixture was cooled to 0-3° C. and stirred for 2 h at this temperature. The product was filtered and washed twice with a mixture of 50 ml toluene/n-heptane (1:1). The precipitated product was dried in a drying oven at 40° C. and 20 mbar for >48 h.

Yield: 39.42 g (78.83%, purity 97.84 area % HPLC)

HPLC (Method A): Rt=5.8 min.

MS (ESI pos): m/z=365 (M+H)$^+$ $^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

13 batches were produced following the procedure of variant #1. The table below summarizes the respective yields. The reactions were performed at 1 kg scale with regard to the use of methyl 5-({[6-(trifluoromethyl)pyridine-2-yl]carbonyl}amino)-1H-indazole-6-carboxylate (VIIa) as starting material. In most cases, two batches were united after treatment with activated charcoal:

TABLE 3

Batches and yields after manufacturing of (IIa) from (VIIa)

| Batch # | Yield [kg] [%] |
|---|---|
| 1 | 1.597 kg |
| 2 | 79.9% |
| 3 | 1.88 kg |
| 4 | 94% |
| 5 | 1.816 kg |
| 6 | 90.8% |
| 7 | 1.66 kg |
| 8 | 83% |
| 9 | 1.752 kg |
| 10 | 87.6% |
| 11 | 1.854 kg |
| 12 | 92.7% |
| 13* | 0.919 kg 96.4% |

*single batch

Variant #2

30 g (82,353 mmol) methyl 5-({[6-(trifluoromethyl)pyridine-2-yl]carbonyl}amino)-1H-indazole-6-carboxylate (VIIa) were dissolved in 480 ml THF. Under normal pressure (1 atm) ca. 180 ml THF were distilled off at 70° C. The mixture (slight suspension) was then cooled to 0-3° C.

The solution was kept at this temperature and added dropwise within 120 min to a cooled mixture of 274.5 ml (823.528 mmol) methylmagnesium chloride 3 M in THF and 17.5 g lithium chloride (411.764 mmol) at 0-3° C. 15 min after the addition was complete, a sample was taken out of the mixture and subjected to HPLC analysis (method A) showing that (VI) was completely converted. The mixture was poured carefully over 15 min at 0-3° C. into 300 ml of water (attention: exothermic! During the first 50 ml a strong rise in temperature was observed!). 310 ml 20 wt % aq. citric acid were added (pH dropped to 4.05). Stirring was continued for 60 min at 20 to 25° C. 300 ml of ethyl acetate were added and stirring was continued for 30 min. The phases were separated. The mulm was added to the organic phase. The organic phase was washed twice with 450 ml of water. The organic phase was concentrated to 350 ml at 65° C. (internal temperature) and ambient pressure (1 atm). 250 ml ethyl acetate were added. 6 g of activated charcoal were added to the organic phase. The mixture was heated to 65° C. (internal temperature), stirred for 120 min at that temperature and subsequently cooled to 50° C. (internal temperature). The warm solution was filtered over celite and washed twice with 125 ml ethyl acetate. The mixture was concentrated to ca. 150 ml at ambient pressure (1 atm) and 110° C. 300 ml of toluene were added and 200 ml were distilled off at ambient pressure (1 atm) and 110° C. The product precipitated. At 60° C. internal temperature, 200 ml n-heptane were added over 45 min. The mixture was cooled to 0-3° C. and stirred for 2 h at this temperature. The product was filtered and washed twice with a mixture of 50 ml toluene/n-heptane (1:1). The precipitated product was dried in a drying oven at 40° C. and 20 mbar for >48 h.

Yield: 24.0 g (80%, purity: 95.8 area % HPLC)
HPLC (Method A): Rt=5.8 min.
MS (ESI pos): m/z=365 (M+H)$^+$
$^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

Variant #3

30 g (82.353 mmol) methyl 5-({[6-(trifluoromethyl)pyridine-2-yl]carbonyl}amino)-1H-indazole-6-carboxylate (VIIa) were dissolved in 600 ml THF. Under normal pressure (1 atm) ca. 150 ml THF were distilled off at 70° C. The mixture (slight suspension) was then cooled to 0-3° C.

The solution was kept at this temperature and added dropwise within 120 min to a cooled mixture of 274.5 ml (823.528 mmol) methylmagnesium chloride 3 M in THF and 17.5 g (411.76 mmol) lithium chloride at 0-3° C. The dropping funnel was rinsed twice with 10 ml THF. 15 min after the addition was complete, a sample was taken out of the mixture and subjected to HPLC analysis showing that (VIIa) was completely converted. The mixture was poured carefully over 10 min at 0-3° C. into 300 ml of water (attention: exothermic! During the first 50 ml a strong rise in temperature to 25° C. was observed!). 250 ml 20 wt % aq. citric acid were added (pH dropped from 8 to 4). Stirring was continued for 30 min at 20-25° C. 300 ml of ethyl acetate were added and stirring was continued for 10 min. The phases were separated. The mulm was added to the organic phase. The organic phase was washed twice with 200 ml of 1 wt % sodium chloride aq. solution. The phases were separated. The organic phase was concentrated to 250 ml at 65° C. (internal temperature) and ambient pressure (1 atm). 150 ml ethyl acetate and 6 g of activated charcoal were added to the organic phase. The mixture was heated to 65° C. (internal temperature), stirred for 120 min at that temperature and subsequently cooled to 50° C. (internal temperature). The warm solution was filtered over celite and washed twice with 50 ml ethyl acetate. The mixture was concentrated to ca. 100 ml at ambient pressure (1 atm) and 110° C. 300 ml of isopropanol were added. 300 ml were distilled off at ambient pressure (1 atm) and 110° C. 300 ml isopropanol were added again and distilled off (ca. 355 ml) at 110° C. The resulting suspension was cooled to 20-25° C. 45 ml water were added over 45 min. The mixture was stirred for 1 h. The precipitated product was filtered and washed with 50 ml of a water/isopropanol (1:1) mixture. The precipitated product was dried in a drying oven at 50° C. and 20 mbar for >48 h.

Yield: 24.9 g (83%, purity: 97.84 area % HPLC)
HPLC (Method A): Rt=5.8 min.
MS (ESI pos): m/z=365 (M+H)$^+$
$^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

Variant #4

This variant was used for the production of technical batches at kg scale (>10 kg).

60 g (164.706 mmol) methyl 5-({[6-(trifluoromethyl)pyridine-2-yl]carbonyl}amino)-1H-indazole-6-carboxylate (VIIa) were dissolved in 1500 ml THF. Under normal pressure (1 atm) ca. 600 ml THF were distilled off at 70° C. The mixture (yellow solution) was then cooled to 0-3° C.

The solution was kept at this temperature and added dropwise within 120 min to a cooled mixture of 550 ml (1647.06 mmol) methylmagnesium chloride 3 M in THF and 35 g (823.53 mmol) lithium chloride at 0-3° C. 15 min after the addition was complete, a sample was taken out of the mixture and subjected to HPLC analysis showing that the conversion of (VIIa) was complete. The mixture was poured carefully over 15 min at 0-3° C. into 600 ml of water (attention: exothermic! During the first 50 ml a strong rise in temperature was observed!). 600 ml 20 wt % aq. citric acid were added (pH dropped to 4). Stirring was continued for 30 min at 20-25° C. The phases were separated. The organic phase was washed twice with 400 ml of 1 wt % sodium chloride aq. solution. The mulm was added to the organic phase. The phases were separated. The organic phase was concentrated to 700 ml at 65° C. (internal temperature) and ambient pressure (1 atm). 500 ml ethyl acetate and 12 g of activated charcoal were added to the organic phase. The mixture was heated to 65° C. (internal temperature), stirred for 120 min at that temperature and subsequently cooled to 50° C. (internal temperature). The warm solution was filtered over celite and washed twice with 200 ml ethyl acetate. Concentration was continued under reduced pressure (200 mbar). A solvent swap to touluene was performed (remaining volume ca. 850 mL). The resulting suspension was cooled to 0-3° C. The precipitated product was filtered and washed with 50 ml of toluene. The precipitated product was dried in a drying oven at 50° C. and 20 mbar for >48 h.

Yield: 51.2 g (85.3%, purity: 96.51 area % HPLC)
HPLC (Method A): Rt=5.8 min.
MS (ESI pos): m/z=365 (M+H)$^+$
$^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

Variant #5

Purification via Stirring in Isopropanol/Water

Depending on the purity of the crude product, an additional purification step via stirring in mixtures of isopropanol and water, preferably 1:1, can be performed. Depending on the purity of the crude product, stirring is performed in a range of 2-10 volumes with regard to the crude starting material. The following example describes stirring in 3 volumes isopropanol/water: 7.5 g N-[6-(2-hydroxypropan-2-yl)-1H-indazol-5-yl]-6-(trifluoromethyl)pyridine-2-carboxamide (IIa) with a purity of 95 area % (HPLC) were stirred in 22.5 ml of a 1:1 (vol) mixture of water and isopropanol for 2 h at 20° C. The suspension was then filtered and the product washed with 4 ml of the same solvent mixture. The product was dried in drying oven at 50° C. under vacuum (<100 mbar).

Yield: 6.8 g (90.7%, purity >98 area % HPLC)

HPLC (Method A): Rt=5.8 min.

MS (ESI pos): m/z=365 (M+H)$^+$ $^1$H-NMR (400 MHz, DMSO-d6): δ [ppm]=1.63 (s, 6H), 5.99 (s, 1H), 7.50 (s, 1H), 8.06 (s, 1H), 8.17 (d, 1H), 8.37 (t, 1H), 8.46 (d, 1H), 8.78 (s, 1H), 12.33 (s, 1H), 12.97 (br s, 1H).

Example #3

3-Hydroxy-3-methylbutyl-4-methylbenzenesulfonate (VI)

Variant #1

This variant was used for the production of technical batches at kg scale.

To a solution of 100 g 3-methylbutane-1,3-diol (IX) in 200 ml (264 g) dichloromethane were added 147 ml (107 g) triethylamine along with 6.0 g 4-dimethylaminopyridine (DMAP). The reaction mixture was then cooled to 0° C. (0±5° C.).

In parallel, 192 g of 4-toluenesulfonyl chloride (X) were dissolved in 400 ml (528 g) dichloromethane. The resulting slightly cloudy solution was then dropped over 1.5 h to the reaction mixture at 0-5° C. When the temperature of the reaction reached 5° C., the addition was paused and continued when the internal temperature had dropped to 0° C. After complete addition, the reaction mixture was warmed to ambient temperature (20-25° C.) over 1 h. The reaction mixture was then continuously stirred at ambient temperature for 12-18 h (preferably 15 h).

Subsequently, 500 ml of water were added to the reaction mixture. The mixture was stirred for additional 2 h at 20-25° C. The phases were separated. The mulm was collected in the aqueous phase. 500 ml of water were added to the organic phase and the pH was adjusted to 1.9 using 5 ml 2 N aq. HCl. After phases were separated, 500 ml ½-saturated aq. NaCl-solution was added to the organic phase. The pH was adjusted to 7 using sat. aq. NaHCO$_3$-solution. The phases were separated and the organic phase was concentrated via rotary evaporation in vacuo (down to 14 mbar) at 40° C. The product was obtained as viscous yellow oil.

Yield: 222.3 g (89.6%, purity: 91.9 area % HPLC)

HPLC (Method A): Rt=5.3 min.

MS (ESI pos): m/z=241 [M-OH]$^+$ $^1$H-NMR (500 MHz, DMSO-d6): δ [ppm]=1.12 (s, 6H), 1.78 (t, 2H), 2.50 (s, 3H), 4.20 (t, 2H), 4.47 (br s, 1H), 7.56 (d, 2H), 7.87 (d, 2H).

This procedure was carried out at a technical scale using 1.5 kg of (IX). Nine batches were produced. An overview is given in the table below.

TABLE 4

Batches and yields after manufacturing of (VI) from (IX)

| Batch # (1.5 kg scale) | Yield |
|---|---|
| 1 | 3.477 kg |
| | 93.4% |
| 2 | 3.521 kg |
| | 94.6% |
| 3 | 3.458 kg |
| | 92.9% |
| 4 | 3.487 kg |
| | 93.7% |
| 5 | 3.499 kg |
| | 94.0% |
| 6 | 3.490 kg |
| | 93.8% |
| 7 | 3.492 kg |
| | 93.8% |
| 8 | 3.624 kg |
| | 97.4% |
| 9 | 3.467 kg |
| | 93.2% |

Variant #2

400 g 3-methylbutane-1,3-diol were emulsified in 607 ml (528 g) toluene at ambient temperature (20-25° C.). The emulsion was cooled to 0° C. 589 ml (427.5 g) of triethylamine were added over 15 min (slightly exothermic). 23.5 g 4 dimethylaminopyridine (DMAP) were added. Within 10 min the reaction mixture had turned into a solution.

In parallel, 768.8 g of 4-toluenesulfonyl chloride were dissolved in 1214 ml (1056 g) toluene (endothermic!). The resulting slightly cloudy solution was filtered and the filtrate was dropped within 2 h to the reaction mixture at 0° C. After complete addition, stirring was continued at 0° C. for 12-18 h (preferably 15 h). A white precipitate had formed (triethylammonium chloride). The precipitate was filtered off and the resulting clear solution (2603 g) was used as a 30-35 wt % solution of 3-hydroxy-3-methylbutyl-4-methylbenzenesulfonate (VI) in the alkylation of N-[6-(2-hydroxypropan-2-yl)-1H-indazol-5-yl]-6-(trifluoromethyl)pyridine-2-carboxamide (IIa) in transformations analogous to example #5 variant #2.

HPLC (Method B): Rt=4.68 min.

Variant #3

This variant was used for the production of technical batches at kg scale.

1.57 kg 3-methylbutane-1,3-diol (IX) were emulsified in 4.0 kg toluene at ambient temperature (20-25° C.). 2 kg of solvent were distilled off at ambient pressure (T≥110° C.). The emulsion was cooled to 0° C. (internal temperature). 1.63 kg of trimethylamine and 89 g 4-dimethylaminopyridine (DMAP) were added along with 0.1 kg toluene and stirred for 15 min. (slightly exothermic).

In parallel, 2.65 kg of 4-toluenesulfonyl chloride were dissolved in 3.7 kg toluene (endothermic!, therefore warmed to ambient temperature). The resulting slightly cloudy solution was filtered and the filter was washed with 0.11 kg toluene. The resulting filtrate was dropped within 5 h to the reaction mixture at 0° C. After complete addition, stirring was continued at 0° C. for 12-18 h (preferably 15 h). A white precipitate had formed (triethylammonium chloride). The precipitate was filtered off and the precipitate washed with 3×1.88 kg toluene. The resulting clear solution (14.4 kg) was determined to have a content of 25.4 wt % of 3-hydroxyl-3-methylbutyl-4-methylbenzenesulfonate (VI) and was used without further work-up in the alkylation reaction of N-[6-(2-hydroxypropan-2-yl)-1H-indazol-5-yl]-6-(trifluoromethyl)pyridine-2-carboxamide (IIa). This solution was used in the transformation depicted in example #5 variant #3.
HPLC (Method C): Rt=2.68 min.

Example #4

2-(3-Hydroxy-3-methylbutyl)-5-({[6-(trifluoromethyl)pyridin-2-yl]carbonyl}amino)-2H-indazole-6-carboxylate (V)

This variant was used for the production of technical batches at kg scale.

1200 g of methyl 5-({[6-(trifluoromethyl)pyridin-2-yl]carbonyl}amino)-1H-indazole-6-carboxylate (VIIa), 12.0 L N,N-diisopropylethylamine and 7.5 L toluene were mixed at ambient temperature (20-25° C.). The resulting yellow suspension was heated to an internal temperature of 111° C. (120° C. jacket temperature). A solution of 4255 g 3-hydroxy-3-methylbutyl-4-methylbenzene-sulfonate (VI) in 4.25 L toluene was slowly dosed to the reaction mixture over 10 h via syringe pump. After complete addition, the dropping funnel was rinsed with 0.25 L toluene. The reaction mixture was then cooled to an internal temperature of 104° C. and was stirred at that temperature for 12-18 h (preferably 15 h). The reaction mixture was then cooled to 45° C. (jacket temperature). The volume of the reaction mixture was reduced at 45° C. to 53° C. (jacket temperature) under vacuum (113-70 mbar) to a viscous, well stirrable residue (ca. 19.6 L distillate removed). At an internal temperature of 28-33° C. (careful: prevent crystallization by fast addition of ethyl acetate) 12 L ethyl acetate were added followed by 12 L water. The mixture was stirred for 5 min at an internal temperature of 22° C. The phases were separated. The mulm was added to the aqueous phase. The aqueous phase was extracted with 3.85 L ethyl acetate. The organic phases were combined and 12 L of water were added. The pH of the mixture was adjusted from 10 to 6.9 (6-7) using conc. acetic acid. The organic phase was evaporated to dryness at 40° C. under vacuum (down to 45 mbar). The residue was dissolved in 1 L dichloromethane and evaporated to dryness. This was repeated two more times. The resulting residue (1.772 kg) was dissolved in 26.58 L dichloromethane (15 L/kg). The resulting solution was adjusted to a concentration of 20 L/kg (3.6 wt %) and subsequently subjected to column chromatography (chromasil 13 μm; gradient: ethyl acetate/n-hexane 10:90 to 100:0). The resulting pure product was provided as a 10-15 wt % solution in THF for the following step.

Four reactions were run at 1.2 kg scale each. These have been comprised in one batch for column chromatography. Further three reactions were run at the same scale and also comprised in one batch for column chromatography. The following table shows the results with respect to yield and purity:

TABLE 5

Yields and purity (HPLC) after manufacturing of (V) from (VIIa)

| Batch # | Reaction # (1.2 kg scale (VIIa)) | Yield | Purity (HPLC) |
|---|---|---|---|
| 1 | 1 | 3.39 kg 47% | 99.8 area % |
|   | 2 |   |   |
|   | 3 |   |   |
|   | 4 |   |   |
| 2 | 5 | 2.40 kg 45% | 99.5 area % |
|   | 6 |   |   |
|   | 7 |   |   |

HPLC (Method B): Rt=5.9 min.
MS (ESI pos): m/z=451 (M+H)$^+$
$^1$H-NMR (400 MHz, DMSO-d6): δ [ppm]=1.16 (s, 6H), 2.00-2.13 (m, 2H), 3.96 (s, 3H), 4.45-4.64 (m, 3H), 8.20 (d, 1H), 8.34-8.42 (m, 1H), 8.42-8.49 (m, 2H), 8.55 (s, 1H), 9.05 (s, 1H), 12.52 (s, 1H).

Alternatively, crystallization can be performed in order to obtain the purified product as a neat solid:

300 g of a 15 wt % solution of 2-(3-hydroxy-3-methylbutyl)-5-({[6-(trifluoromethyl)pyridine-2-yl]carbonyl}amino)-2H-indazole-6-carboxylate (V) in THF was concentrated at 43° C. jacket temperature under vacuum (300-320 mbar). Distillation was continued until the limit of stirability was reached (199.6 g residue). At ambient pressure and a jacket temperature of 43° C. 255 g of n-heptane were added over 15 min to the residue. Stirring was continued for 1 h before the mixture was cooled to 20° C. within 1 h. The mixture was stirred at that temperature for 12-18 h (preferably 15 h). The product was filtered, washed twice with 25 g n-heptane and dried in a drying oven at 40° C. under vacuum (<200 mbar).

Example #5

N-[2-(3-hydroxy-3-methylbutyl)-6-(2-hydroxypropan-2-yl)-2H-indazol-5-yl]-6-(trifluoromethyl)-pyridine-2-carboxamide (I)

Variant #1

The following experiment was performed at the exclusion of water and air using inert gas (N$_2$ or Ar, preferably Ar).

4.0 kg anhydrous THF were placed in a reaction vessel under inert atmosphere and cooled to −15° C. (internal temperature). 4.61 kg 3 M methylmagnesium chloride solution in THF were added. The dropping funnel was rinsed with 0.433 kg THF.

In parallel, 9.901 kg of a 10.1 wt % solution of methyl 2-(3-hydroxy-3-methylbutyl)-5-({[6-(trifluoromethyl)pyridine-2-yl]carbonyl}amino)-2H-indazole-6-carboxylate (V) was concentrated at 40° C. under vacuum. App. 5 kg were distilled off and 2.087 kg residue remained. To the residue 4.279 kg THF were added resulting in a 15 wt % solution of (V) in THF.

The 15 wt % solution of methyl 2-(3-hydroxy-3-methylbutyl)-5-({[6-(trifluoromethyl)pyridin-2-yl]carbonyl}amino)-2H-indazole-6-carboxylate (V) in THF was slowly dosed over at least 1 h 45 min to the Grignard solution at −15° C. The container and pump were rinsed with 0.3 kg THF. Stirring was continued for 30-40 min at the same temperature. Meanwhile, a 15 wt % aq. solution of citric acid (2.8 kg citric acid monohydrate+14.267 kg water) was placed in a reaction vessel and cooled to 0° C. (internal temperature). The cold reaction mixture (0-10° C.) was dosed within 30 min to the aqueous citric acid solution. It was rinsed with 1 kg THF. The quenched reaction mixture was then allowed to warm to ambient temperature (20-25° C.) over a period of 40 min. The phases were separated. The aqueous phase was extracted with 10 L ethyl acetate. The organic phases were combined and washed with 6.66 L water (phases were stirred for 15 min). The combined organic phases were concentrated until the limit of stirability was reached (45° C. jacket temperature, vacuum 150 mbar to 70 mbar; app. 3-4 L residual volume). 6 kg of ethanol were added to the residue. The solution was concentrated under vacuum (45 to max. 60° C. jacket temperature; 8.5 L distillate) and again 6 kg of ethanol were added. The solution was again concentrated under vacuum (distillate: 7.95 L). Then, 6 kg of ethanol were added to the residue.

Crude Crystallization:

The resulting solution was heated to an internal temperature of 31-32° C. 18 L water were added within 1 h resulting in a yellowish suspension. The mixture was cooled to 20° C. within 1 h and stirred for 20 min. The precipitate was filtered and washed twice with a mixture of 0.416 kg ethanol +1.25 kg water. The mother liquor was filtrated again and the precipitate washed with a mixture of 1.7 kg ethanol/water (1:3). The crude product was dried in a drying oven at 40° C. under vacuum (<200 mbar) for 12-18 h (preferably 15 h).

Recrystallization (3 reactions (crude product batches) were combined in one batch for purification):

The combined crude products (2.855 kg) were suspended in 18.27 kg of a 9:1 mixture of toluene/acetone. The mixture was then heated to 80° C. internal temperature and 6.67 kg of a 9:1 mixture of toluene/acetone were added in portions of 1.1 L. Upon dissolution of the product, the mixture was cooled to 55° C. Then slowly cooled to 52° C. and stirred for 1 h at that temperature. The product started to crystallize at 53° C. (Seeding with crystals is optional). Stirring was continued for 1 h at 52° C. (internal temperature). The suspension was then cooled within 2 h to 20° C. The suspension was stirred at 20° C. for 12-18 h (preferably 15 h). The product was filtered and washed with 1.11 kg toluene/acetone 9:1 and subsequently with 1.11 kg toluene. The product was dried in a drying oven at 40° C. under vacuum (<200 mbar) for 12-18 h (preferably 15 h).

In order to obtain a defined crystal habit the pure product is subjected to crystallization with ethanol and water (as described above, analogous to first crystallization from ethanol/water). Thus, needles of the product are obtained in high purity: 8.37 kg ethanol are added to 2.32 kg of the purified product. The mixture is warmed to 32° C. At that temperature 25.1 kg water are added over a period of 1 h. The resulting suspension is cooled to 20° C. within 1 h and stirred for 20 min. The product is filtrated and washed with 7.43 kg of a mixture of ethanol/water (1:3). The precipitate is washed two more times with 7.43 kg of a mixture of ethanol/water (1:3). The product was dried in a drying oven at 50° C. under vacuum (<200 mbar) for 12-18 h (preferably 15 h).

TABLE 6

Yields and purity (HPLC) after manufacturing of (I) from (V)

| Batch # | Reaction # (1.0 kg scale (V)) | Yield | Purity (HPLC) Content |
|---|---|---|---|
| 1 | 1 | 2.314 kg 77.1% | 98.1 area % 97.92% |
|   | 2 |   |   |
|   | 3 |   |   |
| 2 | 4 | 2.164 kg 72.1% | 98.25 area % 97.96% |
|   | 5 |   |   |
|   | 6 |   |   |

HPLC (Method C): Rt=3.50 min.

MS (ESI pos): m/z=451 (M+H)$^+$ $^1$H-NMR (400 MHz, DMSO-d6): δ [ppm]=1.15 (s, 6H), 1.62 (s, 6H), 1.99-2.08 (m, 2H), 4.45-4.50 (m, 2H), 4.51 (s, 1H), 5.94 (s, 1H), 7.57 (s, 1H), 8.16 (d, 1H), 8.35 (s, 1H), 8.36-8.39 (m, 1H), 8.43-8.47 (m, 1H), 8.71 (s, 1H), 12.35 (s, 1H).

$^1$H-NMR (400 MHz, DMSO-d6): δ [ppm]=1.15 (s, 6H), 1.63 (s, 6H), 2.00-2.09 (m, 2H), 4.43-4.55 (m, 3H), 5.94 (s, 1H), 7.57 (s, 1H), 8.16 (d, 1H), 8.34-8.39 (m, 2H), 8.45 (d, 1H), 8.72 (s, 1H), 12.36 (s, 1H).

Variant #2

An approximately 30-35 wt % solution of 3-hydroxy-3-methylbutyl-4-methylbenzenesulfonate (VI) in toluene was freshly prepared analogously to the procedure given in example #3 variant #2. 100 g of N-[6-(2-hydroxypropan-2-yl)-1H-indazol-5-yl]-6-(trifluoromethyl)pyridine-2-carboxamide (IIa) were suspended in 560.5 g toluene. The mixture was heated to 104° C. (110° C.) within 30 min. Within 5 h, 212.8 g N,N-diisopropylethylamine and 1013 g of a 35 wt % solution of (VI) in toluene were dosed simultaneously to the reaction mixture within 5 h. Thereby, it is important that an excess of base is always present during the reaction. After complete addition, the reaction mixture was stirred at 104° C. (110° C.) overnight (18 h). The reaction mixture (two phases had formed) was then cooled to 45° C. and concentrated under vacuum (down to app. 50 mbar) to a viscous, stirrable residual volume of app. 750 ml (1189.9 g were distilled off). The residue was then cooled to 20° C. and 920 g ethyl acetate were added followed by a mixture of 110 g conc. acetic acid and 840 g water. The mixture was stirred for 5 min at 20° C. The phases were separated. The aqueous phase was reextracted with first 840 g and then with 420 g ethyl acetate. The organic phases were combined and 840 g water were added. Phases were separated. The phases were recombined and the mixture was heated to 50° C. (internal temperature) and stirred for 1 hour at that temperature. Phases were separated and the organic phase was concentrated under vacuum at a temperature of 50-60° C. to a residual volume of app. 213.4 g.

840 g isopropanol were added to the residue. The solvents were evaporated to a final residue of app. 380.9 g in order to remove all remaining ethyl acetate. This procedure can be repeated if necessary. To the isopropanolic residue (380.9 g) were added 187.6 g of isopropanol and 419 g of isopropanol. This resulted in a 27.3 wt % solution of crude (I) in isopropanol (purity: 78.4 area % HPLC).

HPLC (Method C): Rt=3.58 min.

316.9 g of this solution were used in the following precipitation procedure: The solution was kept at 25° C. Within 30 min 984.4 g of water were added. Seed crystals (1%; 0.33 g) were added. Stirring was continued for 30 min. Within 2 h 564 g of water were added. The resulting suspension was stirred for 1 h and filtered. The precipitate was washed with a mixture of 15.4 g isopropanol and 46.8 g water followed by 62.1 g water. The product is dried in a drying oven at 50° C. under vacuum for 18 h.

Using this procedure, crude product was obtained in 81% yield with a purity of 89.2 area % (84.4 wt %).

HPLC (Method C): Rt=3.55 min.

Material obtained with the afore described work-up can be purified via repetitive crystallization from toluene/acetone 9:1 in the presence of activated charcoal similar to the crystallization described in the procedure for variant #1. A definite crystal form can be obtained via recrystallization with ethanol and water (see also procedure variant #1). An example is given here: 23.0 g crude (I) (89 area % HPLC; 86 wt %; method D) were suspended in 70 g of a toluene/acetone mixture (9:1). The mixture is heated to 80-82° C. internal temperature (slight reflux observed). 87 g of the toluene/acetone mixture (9:1) were added. A clear solution resulted. 4.6 g of activated charcoal were added. Stirring was continued for 30 min at that temperature. The hot solution was filtrated over 2.5 g harbolite 900. The filter was rinsed with 9.5 g of the toluene/acetone mixture (9:1). Crystallization in the filtrate started at 60° C. The mixture was stirred at 60-62° C. internal temperature for 1 h. The suspension was then cooled to 22° C. within 2.5 h and stirred for app. 16 h (overnight). The purified product was filtrated and washed with 20 g of the toluene/acetone mixture (9:1) and dried in a drying oven under vacuum at 50° C. for 24 h.

Yield: 14.9 g (64.8%; purity: 96.2 area % HPLC; 94.1 wt %)

HPLC (Method C): Rt=3.47 min.

14.9 g of purified product were obtained of which 13.6 g were again subjected to recrystallization: 13.6 g purified (I) were suspended in 85.7 g of a toluene/acetone mixture (9:1). The mixture is heated to 80 to 82° C. internal temperature. 32.7 g of the toluene/acetone mixture (9:1) were added. A clear solution resulted. 2.8 g of activated charcoal were added. Stirring was continued for 30 min at that temperature. The hot solution was filtrated over 2.5 g harbolite 900. The filter was rinsed with 10 g of the toluene/acetone mixture (9:1). Crystallization in the filtrate started at 70° C. The mixture was stirred at 70° C. internal temperature for 1 h. The suspension was then cooled to 22° C. within 4 h and stirred for app. 18 h. The purified product was filtrated and washed with 10 g of the toluene/acetone mixture (9:1) and dried in a drying oven under vacuum at 50° C. for 24 h.

Yield: 11.5 g (84.6%; purity: 97.7 area % HPLC; 91.5 wt %)

HPLC (Method C): Rt=3.48 min.

11.5 g of a the purified product were obtained of which 9 g were subjected to crystallization with ethanol/water for obtaining the right crystal form and removing inclusions of toluene (7.3 wt %): To 9.0 g of purified (I) 32.4 g ethanol were added and the mixture was warmed to 32° C. (internal temperature). 92.7 g water were added to the solution within 1 h. The resulting suspension was stirred for 30 min at that temperature. The suspension is cooled to 22° C. within 1 h. The crystalline product was filtrated and washed with a mixture of 6.6 g water and 3.3 g ethanol and dried in a drying oven under vacuum at 50° C. for 24 h.

Yield: 8.0 g (88.9%; purity: 99.3 area % HPLC; 101 wt %)

HPLC (Method C): Rt=3.52 min.

MS (ESI pos): m/z=451 (M+H)+

$^1$H-NMR (400 MHz, DMSO-d6): δ [ppm]=1.15 (s, 6H), 1.62 (s, 6H), 1.99-2.08 (m, 2H), 4.45-4.50 (m, 2H), 4.51 (s, 1H), 5.94 (s, 1H), 7.57 (s, 1H), 8.16 (d, 1H), 8.35 (s, 1H), 8.36-8.39 (m, 1H), 8.43-8.47 (m, 1H), 8.71 (s, 1H), 12.35 (s, 1H).

$^1$H-NMR (400 MHz, DMSO-d6): δ [ppm]=1.15 (s, 6H), 1.63 (s, 6H), 2.00-2.09 (m, 2H), 4.43-4.55 (m, 3H), 5.94 (s, 1H), 7.57 (s, 1H), 8.16 (d, 1H), 8.34-8.39 (m, 2H), 8.45 (d, 1H), 8.72 (s, 1H), 12.36 (s, 1H).

Variant #3

A 25.4 wt % solution of 3-hydroxy-3-methylbutyl-4-methylbenzenesulfonate (VI) in toluene (11.27 kg) was freshly prepared analogously to the procedure given in example #3 variant #3. 1.01 kg of N-[6-(2-hydroxypropan-2-yl)-1H-indazol-5-yl]-6-(trifluoromethyl)pyridine-2-carboxamide (IIa) were suspended in 5.66 kg toluene and 1.72 kg N,N-diisopropylethylamine. The mixture was heated to reflux (>110° C.). The 25.4 wt % solution of 3-hydroxy-3-methylbutyl-4-methylbenzenesulfonate (VI) in toluene was dosed to the reaction mixture within 10 h. After complete addition, the pump and connections were rinsed with 0.35 kg toluene and the reaction mixture was stirred at reflux for 14-24 h (preferably 18 h). The reaction mixture was then cooled to 60° C. (internal temperature), 1.3 kg of toluene were added and the mixture was concentrated under vacuum (final pressure: 90 mbar) to a viscous, stirrable residual volume of app. 8.3 l (13.8 l distilled off). The residue was then cooled to 50° C. and 9.3 kg butyl acetate were added followed by a mixture of 1.1 kg conc. acetic acid and 8.5 kg water. The mixture was stirred for 1 h at 50° C. The phases were separated. The aqueous phase was extracted with 8.5 kg butyl acetate. The organic phases were combined and 8.49 kg of a half-saturated aqueous NaCO$_3$ solution was added. The mixture was stirred for at least 15 min at 50 C. Phases were separated and the organic phase was extracted with 6.1 kg of water. The organic phase was then concentrated under vacuum at a jacket temperature of 50-60° C. to a residual volume of app. 6.3 l (18.7 l distilled off). 6.1 kg of butyl acetate were added and the mixture was again concentrated under vacuum at 50-60° C. (residual volume: 5.9 l; 5.9 l distilled off). The mixture was then warmed to 93° C. (internal temperature) and stirred at this temperature for 1 h. Within 30 min the resulting solution was cooled to 83° C. and seeded with 2 g of the targeted product (seeding is optional). The resulting suspension was stirred for 10 min. The mixture was then cooled to 60° C. within 2 h and stirred for 30 min at this temperature. The suspension was then warmed to 78° C. in at least 30 min and stirred at this temperature for at least 30 min. The mixture was then cooled to 22° C. in at least 6 h. The suspension was stirred at that temperature for at least 10 min and subsequently filtered. The precipitate was washed with 1.1 kg butyl acetate dried in a drying oven under vacuum at 60° C. for 21 h.

Yield: 2.11 kg (61.6%; purity: 98.6 area % HPLC)

HPLC (Method C): Rt=3.50 min.

MS (ESI pos): m/z=451 (M+H)$^+$

Preparation of Crystalline Forms of N-[2-(3-Hydroxy-3-methylbutyl)-6-(2-hydroxypropan-2-yl)-2H-indazol-5-yl]-6-(trifluoromethyl)pyridine-2-carboxamide (I)

Preparation of Hydrate of N-[2-(3-Hydroxy-3-methylbutyl)-6-(2-hydroxypropan-2-yl)-2H-indazol-5-yl]-6-(trifluoromethyl)pyridine-2-carboxamide (I)

When the term "room temperature" is used in the following synthesis protocols, a temperature of about 20 to 25° C. is meant.

Example 0

For obtaining the product in a defined crystalline form with cGMP quality, the following recrystallization procedure is performed:

7.5 kg of N-[2-(3-hydroxy-3-methylbutyl)-6-(2-hydroxypropan-2-yl)-2H-indazol-5-yl]-6-(trifluoromethyl)pyridine-2-carboxamide (I) were dissolved in 39.9 kg of ethanol at 55° C. The resulting solution was subjected to clarifying filtration and the filter was washed with 5 kg ethanol. The solution was heated to 65° C. and stirred at this temperature. 131.6 kg of water were slowly dosed to the mixture. 15% (19.7 kg) of the total amount (131.6 kg) of water were added directly, further 21% (28.0 kg) were added within 2 h, and further 13% (16.7 kg) were added subsequently within 1 h, further 21% (28.0 kg) within 0.5 h and the remaining 30% (39.2 kg) within 0.5 h. After complete addition, the resulting suspension was stirred for 1 h at 65° C. and subsequently cooled within 5 h to 20° C. The suspension was stirred for 5 h at this temperature, filtrated and the precipitate was washed twice with a mixture of 3.5 kg ethanol and 8.7 kg water. The product was dried in a drying oven under vacuum (70° C., ≤40 mbar).

Yield: 7.2 kg (96.0%; purity: 98.7 area % HPLC)

Content (assay for use): 96.5 wt %

Ethanol <0.13 wt %
3-Hydroxy-3-methylbutyl 4-methylbenzenesulfonate (VI) <20 ppm
HPLC (Method C): Rt=3.50 min.
MS (ESI pos): m/z=451 (M+H)$^+$
$^1$H-NMR (400 MHz, DMSO-d6): δ [ppm]=1.15 (s, 6H), 1.62 (s, 6H), 1.99-2.08 (m, 2H), 4.45-4.50 (m, 2H), 4.51 (s, 1H), 5.94 (s, 1H), 7.57 (s, 1H), 8.16 (d, 1H), 8.35 (s, 1H), 8.36-8.39 (m, 1H), 8.43-8.47 (m, 1H), 8.71 (s, 1H), 12.35 (s, 1H).
1H-NMR (400 MHz, DMSO-d6): δ [ppm]=1.15 (s, 6H), 1.63 (s, 6H), 2.00-2.09 (m, 2H), 4.43-4.55 (m, 3H), 5.94 (s, 1H), 7.57 (s, 1H), 8.16 (d, 1H), 8.34-8.39 (m, 2H), 8.45 (d, 1H), 8.72 (s, 1H), 12.36 (s, 1H).

Example 1

Preparation of Hydrate of N-[2-(3-Hydroxy-3-methylbutyl)-6-(2-hydroxypropan-2-yl)-2H-indazol-5-yl]-6-(trifluoromethyl)pyridine-2-carboxamide (I)

19.9 mg of compound (I) obtained from example #5, variant #1 was dissolved in 100 μL Methanol at room temperature in a 1.5 mL vessel which was closed afterwards. The sample was stirred for 5 minutes and exposed to ultrasonic at room temperature for additional 5 minutes. The sample was evaporated at room temperature to complete dryness.

Example 2

Preparation of an Hydrate of N-[2-(3-Hydroxy-3-methylbutyl)-6-(2-hydroxypropan-2-yl)-2H-indazol-5-yl]-6-(trifluoromethyl)pyridine-2-carboxamide (I)

102.10 mg of compound (I) obtained from example #5, variant #1 was dissolved in 3 mL isobutanol at 50° C. in a 4 mL vessel which was closed afterwards. The sample was stirred for 5 minutes and exposed to ultrasonic at 50° C. for additional 5 minutes. The sample was evaporated at 50° C. to complete dryness.

Example 3

Preparation of Formamide Solvate Form of N-[2-(3-Hydroxy-3-methylbutyl)-6-(2-hydroxypropan-2-yl)-2H-indazol-5-yl]-6-(trifluoromethyl)pyridine-2-carboxamide (I)

A suspension of 100.30 mg compound (I) obtained from example #5, variant #1 in 2 mL formamide was stirred in an hermetically closed vial for 7 days at room temperature. The solid was filtered off afterwards.
XRPD data of hydrate, anhydrate and formamide solvate of compound (I) are given in table 1 and FIG. 1, FIG. 2, and FIG. 3.

Example 4

Pharmaceutical Composition Containing One of the Crystalline Forms (Hydrate, Anhydrate or Formamid Solvate Form) of N-[2-(3-Hydroxy-3-methylbutyl)-6-(2-hydroxypropan-2-yl)-2H-indazol-5-yl]-6-(trifluoromethyl)pyridine-2-carboxamide (I)

The granulation liquid is prepared by mixing the micronized form of compound of formula (I), sodium laurilsulfate, hypromellose 3 cP, and purified water in bulk. Mannitol, cellulose microcrystalline, and croscarmellose sodium are mixed. This blend is granulated with the granulation liquid in the fluidized bed granulator. The granules are dried and sieved.

The granules are mixed with sieved magnesium stearate in a blender resulting in the ready-to-press mixture. The ready-to-press mixture is compressed into tablets. The uncoated tablets are tested for uniformity of mass, thickness, resistance to crushing, disintegration, and friability. Hypromellose 5 cP, macrogol 3350, talc, titanium dioxide, and ferric oxide red are combined with purified water in bulk to result in a homogeneous coating suspension, which is sprayed onto the tablets in a suitable coating device, e.g. perforated drum coater.

TABLE 2

| Composition of tablet | |
|---|---|
| Composition | Amount [mg] |
| Drug substance | |
| Hydrate form A of compound of formula (1) micronized | 100.00 |
| Excipients | |
| Lactose monohydrate | 116.00 |
| Cellulose microcrystalline | 91.00 |
| Croscarmellose sodium | 36.00 |
| Hypromellose 3 cP | 12.50 |
| Sodium laurilsulfate | 1.80 |
| Magnesium stearate | 2.70 |
| Purified water in bulk$^a$ | — |
| Weight (uncoated tablet) | 360.00 |
| Film-coating | |
| Hypromellose 5 cP (syn.: Hydroxypropyl methylcellulose 2910) | 5.00 |
| Macrogol 3350 (syn.: Polyethylene glycol (3350)) | 1.00 |
| Talc | 1.00 |
| Titanium dioxide $^b$ | 2.90 |
| Ferric oxide yellow$^b$ | 0.10 |
| Purified water in bulk$^a$ | — |
| Weight (film-coating) | 10.00 |
| Weight (coated tablet) | 370.00 |

Tablets each containing 25 and 100 mg of the hydrate of N-[2-(3-Hydroxy-3-methylbutyl)-6-(2-hydroxypropan-2-yl)-2H-indazol-5-yl]-6-(trifluoromethyl)pyridine-2-carboxamide were prepared following the protocol given in example 4.

Assay for Stability of a Pharmaceutical Composition Containing One of the Crystalline Forms (Hydrate, Anhydrate or Formamid Solvate) of N-[2-(3-Hydroxy-3-methylbutyl)-6-(2-hydroxypropan-2-yl)-2H-indazol-5-yl]-6-(trifluoromethyl)pyridine-2-carboxamide (I)

Coated tablet containing 25 mg or 100 mg of the hydrate form A of N-[2-(3-Hydroxy-3-methylbutyl)-6-(2-hydroxypropan-2-yl)-2H-indazol-5-yl]-6-(trifluoromethyl)pyridine-2-carboxamide (drug substance) are packaged in HDPE (High-Density Polyethylene) bottles with child resistant white polypropylene/polyethylene screw cap closures. This packaging configuration provides sufficient protection from light and humidity.

Stability studies are conducted with testing of the stability indicating parameters appearance, dissolution, degradation products, and content of drug substance at regular intervals to confirm the stability of coated tablet containing 25 mg or 100 mg of the drug substance over the proposed study duration.

The samples of coated tablets (25 mg or 100 mg) packaged in HDPE bottles are stored at 25° C./60% relative humidity, 30° C./75% relative humidity and 40° C./75% relative humidity, as well as at 2-8° C. The experiments for stability investigation are regularly performed.

Coated tablets containing either 25 mg or 100 mg of the hydrate of N-[2-(3-Hydroxy-3-methylbutyl)-6-(2-hydroxypropan-2-yl)-2H-indazol-5-yl]-6-(trifluoromethyl)pyridine-2-carboxamide (drug substance) are stable under all investigated conditions. During this storage period, no increase of degradation products and no decrease of the content of the drug substance were observed.

The invention claimed is:

1. A hydrate of the compound of formula (I)

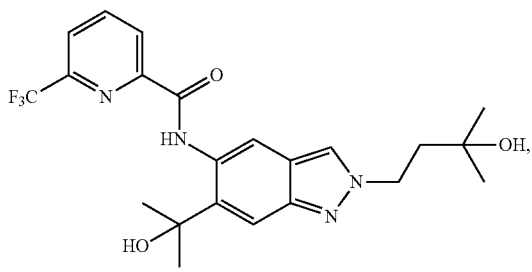

(I)

wherein the hydrate has a X-ray powder diffraction diagram at 25° C. and with Cu-K alpha 1 as radiation source displaying at least the following reflections, quoted as 2Theta value ±0.2°: 9.4, 10.8, and 15.0.

2. The hydrate of the compound of formula (I) of claim 1, wherein the hydrate has a X-ray powder diffraction diagram at 25° C. and with Cu-K alpha 1 as radiation source displaying at least the following reflections, quoted as 2Theta value ±0.2°: 9.4, 10.8, 15.0, 16.0, and 17.0.

3. The hydrate of the compound of formula (I) of claim 1, wherein the hydrate has a X-ray powder diffraction diagram at 25° C. and with Cu-K alpha 1 as radiation source displaying at least the following reflections, quoted as 2Theta value ±0.2°: 9.4, 10.8, 15.0, 16.0, 17.0, 20.1, and 22.9.

4. The hydrate of the compound of formula (I) of claim 1, wherein the hydrate has a X-ray powder diffraction diagram at 25° C. and with Cu-K alpha 1 as radiation source displaying at least the following reflections, quoted as 2Theta value ±0.2°: 9.4, 10.8, 15.0, 16.0, 17.0, 20.1, 22.9, 24.3, 26.6, and 29.8.

5. A pharmaceutical composition comprising only a hydrate of the compound of formula (I) according to claim 1 mainly and no significant fractions of another form of the compound of formula (I).

6. A pharmaceutical composition comprising a hydrate of the compound of formula (I) according to claim 1 and pharmaceutically acceptable excipients.

7. The pharmaceutical composition of claim 6, comprising only the hydrate of the compound of formula (I) mainly and no significant fractions of another form of the compound of formula (I).

8. The pharmaceutical composition of claim 6, comprising the hydrate of the compound of formula (I) in more than 85 percent by weight related to the total amount of all forms of the compound of the formula (I) present in the composition.

9. The pharmaceutical composition of claim 8, comprising the hydrate of the compound of formula (I) in more than 90 percent by weight related to the total amount of all forms of the compound of formula (I) present in the composition.

10. A method for treatment of rheumatoid arthritis in a human in need thereof, comprising administering to the human an effective amount of a hydrate of the compound of formula (I) according to claim 1.

11. A method for treatment of rheumatoid arthritis in a human in need thereof, comprising administering to the human an effective amount of a pharmaceutical composition according to claim 5.

12. A method for treatment of rheumatoid arthritis in a human in need thereof, comprising administering to the human an effective amount of a pharmaceutical composition according to claim 6.

* * * * *